(12) United States Patent
Benowitz et al.

(10) Patent No.: US 11,771,711 B2
(45) Date of Patent: Oct. 3, 2023

(54) SUBSTITUTED PYRIDINES AS DNMT1 INHIBITORS

(71) Applicant: GlaxoSmithKline Intellectual Property Development Limited, Brentford (GB)

(72) Inventors: Andrew B. Benowitz, Stevenage (GB); David T. Fosbenner, Collegeville, PA (US); Bryan Wayne King, Collegeville, PA (US); Stuart Paul Romeril, Collegeville, PA (US)

(73) Assignee: GlaxoSmith Kline Intellectual Property Development Limited, Middlesex (GB)

( * ) Notice: Subject to any disclaimer, the term of this patent is extended or adjusted under 35 U.S.C. 154(b) by 0 days.

(21) Appl. No.: 17/966,504

(22) Filed: Oct. 14, 2022

(65) Prior Publication Data
US 2023/0101987 A1 Mar. 30, 2023

Related U.S. Application Data

(63) Continuation of application No. PCT/IB2022/051637, filed on Feb. 24, 2022.

(60) Provisional application No. 63/155,325, filed on Mar. 2, 2021.

(51) Int. Cl.
| | |
|---|---|
| *A61K 31/675* | (2006.01) |
| *A61P 35/02* | (2006.01) |
| *A61K 31/44* | (2006.01) |
| *C07D 213/85* | (2006.01) |
| *C07F 9/58* | (2006.01) |

(52) U.S. Cl.
CPC .......... *A61K 31/675* (2013.01); *A61K 31/44* (2013.01); *A61P 35/02* (2018.01); *C07D 213/85* (2013.01); *C07F 9/58* (2013.01); *C07B 2200/13* (2013.01)

(58) Field of Classification Search
None
See application file for complete search history.

(56) References Cited

FOREIGN PATENT DOCUMENTS

WO 2017216727 A1 12/2017

*Primary Examiner* — Brian J Davis
(74) *Attorney, Agent, or Firm* — W. Brett Stauffer

(57) ABSTRACT

The invention relates to substituted pyridine derivatives that are inhibitors of the activity of DNA methyltransferase 1 (DNMT1). The invention also relates to pharmaceutical compositions comprising such compounds and methods of using such compounds in the treatment of cancer, pre-cancerous syndromes, beta haemoglobinopathy disorders, and other diseases associated with inappropriate DNMT1 activity.

17 Claims, 4 Drawing Sheets

SUBSTITUTED PYRIDINES AS DNMT1 INHIBITORS

CROSS REFERENCE TO RELATED APPLICATIONS

This application is a Continuation of International Application No. PCT/IB2022/051637 filed Feb. 24, 2022, which claims the benefit of U.S. Provisional Application No. 63/155,325 filed Mar. 2, 2021, the disclosures of which are incorporated herein in their entireties.

FIELD OF THE INVENTION

The invention relates to substituted pyridine derivatives that are inhibitors of the activity of DNA methyltransferase 1 (DNMT1). The invention also relates to pharmaceutical compositions comprising such compounds and methods of using such compounds in the treatment of cancer, pre-cancerous syndromes, beta haemoglobinopathy disorders, and other diseases associated with inappropriate DNMT1 activity.

BACKGROUND TO THE INVENTION

Epigenetics is a way to turn genes on and off independent of the underlaying DNA sequence. DNA methylation occurring in gene promotors is an example of a repressive epigenetic mark resulting in chromatin compaction and gene silencing. DNA methylation is mediated by the DNA methyltransferase (DNMT) family of which is comprised of five family members. Three of the family members, DNMT1, DNMT3A and DNMT3B, contain DNA methyltransferase activity. These three members are responsible for establishing the de novo DNA methylation pattern, while DNMT1 is also responsible for maintaining the methylation pattern in daughter strands following DNA replication.

In cancer, DNA methylation patterns become aberrant resulting in global hypomethylation and localized hypermethylation within promoter regions. This can result in downstream silencing of tumor suppressor genes (Ting et al. Genes Dev. 2006; 20:3215-3231). Additionally, silencing of DNMT1 results in DNA demethylation and reexpression of tumor suppressor genes resulting in tumor growth inhibition (Zhou et al. Oncol. Lett. 2014; 5: 2130-2134).

DNA methylation inhibitors (termed DNA hypomethylating agents) are clinically validated anti-cancer therapies utilized for the treatment of MDS, AML and CMML. While these agents are available, there is still significant opportunity for improvement regarding toxicity, utility in solid tumors and oral bioavailability. Hence, a novel DNMT inhibitor would be of interest for the treatment of cancer and/or any disease or condition mediated by DNA methylation. Of particular interest to this invention, is specifically targeting DNMT1 to prevent propagation of abnormal methylation patterns (such as those that occur in cancer) to daughter strands during replication.

Hemoglobin disorders, such as sickle cell anemia and beta-thalassaemia, represent the most common heritable blood diseases in the world. Sickle cell anemia and beta-thalassemia are characterized by disorders of hemoglobin, which is the oxygen carrying protein complex in red blood cells. Structurally, hemoglobin is normally composed of two pairs of proteins plus four molecules of heme. Adults and children older than about four months, express a form of hemoglobin referred to as adult hemoglobin, which predominantly consists of two alpha-globin proteins paired with two beta-globin proteins plus four molecules of heme. However, fetuses and infants typically express mostly fetal hemoglobin, which is composed of two alpha-globin proteins paired with two gamma-globin proteins plus four molecules of heme. Note that there are two forms of gamma-globin, termed G-gamma and A-gamma, that are encoded by two different genes (HBG1 and HBG2) but that are functionally equivalent to a large degree; fetal hemoglobin refers to any combination of a pair of G-gamma and/or A-gamma plus a pair of alpha-globin proteins plus four molecules of heme.

In sickle cell anemia, the gene encoding for beta-globin contains a mutation which results in an abnormal hemoglobin structure and causes red blood cells to adopt a characteristic sickle shape under certain conditions. This sickle shape leads to reduced red cell plasticity, longer capillary transit times, and frequent vaso-occlusive processes that can damage tissues and result in patient morbidity. In contrast, beta-thalassemia is characterized by inadequate beta-globin production to combine with normally produced alpha-globin. The resulting accumulation of alpha globin is toxic to red blood cell precursors, and results in ineffective erythropoiesis and extensive red blood cell hemolysis.

There is currently no approved pharmacologic treatment to cure sickle cell anemia or beta-thalassemia. However, increases in the number of red blood cells that produce fetal hemoglobin, combined with overall increases in the level of fetal hemoglobin per red blood cell have been proven to provide clinical benefit in sickle cell anemia and sickle cell disease patients by reducing the frequency of acute vaso-occlusive crises. Additionally, although not clinically proven, the disease biology of beta-thalassemia suggests that increasing fetal hemoglobin production to high levels may be a viable strategy for the therapy of this disease as well.

The object of this therapeutic approach, the de-repression of the silenced HBG1 and HBG2 genes, may be targeted through intervention in an epigenetic process in erythropoiesis. Changes in DNA methylation are key determining events in the course of hematopoiesis, marking differentiation milestones that result in commitments to various cell lineages. During erythropoiesis, a rapid decrease in global DNA methylation demarks a commitment point toward the expression of erythroid specific regulators GATA1 and KLF1, and suppression of hematopoietic progenitor regulators GATA2 and PU.1 (1, 2). For erythroid progenitor cells in adult bone marrow, DNA in the promoter region of the beta-globin HBB gene becomes unmethylated, corresponding to high level expression of beta-globin protein. In contrast, promoters of the HBG1 and HBG2 loci are highly methylated, resulting in greatly diminished expression of gamma-globin proteins (3). Although DNA methyltransferases DNMT1, DNMT3A, and DNMT3B are each expressed in erythroid progenitors, the relatively greater expression of DNMT1, particularly in the final stages of erythroid differentiation suggests that it plays a dominant role in globin gene regulation (2). 5-azacytidine and 5-aza-2'-deoxycytidine (decitabine) are pan-DNMT inhibitors that are known inducers of fetal hemoglobin in erythroid progenitor cells. In erythroid cell culture and in an in vivo model of fetal hemoglobin induction (4, 5), treatment with these agents causes decreased methylation of CpG sites in the HBG promoters with corresponding increases in the gamma globin protein expression. Moreover, in a limited set of clinical studies, both agents caused increases in fetal hemoglobin in patients with sickle cell anemia, sickle cell disease and beta-thalassemia (6-9). While effective at inducing fetal hemoglobin, these agents have not been widely used to treat sickle cell anemia, sickle cell disease, or beta-thalassemia due to concerns over long-term safety, dose-limiting toxicities, and an unsuitable dosing route.

REFERENCES (1) Pop R, Shearstone J R, Shen Q, Liu Y, Hallstrom K, Koulnis M, et al. A key commitment step in erythropoiesis is synchronized with the cell cycle clock through mutual inhibition between PU.1 and S-phase progression. 2010; 8.
(2) Shearstone J R, Pop R, Bock C, Boyle P, Meissner A, Socolovsky M. Global DNA demethylation during mouse erythropoiesis in vivo. 2011; 334:799-802.
(3) Mabaera R, Richardson C A, Johnson K, Hsu M, Fiering S, Lowrey C H. Developmental- and differentiation-specific patterns of human +|- and +|-globin promoter DNA methylation. 2007; 110:1343-52.
(4) Chin J, Singh M, Banzon V, Vaitkus K, Ibanez V, Kouznetsova T, et al. Transcriptional activation of the +|-globin gene in baboons treated with decitabine and in cultured erythroid progenitor cells involves different mechanisms. 2009; 37:1131-42.
(5) Akpan I, Banzon V, Ibanez V, Vaitkus K, DeSimone J, Lavelle D. Decitabine increases fetal hemoglobin in Papio anubis by increasing +|-globin gene transcription. 2010; 38:989-93.
(6) Dover G J, Charache S H, Boyer S H, Talbot J, Smith K D. 5-Azacytidine increases fetal hemoglobin production in a patient with sickle cell disease. 1983; 134:475-88.
(7) Saunthararajah Y, Hillery C A, Lavelle D, Molokie R, Dorn L, Bressler L, et al. Effects of 5-aza-2GÇl-deoxycytidine on fetal hemoglobin levels, red cell adhesion, and hematopoietic differentiation in patients with sickle cell disease. 2003; 102:3865-70
(8) Ley T J, DeSimone J, Noguchi C T, Turner P H, Schechter A N, Heller P, et al. 5-Azacytidine increases +|-globin synthesis and reduces the proportion of dense cells in patients with sickle cell anemia. 1983; 62:370-80.
(9) Lowrey C H, Nienhuis A W. Brief report: Treatment with azacitidine of patients with end-stage +|-thalassemia. 1993; 329:845-8.

It is an object of the invention to provide a novel compound that is an inhibitor of DNMT1.

SUMMARY OF THE INVENTION

The invention is directed to novel compounds.
Specifically, the invention is directed to a compound of formula (I)

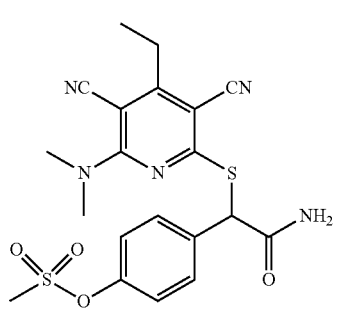

(I)

and prodrugs thereof, and salts thereof.

The invention is further directed to pharmaceutical compositions comprising a compound of formula (I) or prodrug thereof, or a pharmaceutically acceptable salt thereof, and one or more pharmaceutically acceptable excipients.

The invention is further directed to methods of treating diseases associated with inappropriate DNMT1 activity comprising administering a safe and effective amount of a compound of formula (I) or prodrug thereof, or a pharmaceutically acceptable salt thereof, to a patient in need thereof.

The invention is further directed to a compound of formula (I) or prodrug thereof, or a pharmaceutically acceptable salt thereof, for use in medical therapy.

The invention is further directed to a compound of formula (I) or prodrug thereof, or a pharmaceutically acceptable salt thereof, for use in the treatment of a disease associated with inappropriate DNMT1 activity.

The invention is further directed to use of a compound of formula (I) or prodrug thereof, or a pharmaceutically acceptable salt thereof, in the manufacture of a medicament for use in the treatment of a disease associated with inappropriate DNMT1 activity.

The invention is still further directed to a combination comprising a compound of formula (I) or prodrug thereof, or a pharmaceutically acceptable salt thereof, and one or more other therapeutic agents.

DETAILED DESCRIPTION OF THE INVENTION

Figure 1:
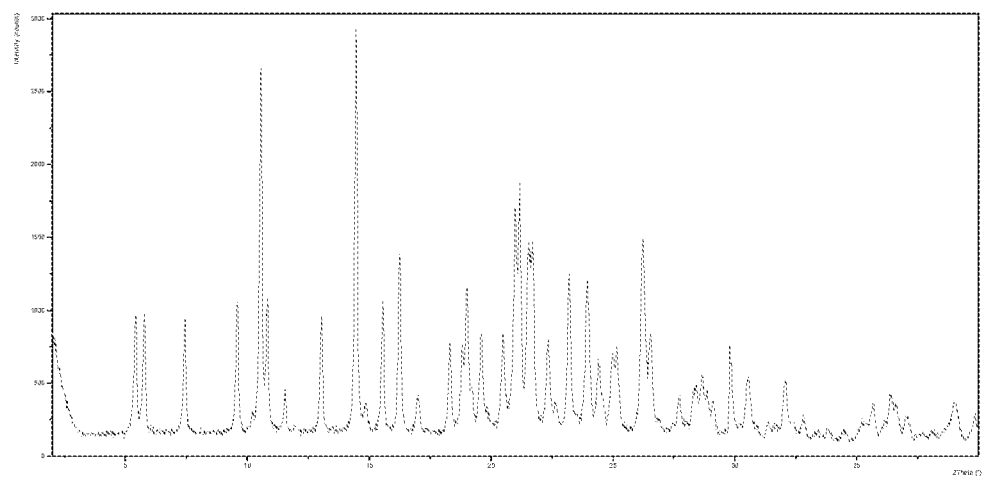
FIG. 1 is an X-Ray Powder Diffraction of the glycinate salt of the Compound of Example 1.

In one embodiment, the invention is directed to a compound of formula (I)

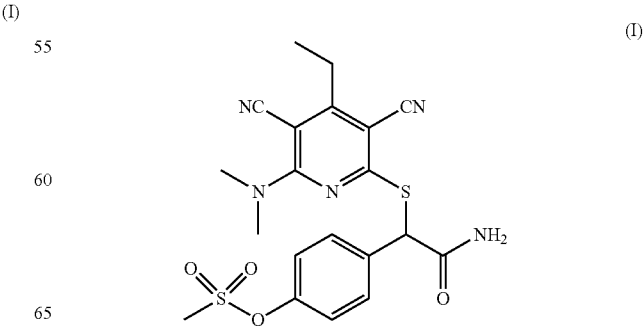

(I)

and prodrugs thereof, and salts thereof (hereinafter "compounds of the invention").

The compounds of the invention contain at least one asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in a compound of the invention, or in any chemical structure illustrated herein, is not specified the structure is intended to encompass any stereoisomer and all mixtures thereof. Thus, compounds of the invention may be used as racemic mixtures, enantiomerically enriched mixtures, or as enantiomerically pure individual stereoisomers.

Thus, in one embodiment, the compound of the invention is a compound of formula (II)

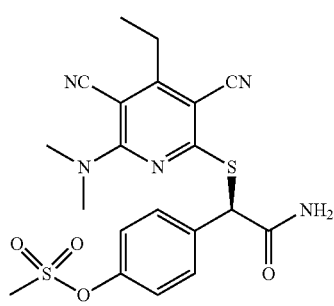

(II)

or a prodrug thereof, or a salt thereof.

In another embodiment, the compound of the invention is a compound of formula (II)

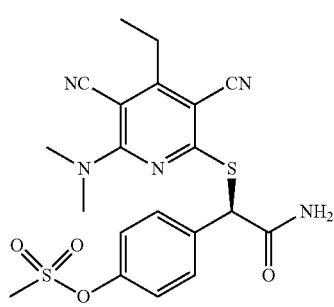

(II)

or a prodrug thereof.

In a further embodiment, the compound of the invention is a compound of formula (III)

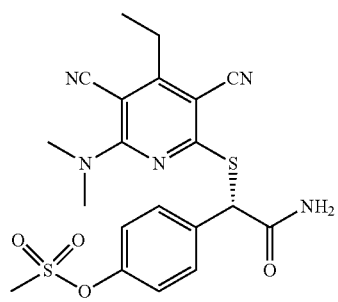 [SMILES: CCc1c(C#N)c(S[C@H](C(N)=O)c2ccc(OS(C)(=O)=O)cc2)nc(N(C)C)c1C#N]

or a prodrug thereof, or a salt thereof.

Individual stereoisomers of a compound of the invention may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds of the invention may also contain centers of geometric asymmetry. Where the stereochemistry of a center of geometric asymmetry present in a compound of the invention, or in any chemical structure illustrated herein, is not specified, the structure is intended to encompass the trans geometric isomer, the cis geometric isomer, and all mixtures thereof. Likewise, all tautomeric forms are also included whether such tautomers exist in equilibrium or predominately in one form.

The compounds of the invention may be administered as prodrugs. As used herein, a "prodrug" of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the solubility of the compound in vivo, (b) modify the onset of the activity of the compound in vivo; (c) modify the duration of action of the compound in vivo; (d) modify the transportation or distribution of the compound in vivo; and (e) overcome a side effect or other difficulty encountered with the compound. Typical functional derivatives used to prepare prodrugs include modifications of the compound that are chemically or enzymatically cleavable in vivo. Such modifications, which include the preparation of phosphates, amides, esters, thioesters, carbonates, and carbamates, are well known to those skilled in the art. In one embodiment, the prodrug moiety is —P(O)(OH)$_2$.

Thus, in one embodiment, the compound of the invention is a prodrug of formula (IV)

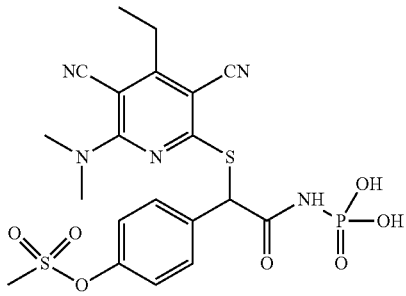

(IV)

or a salt thereof.

In another embodiment, the compound of the invention is the prodrug of formula (V)

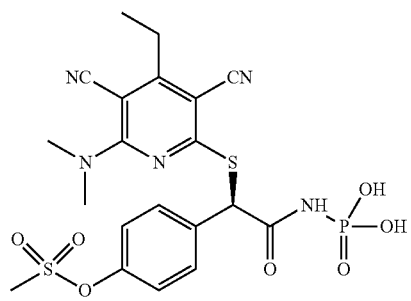

(V)

or a salt thereof.

In another embodiment, the compound of the invention is the prodrug of formula (V)

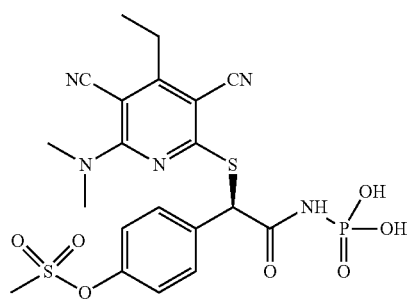

(V)

In a further embodiment, the compound of the invention is the prodrug of formula (VI)

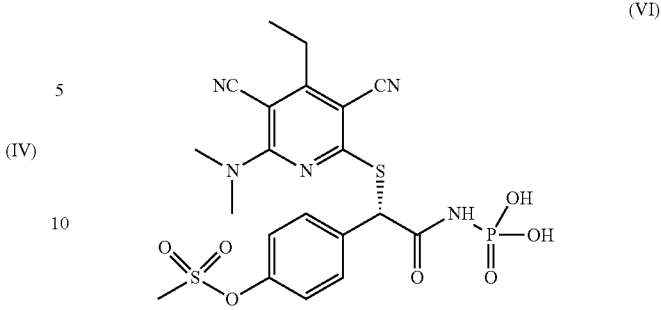

(VI)

or a salt thereof.

It is to be understood that the references herein to a compound of formula (I) and prodrugs thereof, and salts thereof, covers the compound of formula (I) and prodrugs thereof as free acids or free bases, or as salts thereof, for example as pharmaceutically acceptable salts thereof. Thus, in one embodiment, the invention is directed to a compound of formula (I) or a prodrug thereof as the free acid or free base. In another embodiment, the invention is directed to a compound of formula (I) or a prodrug thereof, or a salt thereof. In a further embodiment, the invention is directed to a compound of formula (I) or a prodrug thereof, or a pharmaceutically acceptable salt thereof.

The skilled artisan will appreciate that pharmaceutically acceptable salts of the compounds according to formula (I) or a prodrug thereof may be prepared. Indeed, in certain embodiments of the invention, pharmaceutically acceptable salts of the compound according to formula (I) or a prodrug thereof may be preferred over the respective free base or free acid because such salts may impart greater stability or solubility to the molecule thereby facilitating formulation into a dosage form.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form, or a non-pharmaceutically acceptable salt, with a suitable base or acid, respectively.

Salts and solvates having non-pharmaceutically acceptable counter-ions or associated solvents are within the scope of the invention, for example, for use as intermediates in the preparation of the compound of formula (I) or prodrug thereof and their pharmaceutically acceptable salts. Thus one embodiment of the invention embraces a compound of formula (I) and prodrugs thereof, and salts thereof.

Pharmaceutically acceptable salts include, amongst others, those described in Berge, J. Pharm. Sci., 1977, 66, 1-19, or those listed in P H Stahl and C G Wermuth, editors, Handbook of Pharmaceutical Salts; Properties, Selection and Use, Second Edition Stahl/Wermuth: Wiley-VCH/VHCA, 2011 (see http://www.wiley.com/WileyCDA/WileyTitle/productCd-3906390519.html).

In certain embodiments, a compound according to formula (I) or a prodrug thereof may contain an acidic functional group. Suitable pharmaceutically-acceptable salts include salts of such acidic functional groups. Representative salts include, but are not limited to, aluminium, 2-amino-2-(hydroxymethyl)-1,3-propanediol (TRIS, tromethamine), arginine, benethamine (N-benzylphenethylamine), benzathine (N,N'-dibenzylethylenediamine), bis-(2-hydroxyethyl)amine, bismuth, calcium, chloroprocaine, choline, clemizole (1-p chlorobenzyl-2-pyrrolildine-1'-ylmethylbenzimidazole), cyclohexylamine, dibenzylethylenediamine, diethylamine, diethyltriamine, dimethylamine, dimethylethanolamine, dopamine, ethanolamine, ethylenediamine, L-histidine, iron, isoquinoline, lepidine, lithium, L-lysine, magnesium, meglumine (N-methylglucamine), piperazine, piperidine, potassium, procaine, quinine, quinoline, sodium, strontium, t-butylamine, betaine (tri-methylglycine), L-proline, L-phenylalanine, L-alanine, L-tyrosine, L-leucine, imidazole, glycine, L-valine, L-serine, morpholine, tri-choline, diethyenetriamine, 1-(2-hydroxyethyl)-2-pyrrolildine, and zinc.

Such base addition salts can be formed by reaction of a compound of formula (I) or prodrug thereof (which, for example, contains a carboxylic acid or other acidic functional group) with the appropriate base, optionally in a suitable solvent such as an organic solvent, to give the salt which can be isolated by a variety of methods, including crystallisation and filtration.

It will be understood that if a compound of formula (I) or prodrug thereof contains two or more basic moieties, the stoichiometry of salt formation may include 1, 2 or more equivalents of acid. Such salts would contain 1, 2 or more acid counterions, for example, a dihydrochloride salt.

Stoichiometric and non-stoichiometric forms of a pharmaceutically acceptable salt of a compound of formula (I) or prodrug thereof are included within the scope of the invention, including sub-stoichiometric salts, for example where a counterion contains more than one acidic proton.

In certain embodiments, a compound according to formula (I) or a prodrug thereof may contain a basic functional group and are therefore capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicyclate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

Such acid addition salts can be formed by reaction of a compound of formula (I) or prodrug thereof (which, for example contains a basic amine or other basic functional group) with the appropriate acid, optionally in a suitable solvent such as an organic solvent, to give the salt which can be isolated by a variety of methods, including crystallisation and filtration.

Salts may be prepared in situ during the final isolation and purification of a compound of formula (I) or prodrug thereof. If a basic compound of formula (I) or prodrug thereof is isolated as a salt, the corresponding free base form of that compound may be prepared by any suitable method known to the art, including treatment of the salt with an inorganic or organic base. Similarly, if a compound of formula (I) or prodrug thereof containing a carboxylic acid or other acidic functional group is isolated as a salt, the corresponding free acid form of that compound may be prepared by any suitable method known to the art, including treatment of the salt with an inorganic or organic acid.

Included within the scope of the "compounds of the invention" are all optical isomers, stereoisomers, polymorphs and radiolabelled derivatives of the compounds of formula (I) and prodrugs thereof, and salts thereof.

The compounds of the invention may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. The compounds of the invention may exist in solvated and unsolvated form. Solvates may involve nonaqueous solvents such as ethanol, isopropanol, DMSO, acetic acid, ethanolamine, and EtOAc, or they may involve water as the solvent that is incorporated into the crystalline lattice. Solvates wherein water is the solvent that is incorporated into the crystalline lattice are typically referred to as "hydrates". Hydrates include stoichiometric hydrates as well as compositions containing variable amounts of water.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs". The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The invention also includes isotopically-labelled compounds, which are identical to the compounds of the invention, but for the fact that one or more atoms are replaced by an atom having an atomic mass or mass number different from the atomic mass or mass number most commonly found in nature. Examples of isotopes that can be incorporated into the compounds of the invention include isotopes of hydrogen, carbon, nitrogen, oxygen and fluorine, such as $^{2}H$, $^{3}H$, $^{11}C$, $^{14}C$ and $^{18}F$.

"Enantiomerically enriched" refers to products whose enantiomeric excess is greater than zero. For example, enantiomerically enriched refers to products whose enantiomeric excess is greater than 50% ee, greater than 75% ee, and greater than 90% ee.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%). In some embodiments, the compounds of the invention may have at least 50% ee, at least 60% ee, at least 65% ee, at least 70% ee, at least 75% ee, at least 80% ee, at least 85% ee, at least 90% ee, at least 95% ee, at least 96% ee, at least 97% ee, at least 98% ee, or at least 99% ee with respect to either the R or S enantiomer.

"Enantiomerically pure" refers to products whose enantiomeric excess is 99% ee or greater.

"Pharmaceutically acceptable" refers to those compounds, salts, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The compounds of the invention are useful as selective DNMT1 inhibitors in mammals, particularly humans, in need thereof. Compounds which are DNMT1 inhibitors may be useful in the treatment of diseases wherein the underlying pathology is (at least in part) attributable to inappropriate DNMT1 activity, such as cancer. "Inappropriate DNMT1 activity" refers to any DNMT1 activity that deviates from the normal DNMT1 activity expected in a particular patient. Inappropriate DNMT1 may take the form of, for instance, an abnormal increase in activity, or an aberration in the timing and or control of DNMT1 activity. Accordingly, in another aspect the invention is directed to methods of treating such diseases.

In some aspects of the invention, the compound of formula (I) and prodrugs thereof, and salts thereof, are potent inhibitors of DNMT1 and are selective for DNMT1 over DNMT3A and DNMT3B.

Such diseases include cancer, a pre-cancerous syndrome (sometimes referred to as pre-cancerous condition), or a beta haemoglobinopathy disorder. A precancerous condition is a condition or lesion involving abnormal cells which are associated with an increased risk of developing into cancer. Clinically, precancerous conditions encompass a variety of conditions or lesions with an increased risk of developing into cancer.

Cancers that may be treated include: adenocarcinoma, basal cell carcinoma, squamous cell carcinoma, adenosquamous carcinoma, carcinosarcoma, melanoma, adrenal gland cancer, adrenocortical carcinoma, pheochromocytoma, breast cancer, ductal carcinoma in situ, lobular carcinoma, inflammatory breast cancer, invasive ductal carcinoma, Paget disease of the nipple, papillary breast cancer, medullary carcinoma, mammary carcinoma, anal cancer, cloacogenic carcinoma, anorectal melanoma, appendiceal cancer, appendiceal neuroendocrine tumour, appendiceal mucinous cystadenocarcinomas, colonic-type adenocarcinoma, signet-ring cell adenocarcinoma, goblet cell carcinomas/adenoneuroendocrine carcinomas, bile duct cancer, intrahepatic cholangiocarcinoma, extrahepatic cholangiocarcinoma, perihilar cholangiocarcinoma, distal extrahepatic cholangiocarcinoma, colorectal cancer (CRC), mucinous adenocarcinoma, gastrointestinal carcinoid tumours, gastrointestinal stromal tumours, primary colorectal lymphomas, leiomyosarcoma, esophageal cancer, small cell carcinoma, leiomyoma, gallbladder cancer, non-papillary adenocarcinoma, papillary adenocarcinoma, stomach cancer, gastric adenocarcinoma, liver cancer, hepatocellular carcinoma, fibrolamellar carcinoma, angiosarcoma, lymphangiosarcoma, hemangiosarcoma, hepatoblastoma, pancreatic cancer, ductal adenocarcinoma, acinar adenocarcinoma, acinar cell carcinoma, colloid carcinoma, giant cell tumour, hepatoid carcinoma, mucinous cystic neoplasms, pancreatoblastoma, serous cystadenoma, intraductal papillary mucinous neoplasm, pancreatic neuroendocrine tumour, gastrinoma, insulinoma, glucagonoma, VIPoma, somatostatinoma, PPoma, small intestine cancer, eye cancer, intraocular melanoma, intraocular lymphoma, intraocular retinoblastoma, conjunctival melanoma, eyelid carcinoma, sebaceous carcinoma, lacrimal gland tumour, malignant mixed epithelial tumour, adenoid cystic carcinoma, bladder cancer, urothelial carcinoma, kidney cancer, renal cell carcinoma (RCC), clear cell RCC, papillary RCC, chromophobe RCC, collecting duct RCC, multilocular cystic RCC, renal mucinous tubular and spindle cell carcinoma, tubulocystic RCC, thyroid-like follicular RCC, acquired cystic kidney disease-associated RCC, RCC with t(6;11) translocation (TFEB), hybrid oncocytoma/chromophobe RCC, Wilms tumor, penile cancer, prostate cancer, castration-resistant prostate cancer, transitional cell carcinoma, testicular cancer, seminoma, classical seminoma, spermatocytic seminoma, non-seminoma, embryonal carcinoma, yolk sac carcinoma, choriocarcinoma, teratoma, Leydig cell tumours, Sertoli cell tumours, carcinoma of the rete testis, urethral cancer, extracranial germ cell tumour, germinoma, gonadoblastoma, mixed germ cell tumour, extragonadal germ cell tumour, endodermal sinus tumours, cervical cancer, endometrial cancer, ovarian cancer, fallopian tube cancer, epithelial carcinoma, dysgerminoma, sex cord stromal tumours, gestational trophoblastic tumour, primary peritoneal cancer, uterine sarcoma, uterine papillary serous carcinoma, vaginal cancer, clear cell adenocarcinoma, vulvar cancer, verrucous carcinoma, head and neck cancer, head and neck squamous cell carcinoma, pharyngeal cancer, hypopharyngeal cancer, nasopharyngeal cancer, oropharyngeal cancer, non-keratinising squamous cell carcinoma, undifferentiated carcinoma, laryngeal cancer, oral cavity cancer, mouth cancer, mucoepidermoid carcinoma, paranasal sinus and nasal cavity cancer, esthesioneuroblastoma, salivary gland cancer, epithelial-myoepithelial carcinoma, parathyroid cancer, thyroid cancer, papillary thyroid carcinoma, follicular thyroid carcinoma, Hurthle cell carcinoma, medullary thyroid carcinoma, anaplastic thyroid carcinoma, paraganglioma, carotid paraganglioma, jugulotympanic paraganglioma, vagal paraganglioma, leukemia, acute lymphoblastic leukemia, T-lymphoblastic leukemia, precursor B-cell lymphoblastic leukemia, acute myeloid leukemia (AML), acute myelogenous leukemia, acute promyelocytic leukemia, acute myelomonocytic leukemia, acute monocytic leukemia, acute megakaryoblastic leukemia, erythroleukemia, chronic lymphocytic leukemia, B-cell chronic lymphocytic leukemia, B-cell prolymphocytic leukemia, T-cell prolymphocytic leukemia, large granular lymphocytic leukemia, T-cell large granular lymphocytic leukemia, NK-cell granular lymphocytic leukemia, hairy cell leukemia, chronic myelogenous leukemia, chronic myelomonocytic leukemia, chronic neutrophilic leukemia, chronic eosinophilic leukemia, plasma cell leukemia, lymphoma, Hodgkin's lymphoma, classical Hodgkin's lymphoma, nodular sclerosing classical Hodgkin's lymphoma, mixed cellularity classical Hodgkin's lymphoma, lymphocyte-rich classical Hodgkin's lymphoma, lymphocyte-depleted classical Hodgkin's lymphoma, nodular lymphocyte-predominant Hodgkin's lymphoma, non-Hodgkin's lymphoma (NHL), diffuse large B-cell lymphoma, primary mediastinal B-cell lymphoma, primary effusion lymphoma, T-cell/histiocyte-rich large B-cell lymphoma, lymphoplasmacytic lymphoma, lymphoblastic lymphoma, small lymphocytic lymphoma, double hit/triple hit lymphoma, Burkitt lymphoma, Burkitt-like lymphoma, small non-cleaved cell lymphoma, follicular lymphoma, follicular large-cell lymphoma, immunoblastic lymphoma, intravascular large-cell lymphoma, primary splenic lymphoma, anaplastic large-cell lymphoma, mantle cell lymphoma, marginal zone lymphoma (MZL), extranodal MZL, nodal MZL, splenic MZL, splenic MZL with villous lymphocytes, peripheral T-cell lymphoma, angioimmunoblastic T-cell lymphoma, adult T-cell lymphoma/leukemia, extranodal NK/T-cell lymphoma, enteropathy-associated T-cell lymphoma, hepatosplenic T-cell lymphoma, subcutaneous panniculitis-like T-cell lymphoma, T-cell non-Hodgkin's lymphoma not otherwise specified, gamma/delta T-cell lymphoma, mucosa-associated-lymphoid tissue lymphoma, post-transplant lymphoproliferative disorder, HIV-associated lymphoma, Langerhans cell histiocytosis, multiple myeloma, smoldering multiple myeloma, active multiple myeloma, plasmacytoma, solitary plasmacytoma of bone, extramedullary plasmacytoma, primary amyloidosis, myelodysplastic syndromes (MDS), refractory anaemia, refractory anaemia with ring sideroblasts, refractory anaemia with excess blasts, refractory anaemia with excess blasts in transformation, myeloproliferative neoplasms, polycythemia vera, essential thrombocythemia, myelofibrosis, systemic mastocytosis, bone cancer, Ewing sarcoma, osteosarcoma, intramedullary osteosarcoma, juxtacortical osteosarcoma, extraskeletal osteosarcoma, malignant fibrous histiocytoma of bone, chordoma, classic chordoma, chondroid chordoma, dedifferentiated chordoma, chondrosarcoma, conventional chondrosarcoma, clear cell chondrosarcoma, myxoid chondrosarcoma, mesenchymal chondrosarcoma, dedifferentiated chondrosarcoma, rhabdomyosarcoma, embryonal rhabdomyosarcoma, alveolar rhabdomyosarcoma, botryoid rhabdomyosarcoma, pleomorphic rhabdomyosarcoma, soft tissue sarcoma, extraosseus sarcoma, dermatofibrosarcoma protuberans, epithelioid sarcoma, Kaposi's sarcoma, liposarcoma, malignant peripheral nerve sheath tumour, fibrosarcoma, myxosarcoma, synovioma, brain cancer, anaplastic astrocytoma, glioblastoma, glioblastoma multiforme, meningioma, pituitary carcinoma, schwannoma, oligodendroglioma, ependymoma, medulloblastoma, astrocytoma, brainstem glioma, atypical teratoid/rhabdoid tumour, pinealoma, neuroblastoma, primary CNS lymphoma, primitive neuroectodermal tumour, diffuse intrinsic pontine glioma, lung cancer, non-small cell lung cancer (NSCLC), NSCLC undifferentiated, small cell lung cancer, pleuropulmonary blastoma, bronchogenic carcinoma, malignant mesothelioma, malignant pleural mesothelioma, malignant peritoneal mesothelioma, thymoma, thymic carcinoma, skin cancer, keratoacanthoma, sebaceous gland carcinoma, sweat gland adenocarcinoma, apocrine carcinoma, eccrine carcinoma, clear cell eccrine carcinoma, Merkel cell carcinoma, cutaneous T cell lymphoma, mycosis fungoides, Sézary syndrome, chondroid syringoma, HPV-associated cancers, tumours containing transformed cells, tumours containing cells in precancerous states, precancerous hyperplasia, precancerous metaplasia, precancerous dysplasia, carcinoma in situ, mixed tumour, malignant mixed tumour, and complex carcinoma.

Cancers that may be treated also include cancers having a high tumour mutational burden (TMB), a defective DNA mismatch repair system (dMMR), a high microsatellite instability status (MSI-H), low microsatellite instability status (MSI-L), elevated microsatellite alterations at selected tetranucleotide repeats (EMAST), microsatellite stable (MSS) cancers, cancers comprising mutations in polymerase delta (POLD), cancers comprising mutations in polymerase epsilon (POLE), or cancers with homologous recombination repair deficiency (HRD).

Cancers that may be treated further include breast cancers defined by expression profiling (triple-negative breast cancer, HER2 positive breast cancer, luminal A breast cancer, luminal B breast cancer, normal-like breast cancer) or breast cancers with BRCA1 or BRCA2 mutations.

In one embodiment of the invention, the cancer treated is myelodysplastic syndrome (MDS), acute myeloid leukemia (AML), colorectal cancer (CRC), non-Hodgkin's lymphoma (NHL), melanoma or breast cancer. In another embodiment of the invention, the cancer is acute myeloid leukemia (AML). In a further embodiment of the invention, the cancer is colorectal cancer (CRC).

The methods of treatment of the invention comprise administering a safe and effective amount of a compound of formula (I) or prodrug thereof, or a pharmaceutically acceptable salt thereof, to a patient in need thereof. Individual embodiments of the invention include methods of treating any one of the above-mentioned disorders by administering a safe and effective amount of a compound of formula (I) or a prodrug thereof, or a pharmaceutically acceptable salt thereof, to a patient in need thereof.

As used herein, "treat" in reference to a disorder means: (1) to ameliorate or prevent the disorder or one or more of the biological manifestations of the disorder, (2) to interfere with (a) one or more points in the biological cascade that leads to or is responsible for the disorder or (b) one or more of the biological manifestations of the disorder, (3) to alleviate one or more of the symptoms or effects associated with the disorder, or (4) to slow the progression of the disorder or one or more of the biological manifestations of the disorder.

As used herein, "safe and effective amount" in reference to a compound of formula (I) or a prodrug thereof, or a pharmaceutically acceptable salt thereof, or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the disorder being treated; the severity of the disorder being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human (including adults and children) or other animal. In one embodiment, "patient" refers to a human.

The invention thus is directed to methods of treating diseases associated with inappropriate DNMT1 activity comprising administering a safe and effective amount of a compound of formula (I) or prodrug thereof, or a pharmaceutically acceptable salt thereof, to a patient in need thereof.

In one embodiment, the invention provides a method of treating cancer, a pre-cancerous syndrome, or a beta haemoglobinopathy disorder comprising administering a safe and effective amount of a compound of formula (I) or prodrug thereof, or a pharmaceutically acceptable salt thereof, to a patient in need thereof.

In another embodiment, the invention provides a method of treating cancer, a pre-cancerous syndrome, or a beta haemoglobinopathy disorder comprising administering a safe and effective amount of a compound of formula (I) or prodrug thereof, or a pharmaceutically acceptable salt thereof, to a patient in need thereof.

In another embodiment, the invention provides a method of treating myelodysplastic syndrome (MDS), acute myeloid leukemia (AML), colorectal cancer (CRC), non-Hodgkin's lymphoma (NHL), melanoma or breast cancer comprising administering a safe and effective amount of a compound of formula (I) or prodrug thereof, or a pharmaceutically acceptable salt thereof, to a patient in need thereof.

In another embodiment, the invention provides a method of treating acute myeloid leukemia (AML) comprising administering a safe and effective amount of a compound of formula (I) or prodrug thereof, or a pharmaceutically acceptable salt thereof, to a patient in need thereof.

In another embodiment, the invention provides a method of treating colorectal cancer (CRC) comprising administering a safe and effective amount of a compound of formula (I) or prodrug thereof, or a pharmaceutically acceptable salt thereof, to a patient in need thereof.

In a further embodiment, the invention provides a method of treating sickle cell disease, sickle cell anemia or beta thalassemia comprising administering a safe and effective amount of a compound of formula (I) or prodrug thereof, or a pharmaceutically acceptable salt thereof, to a patient in need thereof. Sickle cell anemia is a single specific disease characterized by a homozygous E6V mutation in both of the beta globin gene alleles. In contrast, sickle cell disease is an aggregation of several related diseases, all presenting with similar symptoms of varying severity. Sickle cell disease patients have one beta globin gene allele with the E6V mutation (as per sickle cell anemia), with the second beta globin gene allele carrying any number of mutations but especially mutations causing beta thalassemia. The most common sickle cell disease manifestations are called 'sickle beta zero', and 'sickle beta plus', but there are others as well. Note that the second beta globin allele in sickle cell disease patients is not free of mutations (one E6V beta globin allele plus one normal beta globin allele is known as sickle cell trait, which is not totally benign but is generally not treated), but just that the mutations in the second allele are not the E6V mutation. Note that sickle cell trait is not considered to be sickle cell disease.

The invention is further directed to a compound of formula (I) or prodrug thereof, or a pharmaceutically acceptable salt thereof, for use in medical therapy.

The invention is further directed to a compound of formula (I) or prodrug thereof, or a pharmaceutically acceptable salt thereof, for use in the treatment of a disease associated with inappropriate DNMT1 activity.

The invention is still further directed to use of a compound of formula (I) or prodrug thereof, or a pharmaceutically acceptable salt thereof, in the manufacture of a medicament for use in the treatment of a disease associated with inappropriate DNMT1 activity.

The compounds of formula (I) and prodrugs thereof, and pharmaceutically acceptable salts thereof, will normally, but not necessarily, be formulated into pharmaceutical compositions prior to administration to a patient.

Accordingly, in one aspect the invention is directed to pharmaceutical compositions comprising a compound of formula (I) or a prodrug thereof, or a pharmaceutically acceptable salt thereof, and one or more pharmaceutically acceptable excipients.

In another aspect the invention is directed to pharmaceutical compositions comprising 0.5 to 3500 mg of a compound of formula (I) or a prodrug thereof, or a pharmaceutically acceptable salt thereof, and 0.1 to 2 g of one or more pharmaceutically acceptable excipients.

In a further aspect the invention is directed to a pharmaceutical composition for the treatment of a disease mediated by inappropriate DNMT1 activity comprising a compound of formula (I) or a prodrug thereof, or a pharmaceutically acceptable salt thereof.

A compound of formula (I) or a prodrug thereof, or pharmaceutically acceptable salts thereof, may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, otic, intravaginal, inhaled and intranasal administration. Inhalation refers to administration into the patient's lungs whether inhaled through the mouth or through the nasal passages. In one embodiment, a compound of formula (I) or prodrug thereof, or pharmaceutically acceptable salts thereof, may be administered orally.

In some embodiments, certain prodrugs of the compound of formula (I) may be particularly suitable for oral administration due to improved solubility which leads to increased oral bioavailability.

A compound of formula (I) or a prodrug thereof, or pharmaceutically acceptable salts thereof, may be administered once or according to a dosing regimen wherein a number of doses are administered at varying intervals of time for a given period of time. For example, doses may be administered one, two, three, four, five or six times per day. Doses may be administered until the desired therapeutic effect is achieved or indefinitely to maintain the desired therapeutic effect. Suitable dosing regimens for a compound of formula (I) or prodrug thereof, or a pharmaceutically acceptable salt thereof, depend on the pharmacokinetic properties of that compound, such as absorption, distribution, and half-life, which can be determined by the skilled artisan. In addition, suitable dosing regimens, including the duration such regimens are administered, for a compound of formula (I) or prodrug thereof, or a pharmaceutically acceptable salt thereof depend on the disorder being treated, the severity of the disease being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change. Doses of the invented pharmaceutically active compounds in a pharmaceutical dosage unit as described above will be an efficacious, non-toxic quantity preferably selected from the range of 0.001-500 mg/kg of active compound, preferably 0.01-100 mg/kg. When treating a human patient in need of a DNMT1 inhibitor, the selected dose is administered preferably from 1-6 times daily, orally or parenterally. Preferred forms of parenteral administration include topically, rectally, transdermally, by injection and continuously by infusion. Oral dosage units for human administration preferably contain from 0.5 to 3500 mg of active compound. Suitably oral dosage units for human administration preferably contain from 0.5 to 1,000 mg of active compound. Oral administration, which uses lower dosages, is preferred. Parenteral administration, at high dosages, however, also can be used when safe and convenient for the patient.

The compounds of formula (I) and pharmaceutically acceptable salts thereof will normally, but not necessarily, be formulated into pharmaceutical compositions prior to administration to a patient.

Accordingly, in one aspect the invention is directed to pharmaceutical compositions comprising a compound of formula (I) or a pharmaceutically acceptable salt thereof and one or more pharmaceutically acceptable excipients.

In another aspect the invention is directed to pharmaceutical compositions comprising 0.05 to 1000 mg of a compound of formula (I) or a pharmaceutically acceptable salt thereof and 0.1 to 2 g of one or more pharmaceutically acceptable excipients.

In a further aspect the invention is directed to a pharmaceutical composition for the treatment or prophylaxis of a disorder mediated by inappropriate DNMT1 activity comprising a compound of formula (I) or a pharmaceutically acceptable salt thereof.

The pharmaceutical compositions of the invention may be prepared and packaged in bulk form wherein a safe and effective amount of a compound of formula (I) or a pharmaceutically acceptable salt thereof can be extracted and then given to the patient such as with powders or syrups. Alternatively, the pharmaceutical compositions of the invention may be prepared and packaged in unit dosage form wherein each physically discrete unit contains a compound of formula (I) or a pharmaceutically acceptable salt thereof. When prepared in unit dosage form, the pharmaceutical compositions of the invention typically may contain, for example, from 0.5 to 1,000 mg, or from 1 mg to 700 mg, or from 5 mg to 100 mg of a compound of formula (I) or prodrug thereof, or a pharmaceutically acceptable salt thereof.

The pharmaceutical compositions of the invention typically contain one compound of formula (I) or prodrug thereof, or a pharmaceutically acceptable salt thereof.

As used herein, "pharmaceutically acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of formula (I) or prodrug thereof, or a pharmaceutically acceptable salt thereof, when administered to a patient and interactions which would result in pharmaceutical compositions that are not pharmaceutically acceptable are avoided. In addition, each excipient must of course be pharmaceutically-acceptable eg of sufficiently high purity.

The compound of formula (I) or prodrug thereof, or a pharmaceutically acceptable salt thereof, and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of a compound of formula (I) or prodrug thereof, or pharmaceutically acceptable salts thereof, once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The pharmaceutical compositions of the invention are prepared using techniques and methods known to those skilled in the art. Some of the methods commonly used in the art are described in Remington's Pharmaceutical Sciences (Mack Publishing Company).

Accordingly, in another aspect the invention is directed to process for the preparation of a pharmaceutical composition comprising a compound of formula (I) or a prodrug thereof, or a pharmaceutically acceptable salt thereof, and one or more pharmaceutically acceptable excipients which comprises mixing the ingredients. A pharmaceutical composition comprising a compound of formula (I) or a prodrug thereof, or a pharmaceutically acceptable salt thereof, may be prepared by, for example, admixture at ambient temperature and atmospheric pressure.

In one embodiment, the compounds of formula (I) or a prodrug thereof, or pharmaceutically acceptable salts thereof, will be formulated for oral administration. In a further embodiment, the compounds of formula (I) or a prodrug thereof, or pharmaceutically acceptable salts thereof, will be formulated for parenteral administration.

In one aspect, the invention is directed to a solid oral dosage form such as a tablet or capsule comprising a safe and effective amount of a compound of formula (I) or a prodrug thereof, or a pharmaceutically acceptable salt thereof, and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as for example by coating or embedding particulate material in polymers, wax or the like.

A compound of formula (I) or a prodrug thereof, or a pharmaceutically acceptable salt thereof, may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, a compound of formula (I) or a prodrug thereof, or a pharmaceutically acceptable salt thereof, may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

In another aspect, the invention is directed to a liquid oral dosage form. Oral liquids such as solution, syrups and elixirs can be prepared in dosage unit form so that a given quantity contains a predetermined amount of a compound of formula (I) or a prodrug thereof, or a pharmaceutically acceptable salt thereof. Syrups can be prepared by dissolving a compound of formula (I) or a prodrug thereof, or a pharmaceutically acceptable salt thereof, in a suitably flavored aqueous solution, while elixirs are prepared through the use of a non-toxic alcoholic vehicle. Suspensions can be formulated by dispersing a compound of formula (I) or a prodrug thereof, or a pharmaceutically acceptable salt thereof, in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

A compound of formula (I) or prodrug thereof, or a pharmaceutically acceptable salt thereof, may be co-administered with one or more other active agents. Thus, in one embodiment, the invention provides a combination comprising a compound of formula (I) or prodrug thereof, or a pharmaceutically acceptable salt thereof, and one or more other active agents. In a further embodiment, the other active agent(s) are known to be useful in the treatment of cancer or pre-cancerous syndromes.

By the term "co-administration" as used herein is meant either simultaneous administration or any manner of separate sequential administration of an inhibitor of the activity of DMNT1, as described herein, and a further active agent or agents, known to be useful in the treatment of cancer, including chemotherapy and radiation treatment. The terms further "active ingredient", "active ingredients", "active agent" or "active agents", as used herein, includes any compound or therapeutic agent known to or that demonstrates advantageous properties when administered to a patient. Preferably, if the administration is not simultaneous, the compounds are administered in a close time proximity to each other. Furthermore, it does not matter if the compounds are administered in the same dosage form, e.g. one compound may be administered by injection and another compound may be administered orally.

Typically, any anti-neoplastic agent that has activity versus a susceptible tumor being treated may be co-administered in the treatment of cancer in the invention. Examples of such agents can be found in Cancer Principles and Practice of Oncology by V. T. Devita, T. S. Lawrence, and S. A. Rosenberg (editors), $10^{th}$ edition (Dec. 5, 2014), Lippincott Williams & Wilkins Publishers. A person of ordinary skill in the art would be able to discern which combinations of agents would be useful based on the particular characteristics of the drugs and the cancer involved. Typical anti-neoplastic agents useful in the invention include, but are not limited to, anti-microtubule or anti-mitotic agents;

platinum coordination complexes; alkylating agents; antibiotic agents; topoisomerase I inhibitors; topoisomerase II inhibitors; antimetabolites; hormones and hormonal analogues; signal transduction pathway inhibitors; non-receptor tyrosine kinase angiogenesis inhibitors; immunotherapeutic agents; proapoptotic agents; cell cycle signalling inhibitors; proteasome inhibitors; heat shock protein inhibitors; inhibitors of cancer metabolism; and cancer gene therapy agents.

Examples of a further active ingredient or ingredients for use in combination or co-administered with the compound of formula (I) or prodrug thereof, or a pharmaceutically acceptable salt thereof, are anti-neoplastic agents. Examples of anti-neoplastic agents include, but are not limited to, chemotherapeutic agents; immuno-modulatory agents; immune-modulators; and immunostimulatory adjuvants.

Anti-microtubule or anti-mitotic agents are phase specific agents active against the microtubules of tumor cells during M or the mitosis phase of the cell cycle. Examples of anti-microtubule agents include, but are not limited to, diterpenoids and *vinca* alkaloids.

Platinum coordination complexes are non-phase specific anti-cancer agents, which are interactive with DNA. The platinum complexes enter tumor cells, undergo aquation, and form intra- and interstrand crosslinks with DNA causing adverse biological effects to the tumor. Examples of platinum coordination complexes include, but are not limited to, cisplatin and carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Antibiotic anti-neoplastics are non-phase specific agents, which bind or intercalate with DNA. This action disrupts the ordinary function of the nucleic acids, leading to cell death. Examples of antibiotic anti-neoplastic agents include, but are not limited to, actinomycins such as dactinomycin; anthrocyclins such as daunorubicin and doxorubicin; and bleomycins.

Topoisomerase I inhibitors include, but are not limited to, camptothecins. The cytotoxic activity of camptothecins is believed to be related to its topoisomerase I inhibitory activity.

Topoisomerase II inhibitors include, but are not limited to, epipodophyllotoxins. Epipodophyllotoxins are phase specific anti-neoplastic agents derived from the mandrake plant. Epipodophyllotoxins typically affect cells in the S and G2 phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone; aminoglutethimide and other aromatase inhibitors such as anastrozole, letrazole, vorazole, and exemestane; progestrins such as megestrol acetate; estrogens, androgens, and anti-androgens such as flutamide, nilutamide, bicalutamide, cyproterone acetate and 5α-reductases such as finasteride and dutasteride; anti-estrogens such as tamoxifen, toremifene, raloxifene, droloxifene, iodoxyfene, as well as selective estrogen receptor modulators (SERMS); and gonadotropin-releasing hormone (GnRH) and analogues thereof, which stimulate the release of leutinizing hormone (LH) and/or follicle stimulating hormone (FSH), LHRH agonists, and antagonists such as goserelin acetate and leuprolide.

Signal transduction pathway inhibitors are those inhibitors, which block or inhibit a chemical process which evokes an intracellular change. As used herein, this change is cell proliferation or differentiation. Signal transduction inhibitors useful in the invention include, but are not limited to, inhibitors of receptor tyrosine kinases, non-receptor tyrosine kinases, SH2/SH3domain blockers, serine/threonine kinases, phosphatidyl inositol-3 kinases, myo-inositol signalling, and Ras oncogenes.

Several protein tyrosine kinases catalyze the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFR), tyrosine kinase with immunoglobulin-like and epidermal growth factor homology domains (TIE-2), insulin growth factor-I (IGFI) receptor, macrophage colony stimulating factor Cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath J. C., Exp. Opin. Ther. Patents, 10(6):803-818 (2000); Shawver L. K., et al., Drug Discov. Today, 2(2): 50-63 (1997); and Lofts, F. J. and Gullick W. J., "Growth factor receptors as targets." in New Molecular Targets for Cancer Chemotherapy, Kerr D. J. and Workman P. (editors), (Jun. 27, 1994), CRC Press. Non-limiting examples of growth factor receptor inhibitors include pazopanib and sorafenib.

Tyrosine kinases, which are not growth factor receptor kinases, are termed non-receptor tyrosine kinases. Non-receptor tyrosine kinases useful in the invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinha S. and Corey S. J., J. Hematother. Stem Cell Res., 8(5): 465-480 (2004) and Bolen, J. B., Brugge, J. S., Annu. Rev. Immunol., 15: 371-404 (1997).

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall T. E., J. Pharmacol. Toxicol. Methods, 34(3): 125-32 (1995).

Inhibitors of serine/threonine kinases include, but are not limited to, MAP kinase cascade blockers which include blockers of Raf kinases (rafk), Mitogen or Extracellular Regulated Kinase (MEKs), and Extracellular Regulated Kinases (ERKs); Protein kinase C family member blockers including blockers of PKCs (alpha, beta, gamma, epsilon, mu, lambda, iota, zeta); IkB kinases (IKKa, IKKb); PKB family kinases; AKT kinase family members; TGF beta receptor kinases; and mammaliam target of rapamycin (mTOR) inhibitors, including, but not limited to rapamycin (FK506) and rapalogs, RAD001 or everolimus (AFINITOR®), CCI-779 or temsirolimus, AP23573, AZD8055, WYE-354, WYE-600, WYE-687 and Pp121. Examples of inhibitors of serine/threonine kinases include, but are not limited to, trametinib, dabrafenib, and Akt inhibitors afuresertib and N-{(1S)-2-amino-1-[(3,4-difluorophenyl)methyl] ethyl}-5-chloro-4-(4-chloro-1-methyl-1H-pyrazol-5-yl)-2-furancarboxamide.

Inhibitors of phosphatidyl inositol 3-kinase family members including blockers of PI3-kinase, ATM, DNA-PK, and Ku are also useful in the invention. Such kinases are discussed in Abraham R. T., Curr. Opin. Immunol., 8(3): 412-418 (1996); Canman C. E., and Lim D. S., Oncogene, 17(25): 3301-3308 (1998); Jackson S. P., Int. J. Biochem. Cell Biol., 29(7): 935-938 (1997); and Zhong H., et al., Cancer Res., 60(6): 1541-1545 (2000).

Also useful in the invention are myo-inositol signalling inhibitors such as phospholipase C blockers and myo-inositol analogs. Such signal inhibitors are described in Powis G., and Kozikowski A., "Inhibitors of Myo-Inositol Signaling." in New Molecular Targets for Cancer Chemotherapy, Kerr D. J. and Workman P. (editors), (Jun. 27, 1994), CRC Press.

Another group of signal transduction pathway inhibitors are inhibitors of Ras oncogene. Such inhibitors include inhibitors of farnesyltransferase, geranyl-geranyl transferase, and CAAX proteases as well as anti-sense oligonucleotides, ribozymes and other immunotherapies. Such inhibitors have been shown to block ras activation in cells containing wild type mutant ras, thereby acting as antiproliferation agents. Ras oncogene inhibition is discussed in Scharovsky O. G., et al., J. Biomed. Sci., 7(4): 292-298 (2000); Ashby M. N., Curr. Opin. Lipidol., 9(2): 99-102 (1998); and Bennett C. F. and Cowsert L. M., Biochim. Biophys. Acta., 1489(1): 19-30 (1999).

Antagonists to receptor kinase ligand binding may also serve as signal transduction inhibitors. This group of signal transduction pathway inhibitors includes the use of humanized antibodies or other antagonists to the extracellular ligand binding domain of receptor tyrosine kinases. Examples of antibody or other antagonists to receptor kinase ligand binding include, but are not limited to, cetuximab (ERBITUX®), trastuzumab (HERCEPTIN®); trastuzumab emtansine (KADCYLA®); pertuzumab (PERJETA®); ErbB inhibitors including lapatinib, erlotinib, and gefitinib; and 2C3 VEGFR2 specific antibody (see Brekken R. A., et al., Cancer Res., 60(18): 5117-5124 (2000)).

Non-receptor kinase angiogenesis inhibitors may also find use in the invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Accordingly, non-receptor tyrosine kinase inhibitors may be used in combination with the EGFR/erbB2 inhibitors of the invention. For example, anti-VEGF antibodies, which do not recognize VEGFR (the receptor tyrosine kinase), but bind to the ligand; small molecule inhibitors of integrin (alpha betas) that will inhibit angiogenesis; endostatin and angiostatin (non-RTK) may also prove useful in combination with the disclosed compounds. (See Bruns C. J., et al., Cancer Res., 60(11): 2926-2935 (2000); Schreiber A. B., et al., Science, 232(4755): 1250-1253 (1986); Yen L., et al., Oncogene, 19(31): 3460-3469 (2000)).

Agents used in immunotherapeutic regimens may also be useful in combination with the invention. There are a number of immunologic strategies to generate an immune response against erbB2 or EGFR. These strategies are generally in the realm of tumor vaccinations. The efficacy of immunologic approaches may be greatly enhanced through combined inhibition of erbB2/EGFR signaling pathways using a small molecule inhibitor. Discussion of the immunologic/tumor vaccine approach against erbB2/EGFR are found in Reilly R. T., et al., Cancer Res., 60(13): 3569-3576 (2000); and Chen Y., et al., Cancer Res., 58(9): 1965-1971 (1998).

Agents used in proapoptotic regimens (e.g., Bcl-2 antisense oligonucleotides) may also be used in the combination of the invention. Members of the Bcl-2 family of proteins block apoptosis. Upregulation of Bcl-2 has therefore been linked to chemoresistance. Studies have shown that the epidermal growth factor (EGF) stimulates anti-apoptotic members of the Bcl-2 family (i.e., Mcl-1). Therefore, strategies designed to downregulate the expression of Bcl-2 in tumors have demonstrated clinical benefit. Such proapoptotic strategies using the antisense oligonucleotide strategy for Bcl-2 are discussed in Waters J. S., et al., J. Clin. Oncol., 18(9): 1812-1823 (2000); and Kitada S., et al., Antisense Res. Dev., 4(2): 71-79 (1994).

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania G. R., and Chang Y. T., Exp. Opin. Ther. Patents, 10(2): 215-230 (2000). Further, p21WAF1/CIP1 has been described as a potent and universal inhibitor of cyclin-dependent kinases (Cdks) (Ball K. L., Prog. Cell Cycle Res., 3: 125-134 (1997)). Compounds that are known to induce expression of p21WAF1/CIP1 have been implicated in the suppression of cell proliferation and as having tumor suppressing activity (Richon V. M., et al., Proc. Natl. Acad. Sci. USA, 97(18): 10014-10019 (2000)), and are included as cell cycle signaling inhibitors. Histone deacetylase (HDAC) inhibitors are implicated in the transcriptional activation of p21WAF1/CIP1 (Vigushin D. M., and Coombes R. C., Anticancer Drugs, 13(1): 1-13 (2002)), and are suitable cell cycle signaling inhibitors for use in combination herein. Examples of such HDAC inhibitors include, but are not limited to vorinostat, romidepsin, panobinostat, valproic acid, and mocetinostat.

Proteasome inhibitors are drugs that block the action of proteasomes, cellular complexes that break down proteins, like the p53 protein. Several proteasome inhibitors are marketed or are being studied for the treatment of cancer. Suitable proteasome inhibitors for use in combination herein include, but are not limited to bortezomib, disulfiram, epigallocatechin gallate, salinosporamide A, and carfilzomib.

The 70 kilodalton heat shock proteins (Hsp70 s) and 90 kilodalton heat shock proteins (Hsp90s) are a family of ubiquitously expressed heat shock proteins. Hsp70s and Hsp90s are over expressed certain cancer types. Several Hsp70 and Hsp90 inhibitors are being studied in the treatment of cancer. Examples of Hsp70 and Hsp90 inhibitors for use in combination herein include, but are not limited to tanespimycin and radicicol.

Many tumor cells show a markedly different metabolism from that of normal tissues. For example, the rate of glycolysis, the metabolic process that converts glucose to pyruvate, is increased, and the pyruvate generated is reduced to lactate, rather than being further oxidized in the mitochondria via the tricarboxylic acid (TCA) cycle. This effect is often seen even under aerobic conditions and is known as the Warburg Effect.

Lactate dehydrogenase A (LDH-A), an isoform of lactate dehydrogenase expressed in muscle cells, plays a pivotal role in tumor cell metabolism by performing the reduction of pyruvate to lactate, which can then be exported out of the cell. The enzyme has been shown to be upregulated in many tumor types. The alteration of glucose metabolism described in the Warburg effect is critical for growth and proliferation of cancer cells and knocking down LDH-A using RNA-i has been shown to lead to a reduction in cell proliferation and tumor growth in xenograft models (Tennant D. A., et al., Nat. Rev. Cancer, 10(4): 267-277 (2010); Fantin V. R., et al., Cancer Cell, 9(6): 425-434 (2006)).

High levels of fatty acid synthase (FAS) have been found in cancer precursor lesions. Pharmacological inhibition of FAS affects the expression of key oncogenes involved in both cancer development and maintenance. Alli P. M., et al., Oncogene, 24(1): 39-46 (2005).

Inhibitors of cancer metabolism, including inhibitors of LDH-A and inhibitors of fatty acid biosynthesis (or FAS inhibitors), are suitable for use in combination herein.

Cancer gene therapy involves the selective transfer of recombinant DNA/RNA using viral or nonviral gene delivery vectors to modify cancer calls for therapeutic purposes. Examples of cancer gene therapy include, but are not limited to suicide and oncolytic gene therapies, as well as adoptive T-cell therapies.

As used herein "immuno-modulators" refer to any substance including monoclonal antibodies that affects the immune system. A compound of formula (I) or prodrug thereof, or a pharmaceutically acceptable salt thereof, of the invention can be considered an immune-modulator. Immuno-modulators can be used as anti-neoplastic agents for the treatment of cancer. For example, immune-modulators include, but are not limited to, antibodies or other antagonists to CTLA-4, such as ipilimumab (YERVOY®) and tremelimumab; PD-1, such as dostarlimab, nivolumab (OPDIVO®), pembrolizumab (KEYTRUDA®), and cemiplimab (LIBTAYO®); and TIM-3, such as cobolimab. Other immuno-modulators include, but are not limited to, antibodies or other antagonists to PD-L1, OX-40, LAGS, TIM-3, 41BB, and GITR.

As used herein, "PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in the any of the aspects of the invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments, the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')2, scFv and Fv fragments.

Examples of mAbs that bind to human PD-1, and useful in the various aspects and embodiments of the invention, are described in U.S. Pat. Nos. 8,552,154; 8,354,509; 8,168,757; 8,008,449; 7,521,051; 7,488,802; WO2004072286; WO2004056875; and WO2004004771.

Other PD-1 antagonists useful in the any of the aspects and embodiments of the invention include an immunoadhesin that specifically binds to PD-1, and preferably specifically binds to human PD-1, e.g., a fusion protein containing the extracellular or PD-1 binding portion of PD-L1 or PD-L2 fused to a constant region such as an Fc region of an immunoglobulin molecule. Examples of immunoadhesin molecules that specifically bind to PD-1 are described in WO2010027827 and WO2011066342. Specific fusion proteins useful as the PD-1 antagonist in the treatment method, medicaments and uses of the invention include AMP-224 (also known as B7-DCIg), which is a PD-L2-FC fusion protein and binds to human PD-1.

Nivolumab is a humanized monoclonal anti-PD-1 antibody commercially available as OPDIVO®. Nivolumab is indicated for the treatment of some unresectable or metastatic melanomas. Nivolumab binds to and blocks the activation of PD-1, an Ig superfamily transmembrane protein, by its ligands PD-L1 and PD-L2, resulting in the activation of T-cells and cell-mediated immune responses against tumor cells or pathogens. Activated PD-1 negatively regulates T-cell activation and effector function through the suppression of PI3k/Akt pathway activation. Other names for nivolumab include: BMS-936558, MDX-1106, and ONO-4538. The amino acid sequence for nivolumab and methods of using and making are disclosed in U.S. Pat. No. 8,008,449.

Pembrolizumab is a humanized monoclonal anti-PD-1 antibody commercially available as KEYTRUDA®. Pembrolizumab is indicated for the treatment of some unresectable or metastatic melanomas. The amino acid sequence of pembrolizumab and methods of using are disclosed in U.S. Pat. No. 8,168,757.

Anti-PD-L1 antibodies and methods of making the same are known in the art. Such antibodies to PD-L1 may be polyclonal or monoclonal, and/or recombinant, and/or humanized. PD-L1 antibodies are in development as immuno-modulatory agents for the treatment of cancer.

Exemplary PD-L1 antibodies are disclosed in U.S. Pat. Nos. 9,212,224; 8,779,108; 8,552,154; 8,383,796; 8,217,149; US Patent Publication No. 20110280877; WO2013079174; and WO2013019906. Additional exemplary antibodies to PD-L1 (also referred to as CD274 or B7-H1) and methods for use are disclosed in U.S. Pat. Nos. 8,168,179; 7,943,743; 7,595,048; WO2014055897; WO2013019906; and WO2010077634. Specific anti-human PD-L1 monoclonal antibodies useful as a PD-1 antagonist in the treatment method, medicaments and uses of the invention include MPDL3280A, BMS-936559, MED14736, MSB0010718C.

Atezolizumab is a fully humanized monoclonal anti-PD-L1 antibody commercially available as TECENTRIQ®. Atezolizumab is indicated for the treatment of some locally advanced or metastatic urothelial carcinomas. Atezolizumab blocks the interaction of PD-L1 with PD-1 and CD80. Other exemplary PD-L1 antibodies include avelumab (BAVENCIO®) and durvalumab (IMFINZI®).

Bifunctional fusion proteins which target PD-1 or PD-L1 along with another target may also be useful with the invention. Bintrafusp alfa, a bifunctional fusion protein designed to simultaneously block the PD-L1 and TGF-β pathways, is disclosed in U.S. Pat. No. 9,676,863.

CD134, also known as OX40, is a member of the TNFR-superfamily of receptors which is not constitutively expressed on resting naïve T cells, unlike CD28. OX40 is a secondary costimulatory molecule, expressed after 24 to 72 hours following activation; its ligand, OX40L, is also not expressed on resting antigen presenting cells, but is following their activation. Expression of OX40 is dependent on full activation of the T cell; without CD28, expression of OX40 is delayed and of fourfold lower levels. OX-40 antibodies, OX-40 fusion proteins and methods of using them are disclosed in U.S. Pat. Nos. 7,504,101; 7,758,852; 7,858,765; 7,550,140; 7,960,515; WO2012027328; WO2013028231.

Additional examples of a further active ingredient or ingredients (anti-neoplastic agent) for use in combination or co-administered with the disclosed compounds are antibodies or other antagonists to CD20, retinoids, or other kinase inhibitors. Examples of such antibodies or antagonists include, but are not limited to rituximab (RITUXAN® and MABTHERA®), ofatumumab (ARZERRA®), and bexarotene (TARGRETIN®).

Additional examples of a further active ingredient or ingredients (anti-neoplastic agent) for use in combination or co-administered with the disclosed compounds are Toll-like Receptor 4 (TLR4) antagonists, including but not limited to aminoalkyl glucosaminide phosphates (AGPs).

AGPs are known to be useful as vaccine adjuvants and immunostimulatory agents for stimulating cytokine production, activating macrophages, promoting innate immune response, and augmenting antibody production in immunized animals. AGPs are synthetic ligands of TLR4. AGPs and their immunomodulating effects via TLR4 are disclosed in patent publications such as WO 2006016997, WO 2001090129, and/or U.S. Pat. No. 6,113,918 and have been reported in the literature. Additional AGP derivatives are disclosed in U.S. Pat. Nos. 7,129,219, 6,911,434, and 6,525,028. Certain AGPs act as agonists of TLR4, while others are recognized as TLR4 antagonists.

Additional non-limiting examples of a further active ingredient or ingredients (anti-neoplastic agent) for use in combination or co-administered with the disclosed compounds are antibodies to ICOS.

CDRs for murine antibodies to human ICOS having agonist activity are shown in PCT/EP2012/055735 (WO 2012131004). Antibodies to ICOS are also disclosed in WO 2008137915, WO 2010056804, EP 1374902, EP1374901, and EP1125585.

Additional examples of a further active ingredient or ingredients (anti-neoplastic agent) for use in combination or co-administered with the disclosed compounds are poly ADP ribose polymerase (PARP) inhibitors. Non-limiting examples of such inhibitors include niraparib, olaparib, rucaparib, and talazoparib.

The normal function of B cell maturation antigen (BCMA) is to promote cell survival by transduction of signals from two known ligands (B cell activating factor from the TNF family (BAFF/BLyS) and a proliferation inducing ligand (APRIL). BCMA expression is restricted to B cells at later stages of differentiation, with expression on germinal center B cells in tonsil, blood plasma blasts and long-lived plasma cells. BCMA is expressed in various B cell malignancies, including multiple myeloma (MM), Diffuse Large B Cell Lymphoma (DLBCL), Large B Cell Lymphoma (LBCL), Chronic Lymphocytic Leukemia (CLL) and Waldenstrom's Macroglobulinemia (WM) at varying frequencies. The restricted normal tissue expression profile of BCMA, along with its up-regulation and survival function in MM and other cancers makes it an attractive target for a therapeutic antibody with direct cell killing activity. Inhibitors of BCMA, and other targeting agents, such as antibody drug conjugates, may be used with the invention. Belantamab mafodotin, an anti-BCMA antibody drug conjugate, is disclosed in U.S. Pat. No. 9,273,141.

Additional non-limiting examples of a further active ingredient or ingredients (anti-neoplastic agent) for use in combination or co-administered with the disclosed compounds are STING modulating compounds, CD39 inhibitors and A2a and A2a adenosine antagonists.

Select anti-neoplastic agents that may be used in combination with a compound of formula (I) or a prodrug thereof, or a pharmaceutically acceptable salt thereof, include but are not limited to: abarelix, abemaciclib, abiraterone, afatinib, aflibercept, aldoxorubicin, alectinib, alemtuzumab, arsenic trioxide, asparaginase, axitinib, AZD-9291, belinostat, bendamustine, bevacizumab, blinatumomab, bosutinib, brentuximab vedotin, cabazitaxel, cabozantinib, capecitabine, ceritinib, clofarabine, cobimetinib, crizotinib, daratumumab, dasatinib, degarelix, denosumab, dinutuximab, docetaxel, elotuzumab, entinostat, enzalutamide, epirubicin, eribulin, filgrastim, flumatinib, fulvestrant, fruquintinib, gemtuzumab ozogamicin, ibritumomab, ibrutinib, idelalisib, imatinib, irinotecan, ixabepilone, ixazomib, lenalidomide, lenvatinib, leucovorin, mechlorethamine, necitumumab, nelarabine, netupitant, nilotinib, obinutuzumab, olaparib, omacetaxine, osimertinib, oxaliplatin, paclitaxel, palbociclib, palonosetron, panitumumab, pegfilgrastim, peginterferon alfa-2b, pemetrexed, plerixafor, pomalidomide, ponatinib, pralatrexate, quizartinib, radium-223, ramucirumab, regorafenib, rolapitant, rucaparib, sipuleucel-T, sonidegib, sunitinib, talimogene laherparepvec, tipiracil, topotecan, trabectedin, trifluridine, triptorelin, uridine, vandetanib, velaparib, vemurafenib, venetoclax, vincristine, vismodegib, and zoledronic acid. Preferred anti-neoplastic agents include venetoclax.

Preferred agents include BCL2 targeting agents such as venetoclax, tyrosine kinase inhibitors such as those targeting FLT3 mutations (gilteritinib and midostaurin), the sonic hedgehog inhibitor glasdegib, IDH1 or IHD2 mutant targeting agents such as ivosidenib or enasidenib, NEDD8 targeting agents such as pevonedistat, HDAC inhibitors such as vorinostat or panobinostat, agents targeting the PRC2 complex such as tazemetostat (EZH2i) or MAK683 (EEDi), platinum-based anti-neoplastic agents such as cisplatin, IO targeting agents such as anti-CD47 (magrolimab), TIM-3 (sabatolimab), CTLA-4 (ipilimumab), and anti-PD-1/PD-L1 (pembrolizmab), as well as P53 targeting drugs.

In one embodiment, the cancer treatment method of the claimed invention includes the co-administration a compound of Formula (I) and/or a prodrug thereof and/or a pharmaceutically acceptable salt thereof and at least one anti-neoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, cell cycle signaling inhibitors; proteasome inhibitors; and inhibitors of cancer metabolism.

The compounds of formula (I) or prodrugs thereof, and pharmaceutically acceptable salts thereof, may be co-administered with at least one other active agent known to be useful for treating beta hemoglobinopathies, such as sickle cell disease, sickle cell anemia, and beta thalassemia.

Examples of a further active ingredient or ingredients for use in combination or co-administered with the invented combinations is hydroxyurea.

The compounds of the invention are prepared using conventional organic synthetic methods. Suitable synthetic routes are depicted below in the following general reaction schemes. All of the starting materials are commercially available or are readily prepared from commercially available starting materials by those of skill in the art.

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

Ac (acetyl);
Ac$_2$O (acetic anhydride);
CH$_3$CN (acetonitrile);
Boc (tert-Butoxycarbonyl);
Boc$_2$O (di-tert-butyl dicarbonate);
Cbz (benzyloxycarbonyl);
DCE (1,2-dichloroethane);
DCM (dichloromethane);
ATP (adenosine triphosphate);
Bis-pinacolatodiboron (4,4,4',4',5,5,5',5'-Octamethyl-2,2'-bi-1,3,2-dioxaborolane);
BSA (bovine serum albumin);
C18 (refers to 18-carbon alkyl groups on silicon in HPLC stationary phase)
Cy (cyclohexyl);
DCM (dichloromethane);
DIEA (diisopropylethylamine);
DIPEA (Hunig's base, N-ethyl-N-(1-methylethyl)-2-propanamine);
Dioxane (1,4-dioxane);
DMAP (4-dimethylaminopyridine);
DME (1,2-dimethoxyethane);
DMEDA (N,N'-dimethylethylenediamine);
DMF (N,N-dimethylformamide);
DMSO (dimethylsulfoxide);
DPPA (diphenyl phosphoryl azide);
EDC (N-(3-dimethylaminopropyl)-N'ethylcarbodiimide) hydrochloride salt;
EDTA (ethylenediaminetetraacetic acid);
EtOAc (ethyl acetate);
EtOH (ethanol);
Et$_2$O (diethyl ether);
HEPES (4-(2-hydroxyethyl)-1-piperazinyl ethane sulfonic acid);
HATU (O-(7-Azabenzotriazol-1-yl)-N,N,N',N'-tetramethyluronium hexafluorophosphate);
HOAt (1-hydroxy-7-azabenzotriazole);
HOBt (1-hydroxybenzotriazole);
HOAc (acetic acid);
HPLC (high pressure liquid chromatography);
HMDS (hexamethyldisilazide);
Hunig's Base (N,N-Diisopropylethylamine);
IPA (isopropyl alcohol);
Indoline (2,3-dihydro-1H-indole);
KHMDS (potassium hexamethyldisilazide);
LAH (lithium aluminum hydride);
LDA (lithium diisopropylamide);
LHMDS (lithium hexamethyldisilazide);
MeOH (methanol);
MTBE (methyl tert-butyl ether);
mcM (micromolar);
mCPBA (m-chloroperbezoic acid);
NaHMDS (sodium hexamethyldisilazide);
NCS (N-chlorosuccinimide);
NBS (N-bromosuccinimide);
PE (petroleum ether);
Pd$_2$(dba)$_3$ (Tris(dibenzylideneacetone)dipalladium(0);
Pd(dppf)Cl$_2$.DCM Complex ([1,1'-Bis(diphenylphosphino) ferrocene]dichloropalladium(11).dichloromethane complex);
PyBOP (benzotriazol-1-yl-oxytripyrrolidinophosphonium hexafluorophosphate);
PyBrOP (bromotripyrrolidinophosphonium hexafluorophosphate);
RPHPLC (reverse phase high pressure liquid chromatography);
RT (room temperature);
Sat. (saturated);
SFC (supercritical fluid chromatography);
SGC (silica gel chromatography);
SM (starting material);
TLC (thin layer chromatography);
TEA (triethylamine);
TEMPO (2,2,6,6-Tetramethylpiperidinyl 1-oxyl, free radical);
TFA (trifluoroacetic acid);
THF (tetrahydrofuran); and
Ts-Cl (p-toluenesulfonyl chloride).

All references to ether are to diethyl ether and brine refers to a saturated aqueous solution of NaCl.

Synthetic Schemes

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, Protecting Groups in Organic Synthesis (4th ed.), John Wiley & Sons, NY (2006). In some instances, a substituent may be specifically selected to be reactive under the reaction conditions used. Under these circumstances, the reaction conditions convert the selected substituent into another substituent that is either useful as an intermediate compound or is a desired substituent in a target compound.

Prodrugs of formula 16 in Scheme 1 can either be a single enantiomer or a racemate depending on whether a chiral resolution is performed. The dicyanopyridine core intermediate 6 can be readily prepared from 2-cyanoacetamide 1. The prodrug containing intermediate can be prepared by starting with a substituted mandelic acid such as the commercially available 4-hydroxymandelic acid 7. A variety of protecting group scenarios, as well as leaving groups, can be imagined that would allow for the conversion of 7 to the $S_N2$ electrophile partner 13.

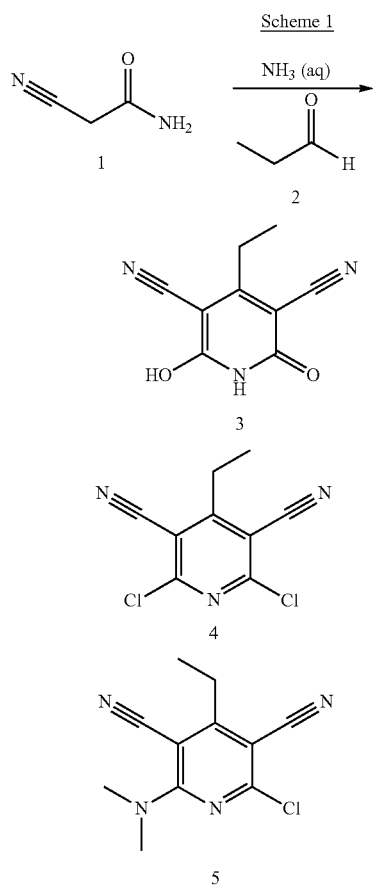

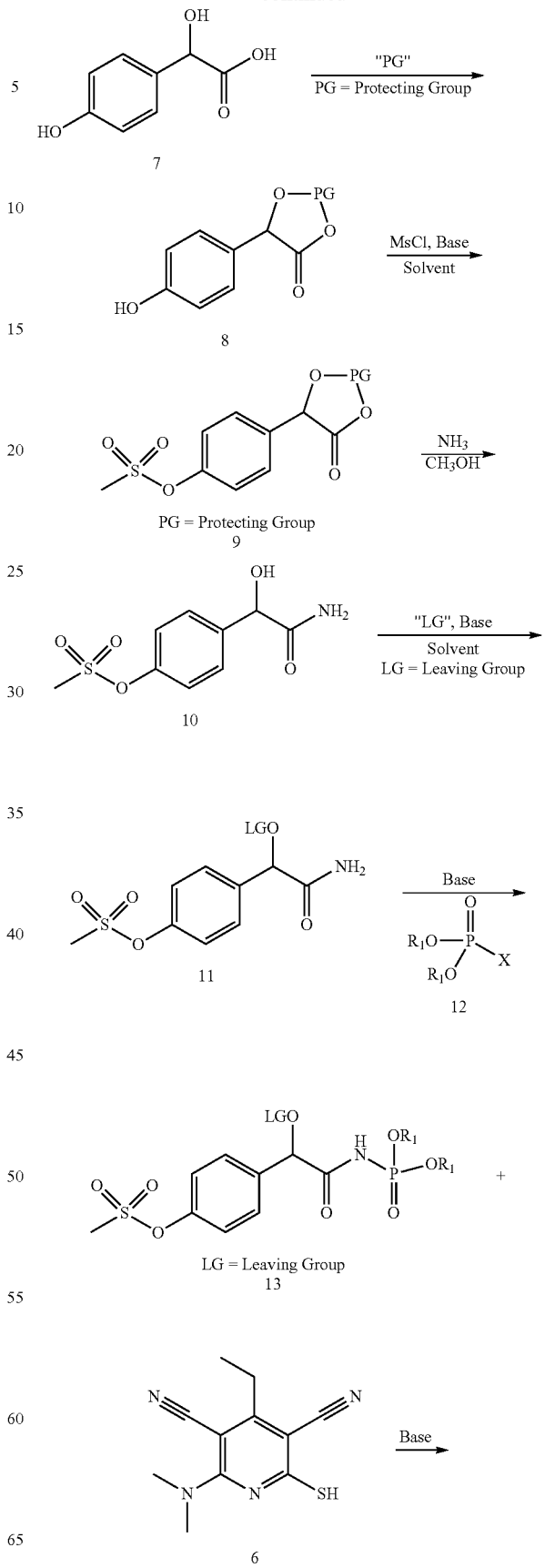

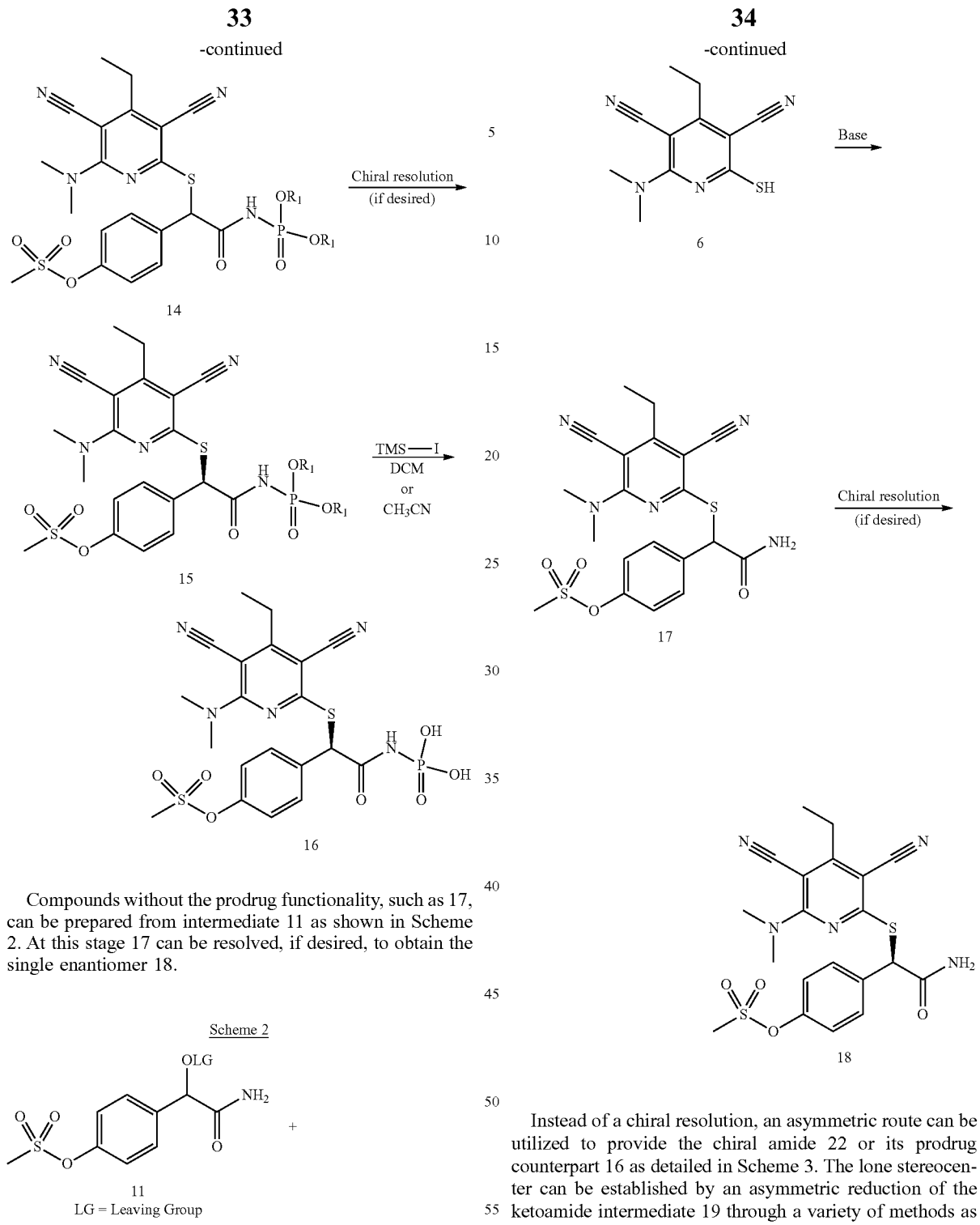

Compounds without the prodrug functionality, such as 17, can be prepared from intermediate 11 as shown in Scheme 2. At this stage 17 can be resolved, if desired, to obtain the single enantiomer 18.

Instead of a chiral resolution, an asymmetric route can be utilized to provide the chiral amide 22 or its prodrug counterpart 16 as detailed in Scheme 3. The lone stereocenter can be established by an asymmetric reduction of the ketoamide intermediate 19 through a variety of methods as described in the literature.

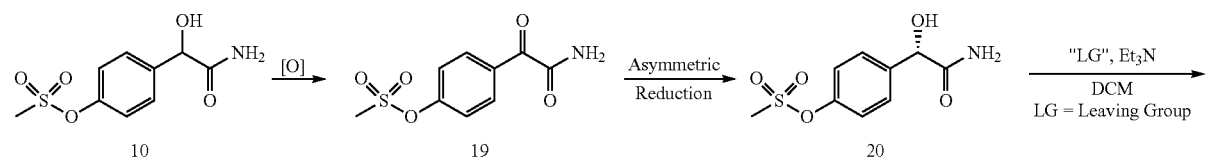

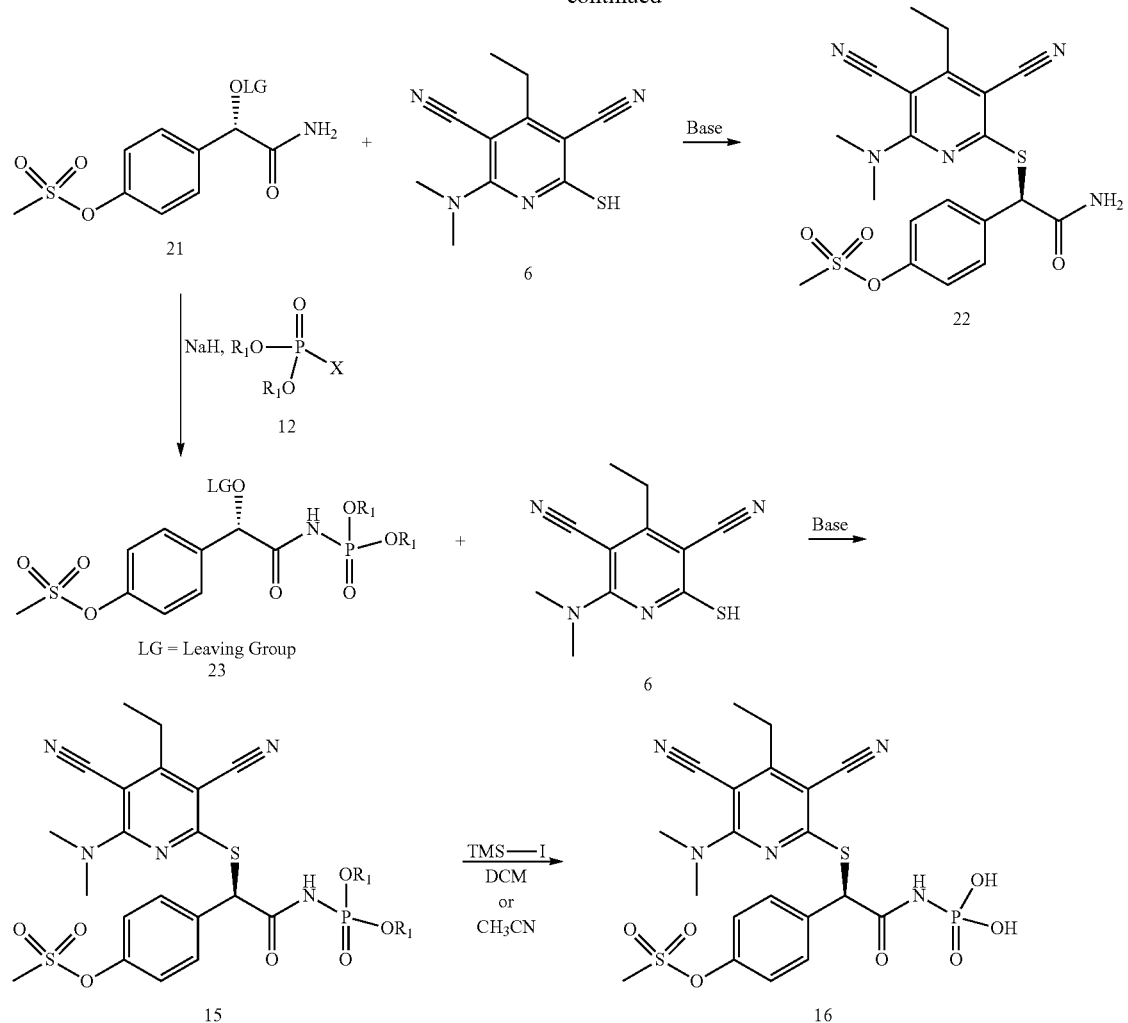
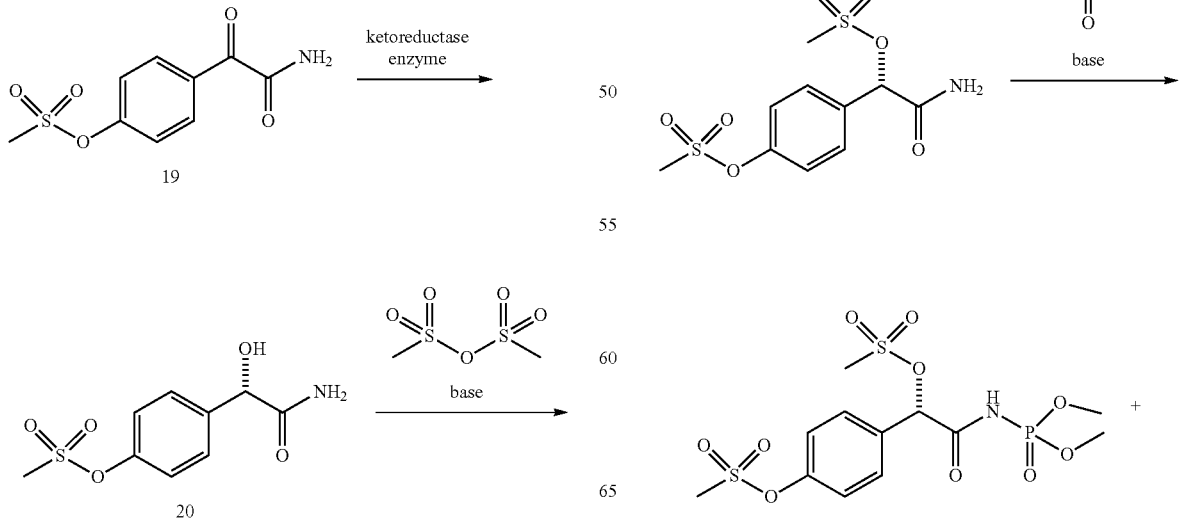

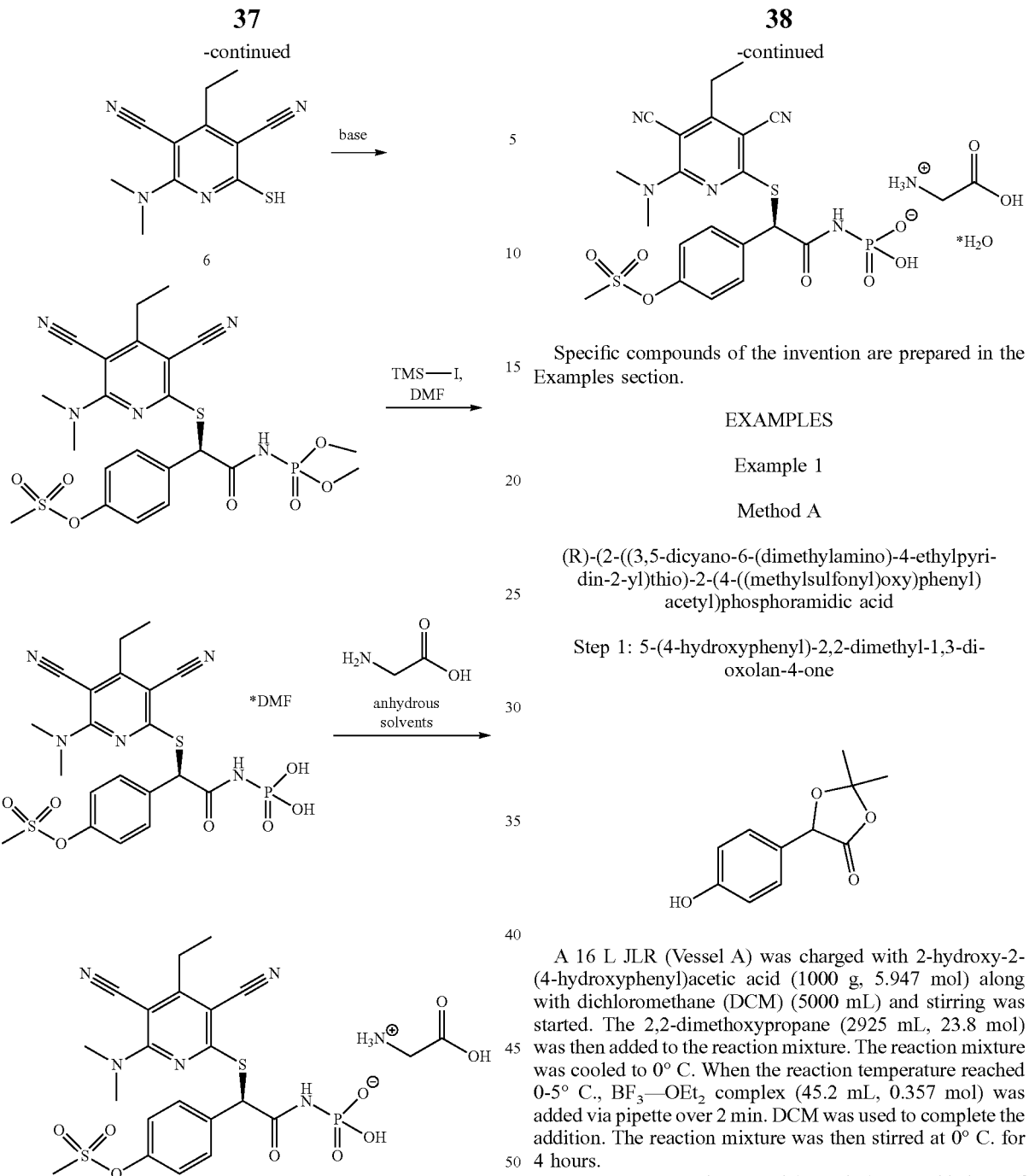

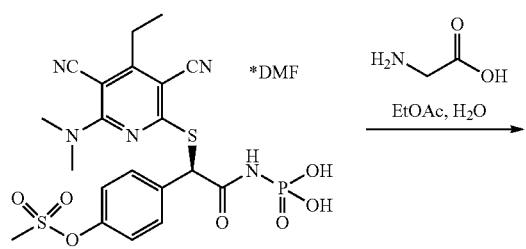

Scheme 5
Asymmetric synthesis of glycine salt monohydrate

Specific compounds of the invention are prepared in the Examples section.

EXAMPLES

Example 1

Method A (R)-(2-((3,5-dicyano-6-(dimethylamino)-4-ethylpyridin-2-yl)thio)-2-(4-((methylsulfonyl)oxy)phenyl)acetyl)phosphoramidic acid Step 1: 5-(4-hydroxyphenyl)-2,2-dimethyl-1,3-dioxolan-4-one A 16 L JLR (Vessel A) was charged with 2-hydroxy-2-(4-hydroxyphenyl)acetic acid (1000 g, 5.947 mol) along with dichloromethane (DCM) (5000 mL) and stirring was started. The 2,2-dimethoxypropane (2925 mL, 23.8 mol) was then added to the reaction mixture. The reaction mixture was cooled to 0° C. When the reaction temperature reached 0-5° C., $BF_3$—$OEt_2$ complex (45.2 mL, 0.357 mol) was added via pipette over 2 min. DCM was used to complete the addition. The reaction mixture was then stirred at 0° C. for 4 hours.

To a separate reaction vessel (Vessel B), was added 5 L of saturated aqueous $NaHCO_3$ solution and the internal temperature of the vessel was set to 0° C. The reaction mixture from Vessel A was added to the saturated sodium bicarbonate solution in Vessel B via vacuum transfer. Once addition was complete, the suspension was stirred for 10 minutes, then warmed to 20° C. The organic layer was separated into a 20 L carboy. The aqueous layer was extracted with additional DCM (1.2 L) and this organic layer was combined with the organic layer in the 20 L carboy. The combined organic layers were returned to the JLR and washed with brine (3 L). The organic layer was again separated. The next day, the DCM was distilled to a minimum stir volume. The remaining reaction mixture was concentrated to dryness on a rotary evaporator. The off-white solid that remained was then dried under vacuum to provide 5-(4-hydroxyphenyl)-2,2-dimethyl-1,3-dioxolan-4-one (720 g, 58.1% yield) as an off-white solid. ¹HNMR (400 MHz, CDCl₃) δ ppm 7.28-7.24 (m, 2H), 6.83-6.78 (m, 2H), 5.37 (s, 1H), 1.75 (s, 3H), 1.70-1.67 (m, 3H).

Step 2:
4-(2,2-dimethyl-5-oxo-1,3-dioxolan-4-yl)phenyl methanesulfonate

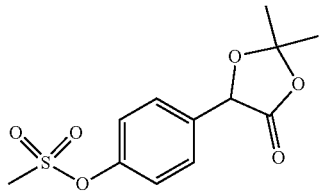

A 16 L JLR (Vessel A) was charged with a solution of 5-(4-hydroxyphenyl)-2,2-dimethyl-1,3-dioxolan-4-one (720.0 g, 3458 mmol) dissolved in dichloromethane (DCM) (4390 mL) and the reaction mixture was cooled to 0° C. Mesyl Chloride (323 mL, 4150 mmol) was then added to the reaction mixture via addition funnel over ~5 min; the transfer was completed by rinsing the addition funnel with 100 mL DCM into the reactor. Triethylamine (723 mL, 5187 mmol) was slowly added over ~43 min using an addition funnel; the transfer was completed by rinsing the addition funnel with 100 mL DCM into the reactor. The reaction mixture was stirred at 0° C. for 2 hours.

To a separate reaction vessel (Vessel B) was added 4390 mL of a saturated aqueous NaHCO₃ solution and the internal temperature of the vessel was set to 0° C. Vessel B was placed under reduced pressure to facilitate the slow vacuum transfer of the reaction mixture from Vessel A into Vessel B. Vessel A was rinsed with 300 mL of DCM and this wash solution was also transferred to Vessel B. Stirring was halted and 500 mL of DI water was added to Vessel B via sprayball to wash down reactor walls. Agitation was restarted and the internal temperature was set to 20° C. Stirring was paused after 30 min and the biphasic mixture was allowed to stand overnight at 20° C. The internal temperature was set to 10° C. and the vessel placed under a vacuum. After 30 minutes, the internal temperature was raised to 25° C. Over the ensuing 1.5 hours, the volume was reduced to between 1.5 and 2 L, and the vacuum was released. The organic layer in Vessel B was drained and the reactor rinsed with DCM to complete the transfer. The remaining organic layer was concentrated to dryness on a rotary evaporator and further dried under high vacuum to provide 4-(2,2-dimethyl-5-oxo-1,3-dioxolan-4-yl)phenyl methanesulfonate (689.67 g, 69.7% yield) as an off-white solid. LCMS m/z=304.2 [M+H₂O]⁺. ¹HNMR (400 MHz, CDCl₃) δ ppm 7.61-7.56 (m, 2H), 7.39-7.35 (m, 2H), 5.44 (s, 1H), 3.18 (s, 3H), 1.76 (s, 3H), 1.72 (s, 3H).

Step 3: 4-(2-amino-1-hydroxy-2-oxoethyl)phenyl methanesulfonate

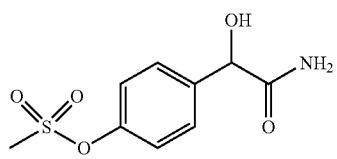

A 16 L JLR was charged with 4-(2,2-dimethyl-5-oxo-1,3-dioxolan-4-yl)phenyl methanesulfonate (689.67 g, 2409 mmol) along with methanol (2400 mL) and the solution was stirred. The jacket temperature was set to 0° C. To the reaction mixture was added a solution of ammonia in MeOH (7M) (1377 mL, 9636 mmol) over 47 minutes. After the reaction mixture was stirred at the same temperature for 7.5 hours, the jacket temperature was then warmed to 10° C. An additional 250 mL (1750 mmol) of 7M ammonia in methanol was added and the reaction mixture was stirred at the same temperature for 16.5 hours. The reaction mixture was then filtered through a pan filter. The collected solid was washed with additional methanol and dried to provide 4-(2-amino-1-hydroxy oxoethyl)phenyl methanesulfonate (544.86 g, 92% yield) as a white solid. LCMS m/z=268.1 [M+Na]⁺. ¹HNMR (400 MHz, DMSO-d₆) δ ppm 7.64-7.54 (m, 3H), 7.40-7.32 (m, 3H), 6.29 (d, J=4.4 Hz, 1H), 5.03 (d, J=4.4 Hz, 1H), 3.38 (s, 3H).

Step 4: 4-(2-amino-1-((methylsulfonyl)oxy)-2-oxoethyl)phenyl methanesulfonate

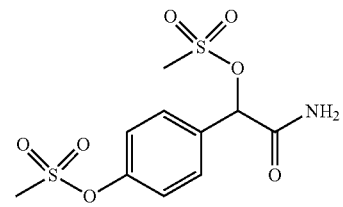

A 16 L JLR (Vessel A) was charged with 4-(2-amino-1-hydroxy-2-oxoethyl)phenyl methanesulfonate (545 g, 2222 mmol) and dichloromethane (DCM) (4331 mL). Stirring commenced and the jacket temperature was set to 0° C. After 25 minutes, mesyl chloride (216 mL, 2778 mmol) was added to the reaction mixture. Triethylamine (465 mL, 3333 mmol) was then slowly added through an addition funnel over 35 minutes. After the addition was complete, the jacket temperature was raised to 20° C. over 40 minutes. The reaction mixture was allowed to stir at the same temperature for 19 hours, but starting material remained. The jacket temperature was reset to 0° C. Additional mesyl chloride (30 mL, 385.8 mmol) was added to the reaction mixture along with 70 mL of DCM to complete the addition. An additional amount of triethylamine (70 mL, 501.7 mmol) was then added. Upon completion of addition, the jacket temperature was set to 22° C. and the reaction mixture stirred for 1 hour.

A separate reaction vessel (Vessel B) was charged with saturated aqueous sodium bicarbonate solution (2166 mL) and the jacket temperature set to 0° C. The reaction mixture from Vessel A was vacuum transferred to Vessel B at a rate to control the exotherm and gas evolution. Upon completion of the transfer, the jacket temperature was raised to 20° C. over 30 minutes and the reaction mixture was stirred at this temperature for an additional 30 minutes. The reaction mixture was then filtered through a pan filter. The collected solid material was washed with water (550 mL) and dried under vacuum in the pan filter overnight. The solid was then further dried in a vacuum oven at 45° C. overnight to provide 4-(2-amino-1-((methylsulfonyl)oxy)-2-oxoethyl)phenyl methanesulfonate (530.36 g, 73.8% yield) as a white solid. LCMS m/z=346.1 [M+Na]⁺. ¹HNMR (400 MHz, DMSO-d$_6$) δ ppm 7.88 (s, 1H), 7.63-7.58 (m, 2H), 7.45-7.41 (m, 2H), 5.92 (s, 1H), 3.42 (s, 3H), 3.27 (s, 3H).

Step 5: 4-(2-((bis(benzyloxy)phosphoryl)amino)-1-((methylsulfonyl)oxy) oxoethyl)phenyl methanesulfonate

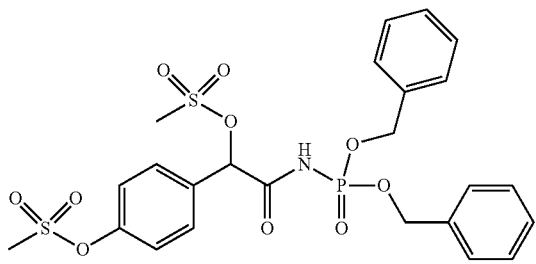 [SMILES: CS(=O)(=O)Oc1ccc(C(OS(C)(=O)=O)C(=O)NP(=O)(OCc2ccccc2)OCc2ccccc2)cc1]

A 16 L JLR (Vessel A), with an internal temperature set to −5° C., was charged with 8 L of tetrahydrofuran (THF) and stirring started. The reaction vessel was then charged with sodium hydride (60% by weight) (203.45 g, 5.087 mol) via a powder addition funnel. The container and funnel were rinsed with 1 L THF into the reactor to complete the transfer. To the reaction mixture was added tetrabenzyl pyrophosphate (1471 g, 2.732 mol) via a powder addition funnel. The container and funnel were rinsed with 0.5 L THF into the reactor to complete the transfer. The reaction temperature was set to −3° C. and an additional 2.5 L of THF was added to the reaction mixture. To the reaction mixture was added 4-(2-amino-1-((methylsulfonyl)oxy)-2-oxoethyl)phenyl methanesulfonate (736 g, 2276 mol) in 7 portions over 30 minutes while venting the reaction mixture in between additions. The addition was completed by rinsing the dimesylate container with additional THF (3 L) bringing the total THF in the reactor to 15 L. The stirring was increased to 300 rpm and the reaction jacket was warmed to 25° C. over 30 minutes. The reaction mixture was then stirred at the same temperature for 2 hours.

The reaction was quenched in 2 portions. To a separate reaction vessel (Vessel B), with the internal temperature set to 0° C., was added 6 L of a saturated citric acid solution. To this solution in Vessel B was added 8.5 L of the reaction mixture from Vessel A over 30 minutes. During the addition the jacket temperature of Vessel B was adjusted to −15° C. Upon completion of the addition, the jacket temperature of Vessel B was raised to 10° C. After stirring for 1 hour at 10° C., the mixture was filtered through a pan filter (two shark skin filter papers were used). After Vessel B was completely drained, it was charged a second time with 6 L of a saturated citric acid solution and the temperature adjusted to −15° C. The quenching procedure was repeated by adding the remaining reaction mixture from Vessel A to Vessel B over 35 minutes. The Vessel B temperature was again adjusted to 10° C. Vessel A was rinsed with 500 mL of THF and this rinse was added to Vessel B. The jacket temperature of Vessel B was adjusted to 25° C. and the mixture was kept at the same temperature for 25 minutes. The reaction mixture was filtered through the same pan filter used previously. Tert-butyl methyl ether (TBME) was added to the pan filter to aid the filtration but provided little improvement if any. After 50 minutes the material in the pan filter was transferred back into the reactor vessel via vacuum transfer. TBME (8 L) was added to the reactor and the mixture was again filtered through a pan filter. As the filtration proceeded the solid mixture became a paste and required scraping to facilitate the process. After 1.5 hours all of the contents from the vessel had been added to the pan filter, and the reactor vessel was rinsed with an additional 1.5 L of TBME. This rinse was added to the pan filter and the filtration was left overnight. After overnight vacuum filtration, the isolated solid was transferred to glass drying trays. The trays were placed in to a vacuum oven at 25° C. overnight.

After drying overnight in the vacuum oven, the solid material was transferred to a 12 L 3-neck flask and suspended in 8 L of water. The mixture was mixed vigorously for 1 hour using an overhead mechanical stirrer and then filtered through a stainless steel pan filter equipped with 3 layers of shark skin filter paper. An additional 2 L of water was used to complete the transfer. The filter cake was washed twice with 2 L of water followed by 4 L of TBME. The solid was then dried under vacuum overnight in the pan filter. The solid was transferred from the pan filter to two baking dishes and further dried in a vacuum oven with a nitrogen bleed with no heat for ~48 hours. The solid was combined to give 4-(2-((bis(benzyloxy)phosphoryl)amino)-1-((methylsulfonyl)oxy)-2-oxoethyl)phenyl methanesulfonate (1060 g, 80%) as a white solid. LCMS m/z=584.3 [M+H]$^+$. $^1$HNMR (400 MHz, DMSO-d$_6$) δ ppm 10.51 (d, J=9.4 Hz, 1H), 7.67-7.61 (m, 2H), 7.48-7.43 (m, 2H), 7.41-7.31 (m, 8H), 7.28-7.23 (m, 2H), 6.11 (s, 1H), 5.10-4.85 (m, 4H), 3.41 (s, 3H), 3.29 (s, 3H).

Step 6: Ammonium 3,5-dicyano-4-ethyl-6-hydroxypyridin-2-olate

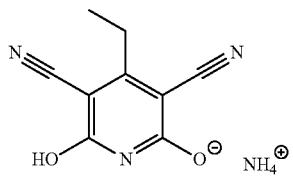

To a stirred solution of 2-cyanoacetamide (300 g, 3.571 mol) and ammonia (25% by weight in water, 618 mL, 7.142 mol) in water (750 mL) cooled to 0° C., was added propionaldehyde (128 mL, 1.785 mol) dropwise. The reaction mixture was stirred at room temperature for 3 h. The precipitated solid was collected by filtration, washed with ice cold water (2×500 mL), followed by cold methanol (300 mL), and dried to give ammonium 3,5-dicyano-4-ethyl-6-hydroxypyridin-2-olate (150 g, 39%) as an off-white solid. LCMS m/z=188.0 [M−H]$^−$. $^1$H NMR (400 MHz, DMSO-d$_6$) δ ppm 10.35 (s, 1H), 7.1 (br s, 4H), 2.48 (q, J=7.6 Hz, 2H), 1.17 (t, J=7.6 Hz, 3H).

Step 7: 2,6-dichloro-4-ethylpyridine-3,5-dicarbonitrile

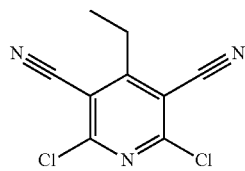

To a stirred suspension of ammonium 3,5-dicyano-4-ethyl-6-hydroxypyridin-2-olate (150 g, 697 mmol) in POCl$_3$ (750 mL, 8046 mmol) cooled to 0° C., was added N,N-dimethylaniline (150 mL, 1601 mmol) dropwise. The reaction mixture was heated at 120° C. for 6 h. Progress of the reaction was monitored by TLC (TLC system 10% EtOAc in Hexane, Rf: 0.6, Detection: UV). The reaction mixture was concentrated under reduced pressure to obtain the crude material. The crude material was diluted with ice cold water and stirred for 10 min. The precipitated solid was collected by filtration and dried. The solid was dissolved in dichloromethane (2 L), washed with saturated sodium bicarbonate solution (1 L), water (1.5 L), and brine solution (1 L). The organic layer was dried over anhydrous Na$_2$SO$_4$, filtered, and concentrated under reduced pressure to provide a yellow solid. The solid material was triturated with diethyl ether (500 mL), filtered, and dried to afford 2,6-dichloro-4-ethylpyridine-3,5-dicarbonitrile (130 g, 571 mmol, 82% yield) as a yellow solid. LCMS m/z=224.1 [M–H]$^-$. $^1$H NMR (400 MHz, CDCl$_3$) δ ppm 3.13 (q, J=7.6 Hz, 2H), 1.42 (t, J=7.6 Hz, 3H).

Step 8: 2-(dimethylamino)-4-ethyl-6-mercaptopyridine-3,5-dicarbonitrile

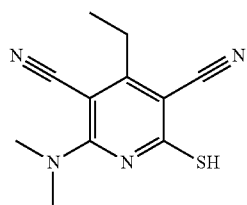 [SMILES: CCc1c(C#N)c(S)nc(N(C)C)c1C#N]

A 3 L 3-neck flask with overhead stirring and temperature probe was charged with 2,6-dichloro-4-ethylpyridine-3,5-dicarbonitrile (130.0 g, 575 mmol) and DMF (1300 mL), and stirred to form a reddish solution. The reaction flask was placed in an ice bath and the solution was stirred until the internal temp reached ca. 3° C. A solution of dimethylamine in THF (288 mL, 575 mmol) was added via addition funnel at such a rate that the internal temp remained <5° C. Triethylamine (80 mL, 575 mmol) was added dropwise, maintaining the internal temp <7° C. The mixture became dark purple near the end of the triethylamine addition. Potassium thioacetate (164 g, 1438 mmol) was added and the cooling bath was removed. The mixture was stirred at RT for 2 h and poured into a mixture of cold 1 N HCl solution (1150 mL, 1150 mmol) and water (2600 mL). The mixture was stirred ca. 30 min and the precipitated solids were collected by filtration. The filter cake was washed with several portions of water (1 L total) and dried overnight on the Buchner funnel. The orange solid was transferred to a 3 L 3-neck flask with overhead stirring. Ethyl acetate (1200 mL) was charged and the slurry was stirred ca. 30 min. Solids were collected by filtration. The cake was slurried with 200 mL EtOAc and pulled dry on the Buchner funnel. Slurrying/drying was repeated twice more affording 2-(dimethylamino)-4-ethyl-6-mercaptopyridine-3,5-dicarbonitrile (115.57 g, 87% yield) as a bright yellow solid. LCMS m/z=233.0 [M+H]$^+$. $^1$HNMR: (400 MHz, DMSO-d$_6$) δ ppm 14.05-9.86 (m, 1H), 3.29 (s, 6H), 2.68 (q, J=7.3 Hz, 2H), 1.21 (t, J=7.6 Hz, 3H).

Step 9: 4-(2-((bis(benzyloxy)phosphoryl)amino)-1-((3,5-dicyano-6-(dimethylamino)-4-ethylpyridin-2-yl)thio)-2-oxoethyl)phenyl methanesulfonate

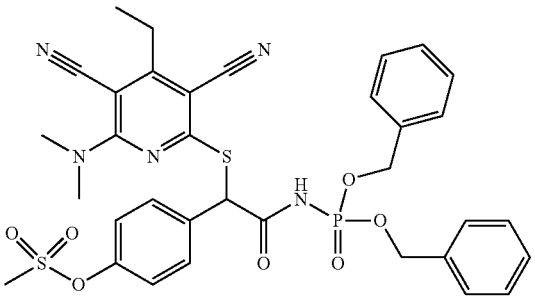 [SMILES: CCc1c(C#N)c(SC(C(=O)NP(=O)(OCc2ccccc2)OCc2ccccc2)c2ccc(OS(C)(=O)=O)cc2)nc(N(C)C)c1C#N]

To a 16 L JLR was added dichloromethane (8 L), 4-(2-((bis(benzyloxy)phosphoryl)amino)-1-((methylsulfonyl)oxy)-2-oxoethyl)phenyl methanesulfonate (966 g, 1.655 mol), 2-(dimethylamino)-4-ethyl-6-mercaptopyridine-3,5-dicarbonitrile (381 g, 1.640 mol), and dichloromethane (8 L). The reaction mixture was cooled 5° C. Triethylamine (174 g, 1.722 mol) was added via addition funnel over 21 minutes to the reaction mixture while maintaining the reaction temperature between 3.3-4.9° C. The reaction mixture was held at 5° C. for 5 min before warming to room temperature. After 30 minutes at room temperature, the reaction was complete. Water (6 L) was added to the reaction mixture over 6 min. An additional 1 L of water was then added and the reaction mixture was stirred for 13 min. The layers were allowed to separate and the organic layer was transferred to a 20 L carboy using an inline filter. The aqueous layer was washed with 500 mL of dichloromethane and the layers separated. This organic layer was combined with the original organic layer in the 20 L carboy. The combined organic layers were concentrated under reduced pressure in a 20 L round bottom flask using a rotovap. The resulting foamy/gummy semi-solid was treated with 6 L of methanol and rotated in a rotovap bath at 50° C. for 20 minutes without a vacuum. During the flask rotation on the rotovap, a yellowish solid began to appear. The flask was removed from the rotovap and the mixture allowed to cool to room temperature overnight. The following morning the mixture was filtered using a stainless steel pan filter equipped with 3× shark skin filter papers. Methanol (1 L) was used to facilitate the transfer. The filter cake was rinsed twice with methanol (2 L). The solid were dried under vacuum in the pan filter by pulling air then nitrogen over the solid overnight. The following morning the solids were washed with 3 L of a 2:1 diethyl ether/ethyl acetate solvent mixture and dried to provide 4-(2-((bis(benzyloxy)phosphoryl)amino)-1-((3,5-dicyano-6-(dimethylamino)-4-ethylpyridin-2-yl)thio)-2-oxoethyl)phenyl methanesulfonate (963 g, 82%) as a tan solid. LCMS m/z=720.3 [M+H]$^+$. $^1$HNMR: (400 MHz, DMSO-d$_6$) δ ppm 10.62-10.52 (m, 1H), 7.63-7.57 (m, 2H), 7.43-7.38 (m, 2H), 7.36-7.27 (m, 8H), 7.26-7.20 (m, 2H), 5.82 (s, 1H), 5.11-4.84 (m, 4H), 3.40 (s, 3H), 3.27 (s, 6H), 2.77 (q, J=7.6 Hz, 2H), 1.22 (t, J=7.6 Hz, 3H).

Step 10: (R)-4-(2-((bis(benzyloxy)phosphoryl)amino)-1-((3,5-dicyano-6-(dimethylamino)-4-ethylpyridin-2-yl)thio)-2-oxoethyl)phenyl methanesulfonate

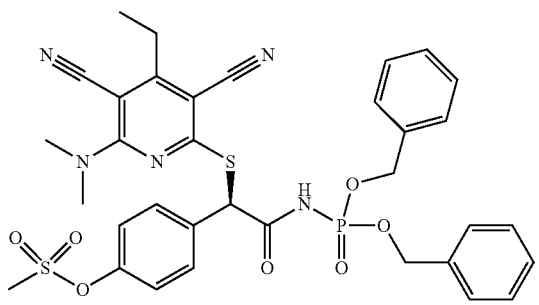 [SMILES: CCc1c(C#N)c(S[C@@H](C(=O)NP(=O)(OCc2ccccc2)OCc2ccccc2)c2ccc(OS(C)(=O)=O)cc2)nc(N(C)C)c1C#N]

4-(2-((bis(benzyloxy)phosphoryl)amino)-1-((3,5-dicyano-6-(dimethylamino)-4-ethylpyridin-2-yl)thio)-2-oxoethyl)phenyl methanesulfonate (1 kg) was dissolved in a 90:10 mixture of acetonitrile:methanol (120 g portions were dissolved in 2 L of 90:10 acetonitrile:methanol). The material was filtered through a glass fiber paper and purified (resolved) on a Varian Prep HPLC, Chiralpak AS 20 u 77×250 mm column, using an isocratic 95:5-CH$_3$CN: CH$_3$OH (50 mM NH$_4$OAc) method to obtain the desired E2 (R)-enantiomer. The standard injection was 9 g of 4-(2-((bis(benzyloxy)phosphoryl)amino)-1-((3,5-dicyano-6-(dimethylamino)-4-ethylpyridin-2-yl)thio)-2-oxoethyl)phenyl methanesulfonate in 150 mL of mobile phase. After processing 1000 g of the racemate using this method, the desired E2 (R)-enantiomer was obtained as a light tan solid with a 99.73% chemical purity (0.17% E1 enantiomer; 0.1% impurity). The material was isolated in a 20 L Buchii flask as a solid containing dark brown/black streaks with residual solvent. Diethyl ether (1.5 L) was added to this material and the solid was dislodged from the flask wall with a large spatula. The flask was swirled to produce an off-white solid suspended in the black ethereal layer. The solid was collected by filtration using a stainless steel pan filter. The Buchii flask was rinsed 3 times with the filtrate in order to transfer as much of the desired enantiomer from the flask as possible. The resulting filtrate was concentrated to dryness and the remaining residue was suspended in diethyl ether (500 mL) to produce a second crop of the desired enantiomer. This solid was collected by filtration in the same pan filter that already contained the first crop. The combined solid was washed with additional diethyl ether (1 L), then allowed to dry overnight under vacuum to provide (R)-4-(2-((bis(benzyloxy)phosphoryl)amino)-1-((3,5-dicyano-6-(dimethylamino)-4-ethylpyridin-2-yl)thio)-2-oxoethyl)phenyl methanesulfonate (296.4 g, 67.6% yield) as a light grey solid. LCMS m/z=720.3 [M+H]$^+$. $^1$HNMR (400 MHz, DMSO-d$_6$) δ ppm 10.57 (d, J=10.8 Hz, 1H), 7.62-7.58 (m, 2H), 7.43-7.38 (m, 2H), 7.34-7.27 (m, 8H), 7.25-7.20 (m, 2H), 5.82 (s, 1H), 5.10-4.84 (m, 4H), 3.39 (s, 3H), 3.26 (s, 6H), 2.76 (q, J=7.6 Hz, 2H), 1.21 (t, J=7.6 Hz, 3H). Chiral HPLC: 99.6% (R)-enantiomer.

Step 11: (R)-(2-((3,5-dicyano-6-(dimethylamino)-4-ethylpyridin-2-yl)thio)-2-(4-((methylsulfonyl)oxy)phenyl)acetyl)phosphoramidic acid

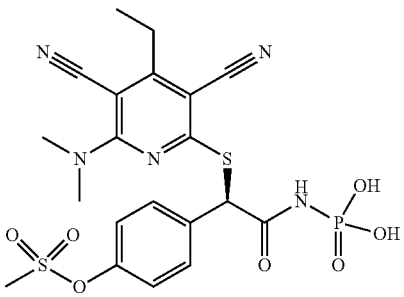 [SMILES: CCc1c(C#N)c(S[C@@H](C(=O)NP(=O)(O)O)c2ccc(OS(C)(=O)=O)cc2)nc(N(C)C)c1C#N]

A 12 L 3-neck round-bottom flask equipped with a mechanical overhead stirrer was charged with (R)-4-(2-((bis(benzyloxy)phosphoryl)amino)-1-((3,5-dicyano6-(dimethylamino)-4-ethylpyridin-2-yl)thio)-2-oxoethyl)phenyl methanesulfonate (200.0 g, 278 mmol) and dichloromethane (2000 mL) to provide a homogeneous orange solution. To this solution at room temperature was added a solution of iodotrimethylsilane (122 g, 611 mmol) in dichloromethane (200 mL) dropwise via addition funnel over 50 minutes. LCMS analysis of an aliquot quenched into MeOH/MeCN after 25 minutes of stirring post iodotrimethylsilane addition indicated desired product plus 4% mono-benzyl phosphate ester. Additional iodotrimethylsilane (1.660 mL, 12.19 mmol) was added and the pale-orange suspension was stirred for 20 minutes. After a total of 2 hours stirring, methanol (200 mL, 4946 mmol) was added dropwise via addition funnel over 28 minutes. An additional 200 mL of dichloromethane was added, and stirring was continued. Further dilution with 200 mL of dichloromethane was needed to aid in stirring. Stirring was continued for 15 minutes before an additional 200 mL of dichloromethane was added (total dichloromethane was 2800 mL). The mixture was mechanically stirred for 2 hours and 45 minutes after methanol addition was completed. The suspension was divided and filtered through 6 disposable polypropylene filter funnels fitted with a polyethylene fritted disc. The solids were repeatedly rinsed with dichloromethane until the red/pink color was absent from the filtrates. The collected white solids were dried in the funnels under vacuum, transferred to a single mortar, and slowly ground into a fine free-flowing white powder. The solid was placed in a vacuum oven for 14 hours with no heating to give (R)-(2-((3,5-dicyano-6-(dimethylamino)-4-ethylpyridin-2-yl)thio)-2-(4-((methylsulfonyl)oxy)phenyl)acetyl)phosphoramidic acid (123.4 g, 82%) as a white solid. LCMS m/z=540.0 [M+H]$^+$. $^1$H NMR (500 MHz, DMSO-d$_6$) δ ppm 11.55 (br s, 2H), 9.74 (br d, J=9.3 Hz, 1H), 7.61 (d, J=8.7 Hz, 2H), 7.39 (d, J=8.7 Hz, 2H), 5.79 (br s, 1H), 3.41 (s, 3H), 3.36 (s, 6H), 2.75 (q, J=7.6 Hz, 2H), 1.20 (t, J=7.6 Hz, 3H). Chiral HPLC:

98.9% (R)-enantiomer.

Figure 7:
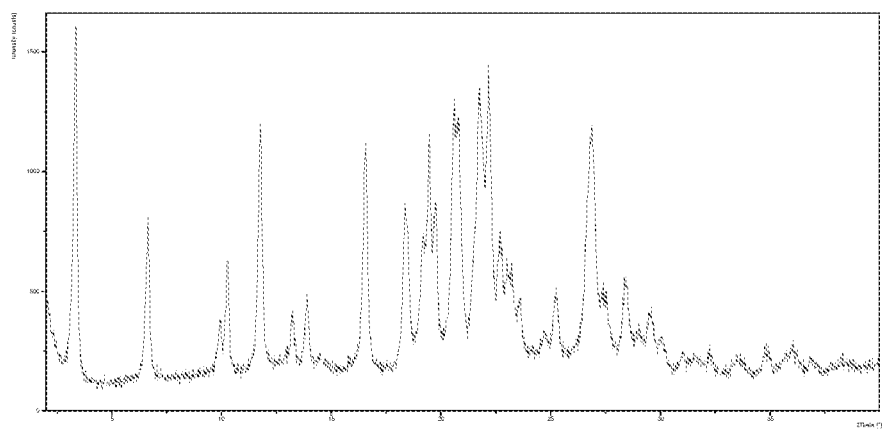
FIG. 7 is an X-Ray Powder Diffraction of the Compound Example 1.

The X-ray powder diffraction (XRPD) pattern of the free-acid parent of Example 1 is shown in FIG. 7 and a summary of the diffraction angles and d-spacings is given in Table III below.

TABLE III

Example 1 Free-Acid Parent Summary of XRPD Diffraction Angles and d-Spacing

| Peak # | Diff. Angle [°2θ] | d-spacing [Å] |
|---|---|---|
| 1 | 3.35 | 26.3903 |
| 2 | 6.64 | 13.3063 |
| 3 | 9.93 | 8.9008 |
| 4 | 10.28 | 8.5977 |
| 5 | 11.77 | 7.5142 |
| 6 | 13.22 | 6.6910 |
| 7 | 13.91 | 6.3629 |
| 8 | 16.56 | 5.3477 |
| 9 | 18.39 | 4.8217 |
| 10 | 19.19 | 4.6219 |
| 11 | 19.47 | 4.5551 |
| 12 | 19.74 | 4.4940 |
| 13 | 20.61 | 4.3065 |
| 14 | 20.78 | 4.2722 |
| 15 | 21.76 | 4.0808 |
| 16 | 22.18 | 4.0049 |
| 17 | 22.71 | 3.9118 |
| 18 | 23.03 | 3.8586 |
| 19 | 23.20 | 3.8311 |
| 20 | 23.58 | 3.7696 |
| 21 | 24.72 | 3.5988 |
| 22 | 25.24 | 3.5261 |
| 23 | 26.86 | 3.3168 |
| 24 | 27.39 | 3.2533 |
| 25 | 28.43 | 3.1370 |
| 26 | 29.06 | 3.0699 |
| 27 | 29.55 | 3.0206 |
| 28 | 30.05 | 2.9714 |
| 29 | 31.05 | 2.8777 |
| 30 | 32.22 | 2.7758 |
| 31 | 33.49 | 2.6734 |
| 32 | 34.80 | 2.5762 |
| 33 | 36.02 | 2.4917 |

Figure 8:
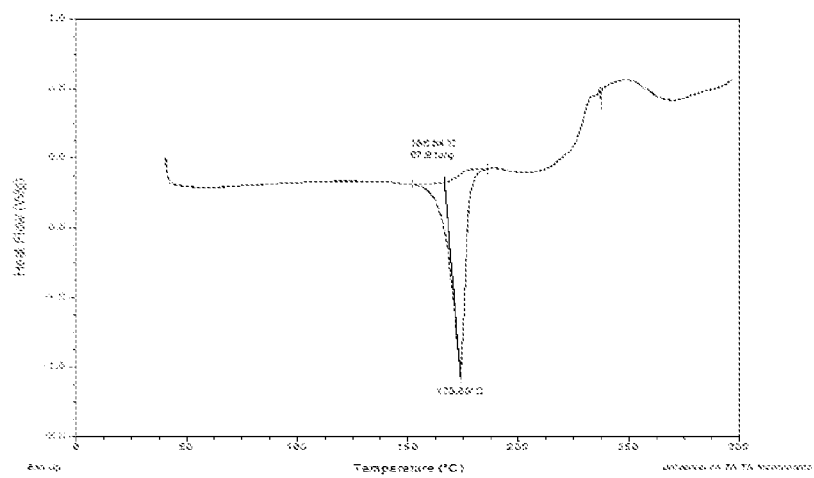
FIG. 8 is a Differential Scanning calorimetry of the Compound of Example 1.

The differential scanning calorimetry (DSC) thermogram of this free-acid parent material same as previous DSC equipment and is shown in FIG. 8. The experiments were conducted using a heating rate of 10° C./min to final temperature of 300° C. in a lightly crimped aluminum pan. This compound has a simple single melting event in DSC, with onset temperature of 166.6° C., peak temperature of 173.8° C. and melting enthalpy of 68 J/g followed by thermal decomposition above 200° C. The compound exhibited negligible weight loss by loss by TGA prior to the decomposition event. A person skilled in the art would recognize that the onset temperature, peak temperature, and enthalpy of the endotherm may vary depending on the experimental conditions.

Figure 9:
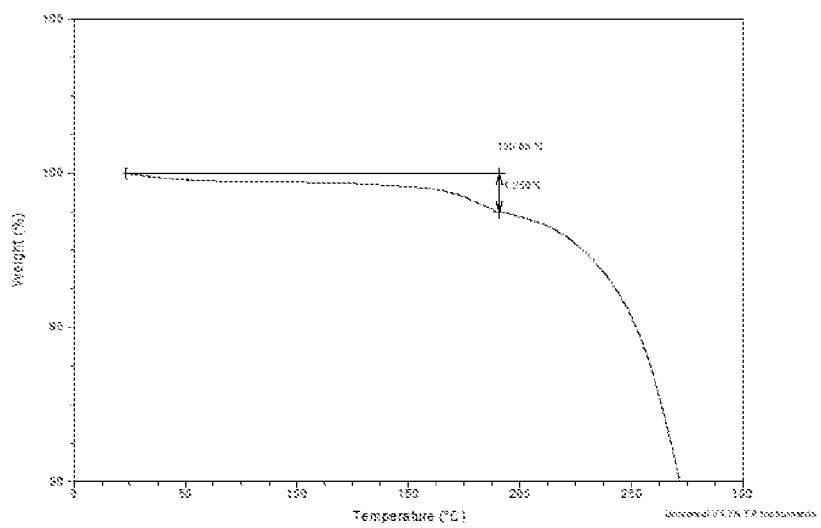
FIG. 9. Thermogravimetric Analysis of the Compound of Example 1.

The thermogravimetric analysis (TGA) thermogram of this free-acid parent material same as previous TGA equipment and is shown in FIG. 9. The experiments were conducted under N₂ purge and a heating rate of 10° C./min to final temperature of 200° C. in an open aluminum pan. The compound exhibited 1.3% weight loss at 190° C. prior to the decomposition event.

Method B (Via Enantioselective Route)

(R)-(2-((3,5-dicyano-6-(dimethylamino)-4-ethylpyridin-2-yl)thio)-2-(4-((methylsulfonyl)oxy)phenyl)acetyl)phosphoramidic acid Step 1: (S)-4-(2-((bis(benzyloxy)phosphoryl)amino)-1-((methylsulfonyl)oxy)-2-oxoethyl)phenyl methanesulfonate

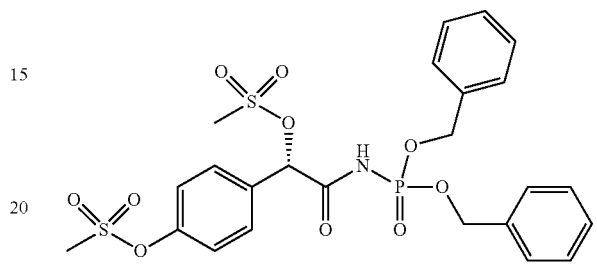

A 500 mL round bottom flask was heated with a heat gun for ~5 minutes while being purged with nitrogen. After cooling to room temperature, the flask was charged with NaH (60% dispersion in mineral oil, 1.089 g, 27.2 mmol) and THF (120 mL). The mixture was cooled to 0° C. and tetrabenzyl diphosphate (7.99 g, 14.85 mmol) was added, followed by portionwise addition of (S)-4-(2-amino-1-((methylsulfonyl)oxy)-2-oxoethyl)phenyl methanesulfonate (4.0 g, 12.37 mmol) over ~3 minutes. The reaction mixture was stirred at 0° C. under a nitrogen balloon. After 2 hours at 0° C., LCMS analysis showed no remaining starting material. The reaction mixture was carefully poured into aqueous 10% citric acid (200 mL) and stirred vigorously. The resulting precipitate was collected by filtration, rinsed with water (3×50 mL) followed by Et₂O (3×50 mL), and dried to constant weight under high vacuum to provide (S)-4-(2-((bis(benzyloxy)phosphoryl)amino)-1-((methylsulfonyl)oxy)-2-oxoethyl)phenyl methanesulfonate (6.57 g, 11.26 mmol, 91% yield) as a white solid. LCMS m/z=584.0 [M+H]⁺. ¹H NMR (400 MHz, DMSO-d₆) δ 10.48 (br s, 1H), 7.69-7.57 (m, 2H), 7.48-7.41 (m, 2H), 7.41-7.22 (m, 10H), 6.11 (s, 1H), 5.13-4.96 (m, 3H), 4.96-4.88 (m, 1H), 3.40 (s, 3H), 3.28 (s, 3H). Chiral SFC: 100% ee.

Step 2: (R)-4-(2-((bis(benzyloxy)phosphoryl)amino)-1-((3,5-dicyano-6-(dimethylamino)-4-ethylpyridin-2-yl)thio)-2-oxoethyl)phenyl methanesulfonate

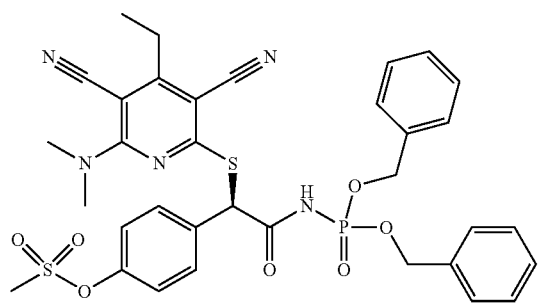 [SMILES: CCc1c(C#N)c(S[C@@H](C(=O)NP(=O)(OCc2ccccc2)OCc2ccccc2)c2ccc(OS(C)(=O)=O)cc2)nc(N(C)C)c1C#N]

To a solution of 2-(dimethylamino)-4-ethyl-6-mercapto-pyridine-3,5-dicarbonitrile (480 mg, 2.066 mmol) in THF (20 mL) at 0° C. was added NaH (83 mg, 2.066 mmol). The resulting mixture was stirred at 0° C. for 30 min, then added dropwise to a solution of (S)-4-(2-((bis(benzyloxy)phosphoryl)amino)-1-((methylsulfonyl)oxy)-2-oxoethyl)phenyl methanesulfonate (1266 mg, 2.170 mmol) in DCM (1 mL) at 0° C. The mixture was allowed to warm to room temperature, stirred for 1 h and quenched with ammonium chloride. The aqueous layer was extracted with DCM and dried over sodium sulfate. The residue was triturated with MeOH to give (R)-4-(2-((bis(benzyloxy)phosphoryl)amino)-1-((3,5-dicyano-6-(dimethylamino)-4-ethylpyridin-2-yl)thio)-2-oxoethyl)phenyl methanesulfonate (908 mg, 1.198 mmol, 58% yield) as an off-white solid. LCMS m/z=720.2 [M+H]$^+$. $^1$H NMR (400 MHz, DMSO-d$_6$) δ 10.56 (d, J=10.8 Hz, 1H), 7.67-7.56 (m, 2H), 7.48-7.39 (m, 2H), 7.37-7.29 (m, 8H), 7.29-7.23 (m, 2H), 5.81 (s, 1H), 5.09-4.86 (m, 4H), 3.39 (s, 3H), 3.27 (s, 6H), 2.76 (q, J=7.6 Hz, 2H), 1.21 (t, J=7.6 Hz, 3H), contaminated with ~25% starting mesylate. Chiral HPLC: 99.3% ee.

Method C (Enantioselective Synthesis of Glycine Salt)

(R)-(2-((3,5-dicyano-6-(dimethylamino)-4-ethylpyridin-2-yl)thio)-2-(4-((methylsulfonyl)oxy)phenyl)acetyl)phosphoramidic acid glycine salt Step 1: (S)-4-(2-amino-1-hydroxy-2-oxoethyl)phenyl methanesulfonate

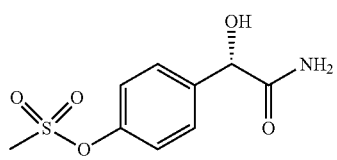 [SMILES: CS(=O)(=O)Oc1ccc([C@H](O)C(N)=O)cc1]

A 1 L JLR, equipped with overhead stirring, was charged with H$_2$O (400 mL) then 2,2-Bis(hydroxyethyl)-(iminotris)-(hydroxymethyl)-methane (10.8 g, 51.4 mmol) and stirred for 3 min with the jacket temperature set to 20° C. A solution made from beta-nicotinamide adenine dinucleotide phosphate disodium salt (NADP+, disodium) (500 mg), ketoreductase enzyme (1.50 g) and H$_2$O (15 mL) was then charged to the JLR and the resultant solution was stirred for 5 min. 4-(2-amino-2-oxoacetyl)phenyl methanesulfonate (50.0 g, 206 mmol), H$_2$O (100 mL) then isopropanol (63.4 mL, 822 mmol) were added and the reaction was heated to 30° C. After stirring for 24 h, the reaction was cooled to 0° C. and 1N aqueous NaOH solution (25.0 mL) was added. The resultant slurry was held for 23 h at 0° C. then the precipitated solids were filtered off by vacuum filtration. The isolated solids were washed twice with H$_2$O (250 mL each wash) then tert-butyl methyl ether (250 mL). After drying under vacuum, the desired product (S)-4-(2-amino-1-hydroxy-2-oxoethyl)phenyl methanesulfonate was isolated as a white to off-white solid (45.0 g, 184 mmol, 89% yield).

LCMS m/z=246.0 [M+H]$^+$. $^1$H NMR: (400 MHz, DMSO-d6) δ ppm 7.54-7.49 (m, 2H), 7.42 (br s, 1H), 7.33-7.28 (m, 2H), 7.21 (br s, 1H), 6.13 (d, J=4.9 Hz, 1H), 4.89 (d, J=4.9 Hz, 1H), 3.37 (s, 3H). Chiral HPLC: >99% ee.

Step 2: (S)-4-(2-amino-1-((methylsulfonyl)oxy)-2-oxoethyl)phenyl methanesulfonate

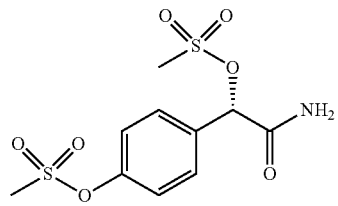 [SMILES: CS(=O)(=O)Oc1ccc([C@H](OS(C)(=O)=O)C(N)=O)cc1]

A 100 mL JLR, equipped with overhead stirring, was charged with (S)-4-(2-amino-1-hydroxy-2-oxoethyl)phenyl methanesulfonate (2.57 g, 10.5 mmol) and N,N-dimethylacetamide (10.3 mL) and stirred with the jacket temperature set to 20° C. 1-methylimidazole (1.51 g, 18.4 mmol) was then added and the reaction was cooled to 0° C. To the yellow solution was slowly added methanesulfonic anhydride (2.56 g, 14.7 mmol) as a solution in N,N-dimethylacetamide (5.12 mL) while keeping the reaction temperature <5° C. The reaction was then warmed to 20° C. and stirred at that temperature for 21 h. Upon completion, the reaction was cooled to 0° C., quenched with addition of H$_2$O (26 mL) over 1 h followed by addition of 5% aqueous sodium sulfate solution (51.5 mL) over 2 h. The resultant slurry was stirred for 20 h then the solids were collected by vacuum filtration. The isolated solids were washed twice with H$_2$O (25 mL each wash) then washed twice with tert-butyl methyl ether (15 mL each wash). After drying under vacuum, the desired product (S)-4-(2-amino-1-((methylsulfonyl)oxy)-2-oxoethyl)phenyl methanesulfonate was isolated as a white solid (3.14 g, 9.71 mmol, 93% yield).

LCMS m/z=324.0 [M+H]$^+$. $^1$H NMR (400 MHz, DMSO-d6) δ ppm 7.86 (s, 1H), 7.63-7.54 (m, 3H), 7.41 (d, J=7.8 Hz, 2H), 5.91 (s, 1H), 3.41 (s, 3H), 3.26 (s, 3H).

Step 3: (S)-4-(2-((dimethoxyphosphoryl)amino)-1-((methylsulfonyl)oxy) oxoethyl)phenyl methanesulfonate

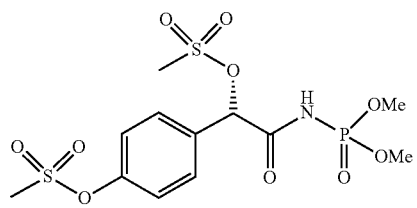

A nitrogen flushed 1 L JLR, equipped with overhead stirring, was charged with tetrahydrofuran (200 mL) followed by (S)-4-(2-amino-1-((methylsulfonyl)oxy)-2-oxoethyl)phenyl methanesulfonate (40 g, 124 mmol) then stirred for approximately 5 min with the jacket temperature set to 20° C. The slurry was then cooled to 0° C. and chloro-dimethylphosphate (20 mL, 186 mmol) was charged to the vessel. After stirring for 1 h, a 1M solution of lithium tert-butoxide in tetrahydrofuran (272 mL, 272 mmol) was slowly added while keeping the reaction temperature <5° C. The reaction was stirred for approximately 1 h and determined to be incomplete via HPLC analysis. Additional chloro-dimethylphosphate (6.3 mL, 58 mmol) was charged to the reaction followed by a slow addition of 1M solution of lithium tert-butoxide in tetrahydrofuran (37.1 mL, 37.1 mmol). The reaction was stirred for 30 min then quenched via slow addition of 10% citric acid aqueous solution (w/w, 40 mL) while keeping the reaction temperature <5° C. The reaction was stirred for approximately 15 min then additional 10% citric acid aqueous solution (w/w, 80 mL) was charged while keeping the reaction temperature <5° C. The temperature was increased to 20° C. and held at that temperature for approximately 30 min. The reaction mixture was then cooled to 0° C. and held for approximately 14 h. The reaction was concentrated via vacuum distillation to approximately 300 mL total volume. Isopropanol (380 mL) was charged to the reaction and the reaction was stirred at 20° C. for 2 h. The reaction was concentrated via vacuum distillation to approximately 520 mL total volume, then H$_2$O (80 mL) and isopropanol (80 mL) were added and the reaction was cooled to 0° C. After stirring for 19 h, the product slurry was transferred to a filter dryer. The mother liquors were filtered away using nitrogen pressure. The reactor was rinsed with H$_2$O (400 mL) then transferred to the filter dryer to wash the isolated solids. Nitrogen pressure was used to push the wash through the product filter cake. The reactor was rinsed with isopropanol (400 mL) then transferred to the filter dryer to wash the isolated solids. Nitrogen pressure was used to push the wash through the product filter cake. The product solids were then washed with tert-butyl methyl ether (200 mL). The isolated solids were dried under nitrogen for 23 hours then dried under vacuum at 20° C. for 21 h to yield the desired product (S)-4-(2-((dimethoxyphosphoryl)amino)-1-((methylsulfonyl)oxy)-2-oxoethyl)phenyl methanesulfonate as a white solid (35.1 g, 81 mmol, 66% yield). LCMS m/z=454.1 [M+Na]$^+$. $^1$H NMR (400 MHz, DMSO-d6) δ ppm 10.28 (br s, 1H), 7.60-7.68 (m, 2H), 7.44-7.51 (m, 2H), 6.07 (s, 1H), 3.67 (d, J=12 Hz, 3H), 3.57 (d, J=12 Hz, 3H), 3.43 (s, 3H), 3.30 (s, 3H). Chiral HPLC: >99% ee.

Step 4: (R)-4-(1-((3,5-dicyano-6-(dimethylamino)-4-ethylpyridin-2-yl)thio)-2-((dimethoxyphosphoryl)amino)-2-oxoethyl)phenyl methanesulfonate

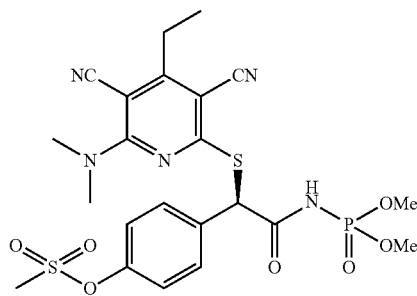 [SMILES: CCc1c(C#N)c(S[C@@H](C(=O)NP(=O)(OC)OC)c2ccc(OS(C)(=O)=O)cc2)nc(N(C)C)c1C#N]

A nitrogen flushed 1 L JLR, equipped with overhead stirring, was charged with H$_2$O (338 mL) and sodium carbonate (5.18 g, 48.9 mmol) then stirred at 20° C. The walls of the reaction vessel were rinsed with additional H$_2$O (42.0 mL) then the mixture was stirred for 10 min. Acetone (170 mL) was charged followed by 2-(dimethylamino)-4-ethyl-6-mercaptopyridine-3,5-dicarbonitrile (22.7 g, 98.0 mmol) and additional acetone (42.0 mL). The mixture was stirred for approximately 1 h then (S)-4-(2-((dimethoxyphosphoryl)amino)-1-((methylsulfonyl)oxy)-2-oxoethyl) phenyl methanesulfonate (42.2 g, 98.0 mmol) was added in one portion. The reaction was stirred for 2 h then the precipitated solids were collected by vacuum filtration. The isolated solids were washed twice with H$_2$O (126 mL each wash), then twice with isopropanol (210 mL each wash), then tert-butyl methyl ether (420 mL) and blown dry with a stream of nitrogen for 15 h. The product filter cake was then reslurried with tert-butyl methyl ether (336 mL). After mixing for approximately 10 min, the solids were filtered to dryness and rinsed with additional tert-butyl methyl ether (126 mL). After drying under vacuum, the desired product (R)-4-(1-((3,5-dicyano-6-(dimethylamino)-4-ethylpyridin-2-yl)thio)-2-((dimethoxyphosphoryl)amino)-2-oxoethyl) phenyl methanesulfonate was collected to yield an off-white solid (50.6 g, 88.0 mmol, 90% yield).

LCMS m/z=568.1 [M+H]$^+$. $^1$H NMR (400 MHz, DMSO-d6) δ ppm 10.33-10.43 (m, 1H), 7.55-7.66 (m, 2H), 7.36-7.48 (m, 2H), 5.81 (br s, 1H), 3.64 (d, J=12 Hz, 3H), 3.52 (d, J=12 Hz, 3H), 3.42 (s, 3H), 3.37 (s, 6H), 2.77 (q, J=8 Hz, 2H), 1.21 (t, J=8 Hz, 3H). Chiral HPLC: >99% ee.

Step 5: (R)-(2-((3,5-dicyano-6-(dimethylamino)-4-ethylpyridin-2-yl)thio)-2-(4-((methylsulfonyl)oxy)phenyl)acetyl)phosphoramidic acid DMF hemi-solvate

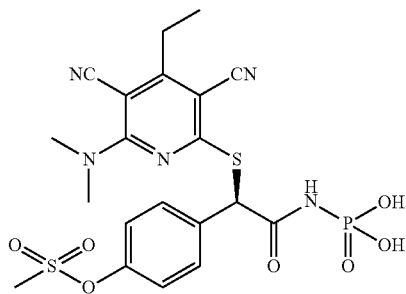 [SMILES: CCc1c(C#N)c(S[C@@H](C(=O)NP(=O)(O)O)c2ccc(OS(C)(=O)=O)cc2)nc(N(C)C)c1C#N]

A nitrogen-purged 2 L JLR was charged with dichloromethane (250 mL) and (R)-4-(1-((3,5-dicyano-6-(dimethylamino)-4-ethylpyridin-2-yl)thio)-2-((dimethoxyphosphoryl)amino)-2-oxoethyl)phenyl methanesulfonate (65.0 g, 115 mmol), then the vessel walls were washed with additional dichloromethane (100 mL) to produce a homogeneous tan solution. After cooling this solution to 0° C., iodotrimethylsilane (42.1 mL, 309 mmol) was charged while keeping the internal temperature <5° C. The resulting brown reaction mixture was stirred for 1 h at 0° C. HPLC analysis of the reaction mixture indicated the reaction was incomplete, so an additional iodotrimethylsilane (3.12 mL, 22.9 mmol) was charged. After stirring for 13 minutes, the reaction was quenched by adding approximately 50% of the DMF quench solution (91 mL) while keeping the internal temperature <5° C. (Note: DMF quench solution was prepared by adding H$_2$O (3.30 mL, 183 mmol) to anhydrous DMF (179 mL)). The reaction mixture was held at 0° C. for 3 minutes, then the crystallization was seeded with (R)-(2-((3,5-dicyano-6-(dimethylamino)-4-ethylpyridin-2-yl)thio)-2-(4-((methylsulfonyl)oxy)phenyl)acetyl)phosphoramidic acid DMF hemi-solvate (165 mg) slurried in dichloromethane (6.50 mL) and held at 0° C. for approximately 30 minutes. The thin slurry was then further diluted via portionwise addition of dichloromethane (650 mL) then stirred at 0° C. for approximately 30 minutes. The remaining approximately 50% of the DMF quench solution (91 mL) was charged slowly while maintaining the internal temperature <5° C. Upon completion of the addition, the jacket temperature was raised to 20° C. at a rate of 2° C./min and held at 20° C. for approximately 45 min. The reaction slurry was further diluted with dichloromethane (650 mL) and stirred for 12 h. The precipitated solids were collected by vacuum filtration then washed twice with dichloromethane (325 mL per wash). The solids were reslurried with ethyl acetate (325 mL) for approximately 2.5 h at 20° C., isolated by vacuum filtration, then dried under vacuum to yield (R)-(2-((3,5-dicyano-6-(dimethylamino)-4-ethylpyridin-2-yl)thio)-2-(4-((methylsulfonyl)oxy)phenyl)acetyl)phosphoramidic acid DMF hemi-solvate (58.4 g, 101 mmol, 89% yield) as a white to off-white product. 1H NMR shows product:DMF ratio as 1:0.8.

LCMS m/z=540.0 [M+H]$^+$. $^1$H NMR (400 MHz, DMSO-d6) δ ppm 10.77-12.19 (br s, 1H), 9.75 (br d, J=9.5 Hz, 1H), 7.96 (s, 0.8H, DMF), 7.58-7.65 (m, 2H), 7.31-7.46 (m, 2H), 5.80 (br s, 1H), 3.42 (s, 3H), 3.37 (m, 6H), 2.90 (s, 2.8H, DMF), 2.74 (m, 4.8H, includes DMF), 1.21 (t, J=7.5 Hz, 3H). Chiral HPLC: >99% ee.

Step 6: (R)-(2-((3,5-dicyano-6-(dimethylamino)-4-ethylpyridin-2-yl)thio)-2-(4-((methylsulfonyl)oxy)phenyl)acetyl)phosphoramidic acid glycine salt

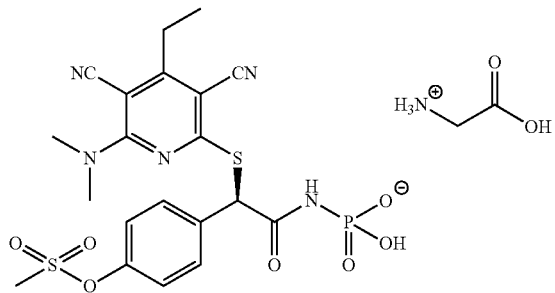 [SMILES: CCc1c(C#N)c(S[C@@H](C(=O)NP(=O)([O-])O)c2ccc(OS(C)(=O)=O)cc2)nc(N(C)C)c1C#N ; [NH3+]CC(=O)O]

The process was carried out in a pair of 16 L JLRs, noted as Vessel A and Vessel B, each equipped with overhead stirring. Micronized glycine (71.5 g, 0.952 mol), dichloromethane (9 L) and methanol (896.5 mL) were charged to Vessel A and the same charges were repeated to Vessel B. The mixtures were stirred at 25° C. Then, a slurry of (R)-(2-((3,5-dicyano-6-(dimethylamino)-4-ethylpyridin-2-yl)thio)-2-(4-((methylsulfonyl)oxy)phenyl)acetyl)phosphoramidic acid DMF hemi-solvate (137.5 g, 0.238 mol) in ethyl acetate (1.1 L) was charged to Vessel A over at least 15 min. The slurry container was rinsed with ethyl acetate (550 mL) then this rinse was transferred to the reactor. The slurry charge and ethyl acetate rinse were repeated to Vessel B. The crystallizations in Vessel A and Vessel B were seeded with (R)-(2-((3,5-dicyano-6-(dimethylamino)-4-ethylpyridin-2-yl)thio)-2-(4 ((methylsulfonyl)oxy)phenyl)acetyl)phosphoramidic acid glycine salt (5.5 g). The process of a slow addition of (R)-(2-((3,5-dicyano-6-(dimethylamino)-4-ethylpyridin-2-yl)thio)-2-(4-((methylsulfonyl)oxy)phenyl)acetyl)phosphoramidic acid DMF hemi-solvate (137.5 g, 0.238 mol) in ethyl acetate (1.1 L), ethyl acetate (550 mL) container rinse, and rinse transfer to Vessel A and Vessel B was repeated three times to each reactor after seeding. The slurries were stirred at 25° C. overnight and the reaction was complete. The slurry mixtures of both Vessel A and B were emptied into a stainless-steel pan filter equipped with filter paper. The mother liquors were filtered away using vacuum pressure. Vessel A and Vessel B were each rinsed with ethyl acetate (3.3 L) then transferred to the pan filter to wash the isolated solids and filtered. The rinses to Vessel A and Vessel B with ethyl acetate were repeated a second time. Vacuum pressure was used to push the washes through the product filter cake. The isolated solids were dried under vacuum at 50° C. until LOD analysis gave <1% to yield (R)-2-((3,5-dicyano-6-(dimethylamino)-4-ethylpyridin-2-yl)thio)-2-(4-((methylsulfonyl)oxy)phenyl)acetyl)phosphoramidic acid glycine salt (1101 g, 1.791 mol, 92.5% yield) as a white solid. 1H NMR shows product:glycine ratio as 1:1.

LCMS m/z=540.2 [M+H]$^+$. $^1$H NMR (400 MHz, DMSO-d6) δ ppm 9.41 (br d, J=7.50 Hz, 1H), 7.66 (br d, J=8.0 Hz, 2H), 7.36 (br d, J=8.0 Hz, 2H), 5.80 (s, 1H), 3.48 (s, 2H), 3.41 (s, 3H), 3.34 (s, 7H), 2.74 (q, J=7.5 Hz, 3H), 1.19 (t, J=7.5 Hz, 3H). Chiral HPLC: >99% ee.

Crystalline compound of Example 1, glycine compound with (R)-(2-((3,5-dicyano-6-(dimethylamino)-4-ethylpyridin-2-yl)thio)-2-(4-((methylsulfonyl)oxy)phenyl)acetyl) phosphoramidic acid (1:1).

The X-ray powder diffraction (XRPD) pattern of this material is shown in FIG. 1 and a summary of the diffraction angles and d-spacings is given in Table I below. The XRPD analysis was conducted on a PANanalytical X'Pert Pro Diffractometer on Si zero-background wafers using X'celerator™ RTMS (Real Time Multi-Strip) detector. The acquisition conditions included: Cu K$_\alpha$ radiation, Wavelength (λ): 1.5405980 Å, generator tension: 45 kV, generator current: 40 mA, step size: 0.0167° 2θ. Configuration on the incidental beam side: 10 mm programmable divergence slit, 0.02 rad Soller slits, anti-scatter slit (0.5°), and 10 mm beam mask. Configuration on the diffracted beam side: 10 mm programmable anti-scatter slit assembly (X'celerator module) and 0.02 rad Soller slit.

TABLE I

| XRPD Summay of Diffraction Angles and d-Spacing | | |
|---|---|---|
| Peak # | Diff. Angle [°2θ] | d-spacing [Å] |
| 1 | 5.42 | 16.3027 |
| 2 | 5.78 | 15.2672 |
| 3 | 7.44 | 11.8749 |
| 4 | 9.59 | 9.2110 |
| 5 | 10.56 | 8.3679 |
| 6 | 10.81 | 8.1745 |
| 7 | 11.55 | 7.6557 |
| 8 | 13.04 | 6.7854 |
| 9 | 14.46 | 6.1218 |
| 10 | 14.84 | 5.9641 |
| 11 | 15.56 | 5.6903 |
| 12 | 16.25 | 5.4518 |
| 13 | 17.01 | 5.2072 |
| 14 | 18.32 | 4.8394 |
| 15 | 18.82 | 4.7116 |
| 16 | 19.00 | 4.6665 |
| 17 | 19.20 | 4.6182 |
| 18 | 19.60 | 4.5246 |
| 19 | 20.49 | 4.3310 |
| 20 | 20.99 | 4.2287 |
| 21 | 21.18 | 4.1924 |
| 22 | 21.54 | 4.1216 |
| 23 | 21.69 | 4.0934 |
| 24 | 22.34 | 3.9755 |
| 25 | 22.65 | 3.9233 |
| 26 | 23.20 | 3.8313 |
| 27 | 23.95 | 3.7127 |
| 28 | 24.42 | 3.6426 |
| 29 | 24.99 | 3.5610 |
| 30 | 25.17 | 3.5354 |

TABLE I-continued

XRPD Summay of Diffraction Angles and d-Spacing

| Peak # | Diff. Angle [°2θ] | d-spacing [Å] |
|---|---|---|
| 31 | 26.22 | 3.3958 |
| 32 | 26.54 | 3.3559 |

Figure 2:
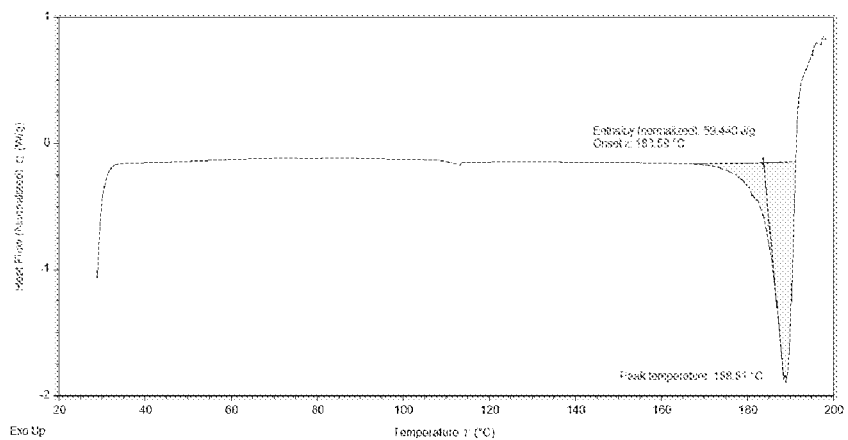
FIG. 2 is a Differential Scanning calorimetry of the glycinate salt of the Compound of Example 1.

The differential scanning calorimetry (DSC) thermogram of this material was recorded on a TA Instruments Discovery Differential Scanning calorimeter equipped with an autosampler and a refrigerated cooling system under 40 mL/min $N_2$ purge and is shown in FIG. 2. The experiments were conducted using a heating rate of 10° C./min to final temperature of 200° C. in a lightly crimped aluminum pan. This compound has a simple single melting event in DSC, with onset temperature of 183.6° C., peak temperature of 188.8° C. and melting enthalpy of 64 J/g. The determination of melting enthalpy is not reliable due to the immediate thermal decomposition post melting. The compound exhibited negligible weight loss by loss by TGA prior to the decomposition event. A person skilled in the art would recognize that the onset temperature, peak temperature, and enthalpy of the endotherm may vary depending on the experimental conditions.

Figure 3:
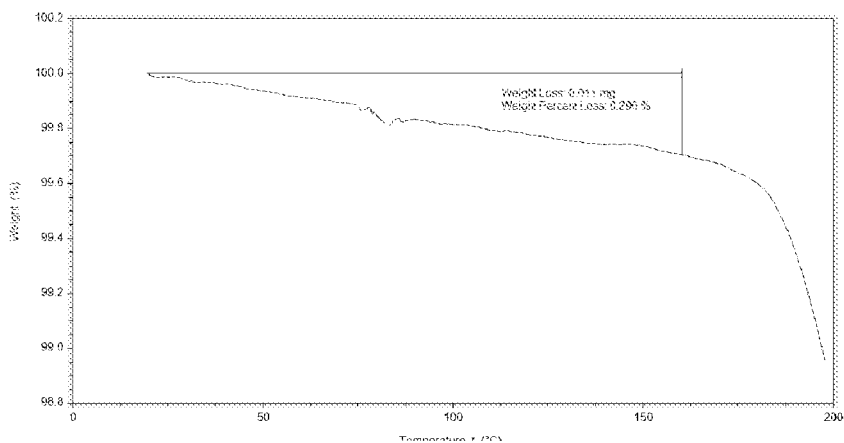
FIG. 3 is a Differential Scanning calorimetry of the glycinate salt of the Compound of Example 1.

The thermogravimetric analysis (TGA) thermogram of this material was recorded on a TA Instruments Discovery Thermogravimetric Analyzer and is shown in FIG. 3. The experiments were conducted under $N_2$ purge and a heating rate of 10° C./min to final temperature of 200° C. in an open aluminum pan. The compound exhibited 0.3% weight loss at 160° C. prior to the decomposition event.

Each of the general points in the above paragraphs pertaining to XRPD, DSC, and TGA are applicable to each of the XRPD, DSC, and TGA analyses performed in this application. In addition, in all of the XRPD data reported in this case, the data has a plus or minus 0.2 accuracy.

Step 7: (R)-(2-((3,5-dicyano-6-(dimethylamino)-4-ethylpyridin-2-yl)thio)-2-(4-((methylsulfonyl)oxy)phenyl)acetyl)phosphoramidic acid glycine salt monohydrate

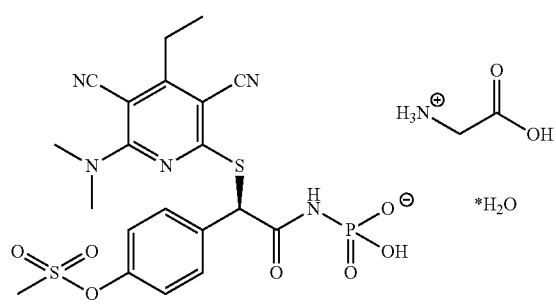 [SMILES: CCc1c(C#N)c(S[C@@H](C(=O)NP(=O)([O-])O)c2ccc(OS(C)(=O)=O)cc2)nc(N(C)C)c1C#N ; [NH3+]CC(=O)O]

A 50 mL JLR fitted with overhead stirring was charged with (R)-(2-((3,5-dicyano-6-(dimethylamino)-4-ethylpyridin-2-yl)thio)-2-(4-((methylsulfonyl)oxy)phenyl)acetyl) phosphoramidic acid DMF hemi-solvate (1.5 g, 2.54 mmol) and ethyl acetate (37.5 mL). While stirring, the reactor's jacket was heated to 50° C. at 1° C./min and maintained at 50° C. for 95 minutes. A solution of 2M glycine in water (2.67 mmol glycine) was loaded into an attached 10 mL dosing unit. 2M glycine in water (1.33 mL) was charged to the reaction mixture over 90 minutes. After the charge, the mixture was held for 60 minutes then it was cooled to 5° C. at 0.25° C./min. The reaction mixture was held at 5° C. for 60 minutes. The reaction mixture was then programmed overnight to complete two temperature cycles of heat to 50° C. at 1° C./min, hold at 50° C., cool to 5° C. at 0.25° C./min, and hold at 5° C. for 60 minutes. The reaction mixture was held at 5° C. for 4.5 days and then filtered through a disposable filter funnel. The wet cake of the reaction solids was rinsed twice with ethyl acetate (2×9 mL) and filtered. The solid was placed overnight in a vacuum oven at 25° C. and dried to produce (R)-(2-((3,5-dicyano-6-(dimethylamino)-4-ethylpyridin-2-yl)thio)-2-(4-((methylsulfonyl)oxy)phenyl)acetyl)phosphoramidic acid hydrate glycine salt (1.55 g, 2.45 mmol) as a white solid.

$^1$H NMR (400 MHz, DMSO-d6) δ ppm 9.34 (s, 1H), 7.65 (br d, J=7.5 Hz, 2H), 7.36 (br d, J=7.5 Hz, 2H), 5.79 (br s, 1H), 3.40 (s, 6H), 3.35 (br s, 9H), 2.74 (q, J=7.0 Hz, 2H), 1.19 (t, J=7.0 Hz, 3H). Chiral HPLC: >99% ee.

Figure 4:
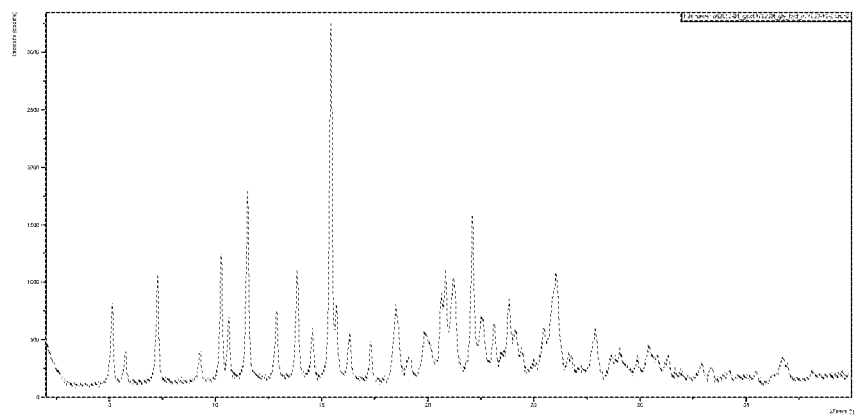
FIG. 4 is an X-Ray Powder Diffraction of the Glycinate Salt of the Compound of Example 1, monohydrate.

The X-ray powder diffraction (XRPD) pattern of the mono-hydrate glycinate salt of Example 1 is shown in FIG. 4 and a summary of the diffraction angles and d-spacings is given in Table II below.

TABLE II

Example 1 Mono-Hydrate Glycinate Salt Summay of XRPD Diffraction Angles and d-Spacing

| Peak # | Diff. Angle [°2θ] | d-spacing [Å] |
|---|---|---|
| 1 | 5.13 | 17.2011 |
| 2 | 5.75 | 15.3532 |
| 3 | 7.27 | 12.1458 |
| 4 | 9.28 | 9.5245 |
| 5 | 10.26 | 8.6117 |
| 6 | 10.61 | 8.3277 |
| 7 | 11.52 | 7.6772 |
| 8 | 12.87 | 6.8726 |
| 9 | 13.86 | 6.3858 |
| 10 | 14.56 | 6.0794 |
| 11 | 15.43 | 5.7389 |
| 12 | 16.31 | 5.4293 |
| 13 | 17.32 | 5.1171 |
| 14 | 18.52 | 4.7872 |
| 15 | 19.15 | 4.6299 |
| 16 | 19.89 | 4.4604 |
| 17 | 20.84 | 4.2586 |
| 18 | 21.23 | 4.1824 |
| 19 | 22.11 | 4.0168 |
| 20 | 22.55 | 3.9404 |
| 21 | 23.13 | 3.8421 |
| 22 | 23.83 | 3.7305 |
| 23 | 24.13 | 3.6847 |
| 24 | 25.47 | 3.4942 |
| 25 | 26.06 | 3.4171 |
| 26 | 27.91 | 3.1941 |
| 27 | 28.65 | 3.1137 |
| 28 | 29.05 | 3.0716 |
| 29 | 29.90 | 2.9860 |
| 30 | 30.42 | 2.9363 |
| 31 | 30.82 | 2.8990 |
| 32 | 31.34 | 2.8522 |
| 33 | 32.91 | 2.7196 |
| 34 | 33.38 | 2.6825 |
| 35 | 36.72 | 2.4456 |

Figure 5:
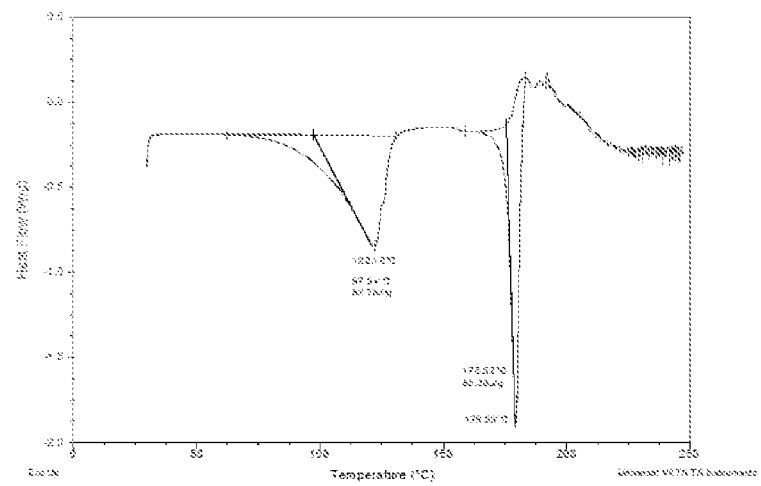
FIG. 5 is a Differential Scanning calorimetry of the Glycinate Salt of the Compound of Example 1, monohydrate.

The differential scanning calorimetry (DSC) thermogram of this hydrated glycinate salt material same as previous DSC equipment is shown in FIG. 5. The experiments were conducted using a heating rate of 10° C./min to final temperature of 250° C. in a lightly crimped aluminum pan. This compound has a broad endotherm dehydration event from 40-140° C. followed by a sharp melt endotherm with onset temperature of 175.5° C., peak temperature of 179.3° C. and melting enthalpy of 52 J/g. The determination of melting enthalpy is not reliable due to the immediate thermal decomposition post melting. A person skilled in the art would recognize that the onset temperature, peak temperature, and enthalpy of the endotherm may vary depending on the experimental conditions.

Figure 6:
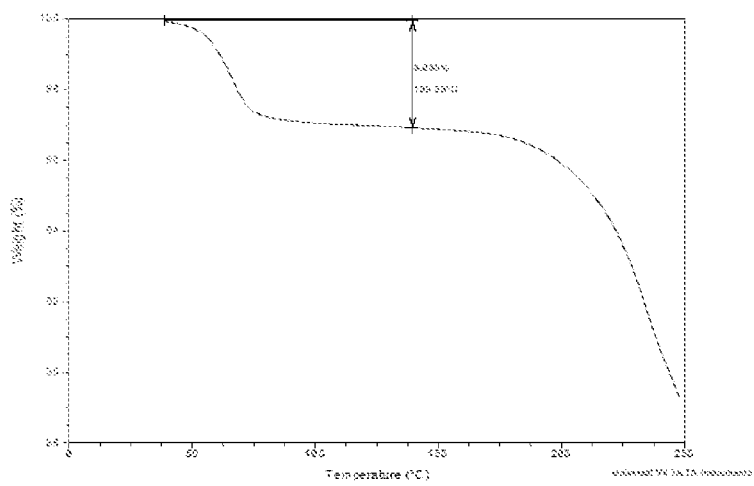
FIG. 6 is a Thermogravimetric Analysis of the Glycinate Salt of the Compound of Example 1, monohydrate.

The thermogravimetric analysis (TGA) thermogram of this hydrated glycinate salt material same as previous TGA equipment is shown in FIG. 6. The experiments were conducted under $N_2$ purge and a heating rate of 10° C./min to final temperature of 250° C. in an open aluminum pan. The compound exhibited 3.0% weight loss from 40 to 140° C. indicative of a mono-hydrate morphic form prior to the decomposition event.

Example 2

(R)-4-(2-amino-1-((3,5-dicyano-6-(dimethylamino)-4-ethylpyridin-2-yl)thio) oxoethyl)phenyl methanesulfonate Step 1: 4-(2-amino-2-oxoacetyl)phenyl methanesulfonate

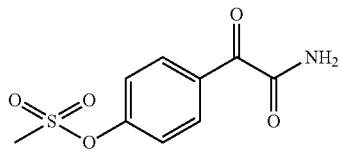 [SMILES: CS(=O)(=O)Oc1ccc(C(=O)C(N)=O)cc1]

To a stirred suspension of 4-(2-amino-1-hydroxy-2-oxoethyl)phenyl methanesulfonate (50 g, 204 mmol) in acetonitrile (3000 mL) under nitrogen at room temperature was added manganese dioxide (248 g, 2854 mmol) in one charge over 1 minute. The reaction mixture was heated at 70° C. for 16 hours and then heated at 80° C. for 48 hours. The reaction mixture was cooled to room temperature, filtered through celite, and the celite bed washed with acetonitrile (2000 mL). The filtrate was concentrated under reduced pressure to give 44 g of the desired crude product as an off-white solid. Analysis of the material by UPLC MS indicated 46.67% area under the curve corresponded to the product mass and 48.26% area under the curve corresponded to the starting material mass. The crude product/starting material mixture was subjected to an oxidation reaction using PCC as described below.

To a stirred solution containing a mixture of 4-(2-amino-1-hydroxy-2-oxoethyl)phenyl methanesulfonate and 4-(2-amino-2-oxoacetyl)phenyl methanesulfonate (42.0 g, 86 mmol) in tetrahydrofuran (THF) (2.4 L) under nitrogen at room temperature was added PCC (18.53 g, 86 mmol) by mixing with celite in one charge. The reaction mixture was stirred at room temperature for 2 hours. The reaction mixture was filtered through celite and the celite bed was washed with (2000 mL) of THF. The filtrate was concentrated in vacuo to give the crude product as dark brown solid. The crude product was dissolved in a mixture of 100 mL of methanol and 150 mL of DCM and absorbed onto 400 g of silica (60-120 mesh). The resulting material was filtered through 4 kg of silica (230-400 mesh) and the silica bed was washed with (3000 mL) of ethyl acetate. The filtrate was concentrated in vacuo to provide 4-(2-amino-2-oxoacetyl) phenyl methanesulfonate (26 g, 52%) as an off-white solid.

LCMS m/z=244.0 [M+H]⁺. ¹HNMR (400 MHz, DMSO-d6) δ ppm 8.37 (br s, 1H), 8.13-8.09 (m, 2H), 8.06 (br s, 1H), 7.58-7.54 (m, 2H), 3.49 (s, 3H).

Step 2: (S)-4-(2-amino-1-hydroxy-2-oxoethyl)phenyl methanesulfonate

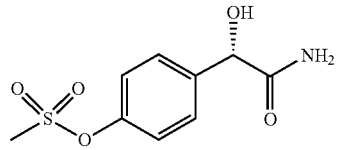 [SMILES: CS(=O)(=O)Oc1ccc([C@H](O)C(N)=O)cc1]

A 500 mL round-bottom flask, equipped with an oversized stir bar, was charged with 4-(2-amino-2-oxoacetyl)phenyl methanesulfonate (5.0 g, 20.56 mmol) and isopropanol (10 mL). To the resulting mixture was added 80 mL of a 1.25 mg/mL solution of beta-nicotinamide adenine dinucleotide phosphate disodium salt (NADP+, disodium) (100 mg, 20.56 mmol) in 0.1 M KPi pH 7.0 buffer followed by SynBio Ketoreductase Enzyme Seq ID S00000617 (300 mg, 20.56 mmol). The resulting slurry was stirred vigorously at room temperature. After a total of 46 hours, the aqueous layer was saturated with solid KCl and the mixture was diluted with EtOAc (200 mL). An emulsion formed, therefore, the mixture was filtered through a pad of Celite® and rinsed through with copious EtOAc (3×75 mL) giving clear distinct layers. The organic layer was washed with brine and the combined aqueous layers were back-extracted with EtOAc (2×75 mL). The combined organics were dried over $Na_2SO_4$, filtered and concentrated under reduced pressure. The residue was dried to constant weight under high vacuum to provide (S)-4-(2-amino-1-hydroxy-2-oxoethyl)phenyl methanesulfonate (4.40 g, 87% yield) as a white solid. LCMS m/z=246.0 [M+H]⁺. ¹HNMR: (400 MHz, DMSO-d6) δ ppm 7.54-7.49 (m, 2H), 7.42 (br s, 1H), 7.33-7.28 (m, 2H), 7.21 (br s, 1H), 6.13 (d, J=4.9 Hz, 1H), 4.89 (d, J=4.9 Hz, 1H), 3.37 (s, 3H). Chiral HPLC: >99% ee.

Step 3: (S)-4-(2-amino-1-((methylsulfonyl)oxy)-2-oxoethyl)phenyl methanesulfonate

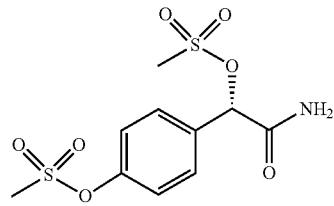 [SMILES: CS(=O)(=O)Oc1ccc([C@H](OS(C)(=O)=O)C(N)=O)cc1]

To a cold (0° C.) suspension of (S)-4-(2-amino-1-hydroxy-2-oxoethyl)phenyl methanesulfonate (4.3 g, 17.53 mmol) in dichloromethane (DCM) (40 mL) was added Ms-Cl (1.639 mL, 21.04 mmol) over ~1 minute, followed by TEA (3.67 mL, 26.3 mmol) over ~3 minutes. After 2 hours, LCMS showed ~15% starting material (no additional progression after 3 hours), so the reaction mixture was re-cooled to 0° C. and additional portions of Ms-Cl (0.410 mL, 5.26 mmol) and TEA (1.222 mL, 8.77 mmol) were added. The ice bath was removed and the reaction was allowed to warm to room temperature. After an additional 30 minutes, the reaction mixture was quenched with saturated aqueous NaHCO₃ (50 mL) and stirred vigorously. The resulting suspension/emulsion was filtered and the solid was rinsed sequentially with water (3×30 mL) and diethyl ether (3×30 mL), and dried to constant weight under high vacuum to provide (S)-4-(2-amino-1-((methylsulfonyl)oxy) oxoethyl)phenyl methanesulfonate (4.44 g, 78% yield) as a slightly off-white solid. LCMS m/z=324.0 [M+H]⁺. ¹HNMR (400 MHz, DMSO-d6) δ ppm 7.86 (s, 1H), 7.63-7.54 (m, 3H), 7.41 (d, J=7.8 Hz, 2H), 5.91 (s, 1H), 3.41 (s, 3H), 3.26 (s, 3H).

Step 4: (R)-4-(2-amino-1-((3,5-dicyano-6-(dimethylamino)-4-ethylpyridin-2-yl)thio) oxoethyl)phenyl methanesulfonate

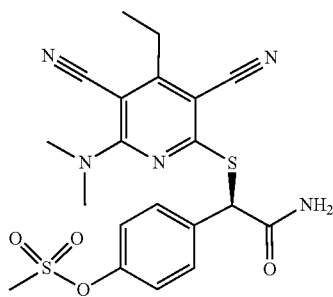 [SMILES: CCc1c(C#N)c(S[C@@H](C(N)=O)c2ccc(OS(C)(=O)=O)cc2)nc(N(C)C)c1C#N]

To a suspension of 2-(dimethylamino)-4-ethyl-6-mercaptopyridine-3,5-dicarbonitrile (1.437 g, 6.19 mmol) in ethyl acetate (50 mL) was added iPr₂EtN (1.350 mL, 7.73 mmol). The orange suspension was stirred at room temperature. After 30 minutes, a suspension of (S)-4-(2-amino-1-((methylsulfonyl)oxy)-2-oxoethyl)phenyl methanesulfonate (2.0 g, 6.19 mmol) in ethyl acetate (30 mL) was added and the resulting orange suspension was stirred at room temperature. After 4 hours, the inside of the flask was scratched with a spatula which initiated precipitation of product. The resulting suspension was stirred an additional 30 minutes, then cooled to 0° C. The precipitate was collected by filtration using a filter funnel, rinsed sequentially with cold (0° C.) EtOAc (2×20 mL), water (2×10 mL), cold (0° C.) EtOAc (2×20 mL), followed by diethyl ether (2×10 mL). The solid was dried for 48 hours under high vacuum to provide (R)-4-(2-amino-1-((3,5-dicyano-6-(dimethylamino)-4-ethylpyridin-2-yl)thio)-2-oxoethyl)phenyl methanesulfonate (1.37 g, 48.2% yield) as an off-white solid. LCMS m/z=460.2 [M+H]⁺. ¹H NMR (400 MHz, DMSO-d₆) δ ppm 7.96 (s, 1H), 7.62 (d, J=8.8 Hz, 2H), 7.42-7.31 (m, 3H), 5.66 (s, 1H), 3.39 (s, 3H), 3.33 (s, 6H), 2.75 (q, J=7.8 Hz, 2H), 1.20 (t, J=7.8 Hz, 3H).

Example 3

(2-((3,5-dicyano-6-(dimethylamino)-4-ethylpyridin-2-yl)thio)-2-(4-((methylsulfonyl)oxy)phenyl)acetyl)phosphoramidic acid

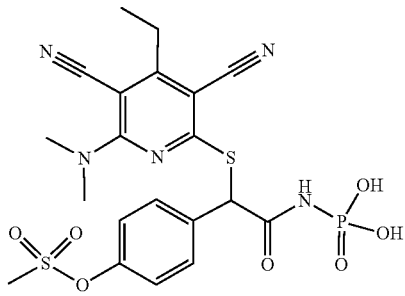 [SMILES: CCc1c(C#N)c(SC(C(=O)NP(=O)(O)O)c2ccc(OS(C)(=O)=O)cc2)nc(N(C)C)c1C#N]

To a solution of 4-(2-((bis(benzyloxy)phosphoryl)amino)-1-((3,5-dicyano (dimethylamino)-4-ethylpyridin-2-yl)thio)-2-oxoethyl)phenyl methanesulfonate (77.34 g, 107 mmol) in acetonitrile (1 L) at 0° C. was added iodotrimethylsilane (34 mL, 247 mmol) and the mixture was warmed to room temperature. The reaction mixture was stirred at room temperature for 30 min. The reaction was quenched with 1.2 L of 10% sodium metabisulfite. A precipitate formed and the thick mixture was stirred. The mixture was filtered and the collected solid washed with 1 L of water. Dried in the filter funnel under vacuum overnight. The resulting solid was suspended in 2 L of ether and stirred for 30 min. The mixture was filtered and the collected solid dried to give (2-((3,5-dicyano-6-(dimethylamino)-4-ethylpyridin-2-yl)thio)-2-(4-((methylsulfonyl)oxy)phenyl)acetyl)phosphoramidic acid (32 g, 59.3 mmol, 55.2% yield) as an off-white solid. LCMS m/z=540.0 [M+H]⁺. ¹H NMR (400 MHz, DMSO-d₆) δ ppm 9.48 (s, 1H), 7.66 (d, J=8.5 Hz, 2H), 7.35 (d, J=8.5 Hz, 2H), 5.81 (s, 1H), 3.40 (s, 3H), 3.34 (s, 6H), 2.74 (q, J=7.6 Hz, 2H), 1.20 (t, J=7.6 Hz, 3H) (2 phosphate protons not observed).

Example 4

4-(2-amino-1-((3,5-dicyano-6-(dimethylamino)-4-ethylpyridin-2-yl)thio)-2-oxoethyl)phenyl methanesulfonate

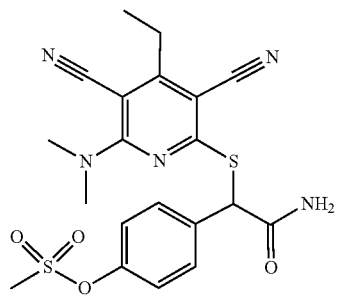 [SMILES: CCc1c(C#N)c(SC(C(N)=O)c2ccc(OS(C)(=O)=O)cc2)nc(N(C)C)c1C#N]

To a yellow suspension of 2-(dimethylamino)-4-ethyl-6-mercaptopyridine-3,5-dicarbonitrile (2.0 g, 8.61 mmol) in ethyl acetate (50 mL) was sequentially added DIEA (1.880 mL, 10.76 mmol) and 4-(2-amino-1-((methylsulfonyl)oxy)-2-oxoethyl)phenyl methanesulfonate (2.78 g, 8.61 mmol) in one portion. The mixture was stirred at room temperature for 24 hours. The solid was collected by filtration, rinsed with ethyl acetate, water, and more ethyl acetate. The solid was dried to give 3.50 g of a pale yellow solid. The solid material was suspended in 30 mL of water and stirred for 1 hour. The solid was collected by filtration, rinsed with water, and dried to provide 4-(2-amino-1-((3,5-dicyano (dimethylamino)-4-ethylpyridin-2-yl)thio)-2-oxoethyl)phenyl methanesulfonate (3.09 g, 76%) as a pale yellow solid. LCMS m/z=460.0 [M+H]$^+$. $^1$H NMR (400 MHz, DMSO-d$_6$) δ ppm 7.97 (s, 1H), 7.65-7.59 (m, 2H), 7.41-7.34 (m, 3H), 5.65 (s, 1H), 3.40 (s, 3H), 3.33 (s, 6H), 2.75 (q, J=7.6 Hz, 2H), 1.20 (t, J=7.6 Hz, 3H).

Biological Data

DNMT1 Scintillation Proximity Assay (SPA)—Assay A (Full-Length Human DNMT1)

This assay used Scintillation Proximity technology in a signal increase format to evaluate the potency of compounds. Full-length human DNMT1, hemi-methylated DNA duplex*, and tritiated SAM were utilized to monitor activity. Assay plate creation consisted of the following parameters: 500 nL of an 11 pt, 3-fold serial dilution of compound was stamped into a 96 well Costar plate (#3884). Assay buffer mix was made on the day of assay consisting of: 20 mM Tris pH 7.5, 1 mM DTT, 1 mM EDTA, and 5% glycerol. A 2× enzyme mix was then prepared consisting of 30 nM DNMT1 protein (full length human DNMT, made in house) in assay buffer. The 2× substrate mix was made last, and consisted of 160 nM 40mer hemi-methylated DNA*, 0.48 µM $^3$H-SAM, and 2.92 µM cold SAM in assay buffer ($^3$H-SAM is added last). The quench (1 mM SAH) was made in bulk and frozen at −20 until the time of use. Ten uL of the 2× substrate mix was added to the entire plate using a multichannel electronic pipette. Plate was shaken for at least 10s between additions to ensure mixing. Next, 20 uL of 2× quench mix was added to column 12 using a multichannel pipette (shake plate). Using a multichannel electronic pipette, 10 uL of 2× enzyme mix was added to the full plate starting with column 11 and moving to column 10 (column 12 last to avoid pre-quench carryover). Plates were incubated on the shaker for 30 minutes with the plate covered. At the end of the incubation period, 20 uL of quench mix were added to all wells except column 12 (shake plate) followed by the addition of 20 uL of 3 mg/mL PerkinElmer PEI PVT SPA Beads (Cat. #RPNQ0097) diluted in DNAse free water and allowed to shake for at least 30 minutes. Plates were sealed with a clear seal and centrifuged at 500 rpm for 1 min. Plates were read on a MicroBeta (Perkin Elmer, read for $^3$H (1 min/well).

Microsoft Excel was used to analyze the data up to Vi/Vo and GraFit was used to fit the data. Responses were normalized to the uninhibited (DMSO) and pre-quenched controls within each plate. Dose-response curves were analyzed using a three-parameter logistic fit with Y$_{min}$ constrained to 0 and results were expressed as IC$_{50}$ values.

Final assay conditions: 20 mM Tris (Hampton Research—HR-937-06), pH 7.5, 1 mM DTT (Invitrogen—P2325), 1 mM EDTA (Invitrogen—AM9260G), 5% Glycerol (Teknova—G1796), 0.02% Pluronic F127 (Life Technologies—P6866), 15 nM DNMT1 (full length human DNMT1—GSK made in-house), 240 nM $^3$H-SAM (PerkinElmer—NET155H001MC), 1460 nM cold SAM (New England Biolabs—B9003S) and 80 nM 40-mer hemi-methylated DNA Oligonucleotide (Integrated DNA Technologies—custom), 1 mM SAH (Sigma A9384), and 1 mg/mL PEI PVT SPA Beads (Perkin Elmer RPNQ0097) resuspended in water.

* 40Mer Me-DNA Oligomer Duplex:

```
5'-CCTCTTCTAACTGCCAT(Me-dC)GATCCTGATAGCAGGTGC
ATGC-3'

5'-GCATGCACCTGCTATCAGGATCGATGGCAGTTAGAAGAGG-3'
```

DNMT1 Scintillation Proximity Assay (SPA)—Assay B (Human Truncated DNMT1(601-1600))

This assay used Scintillation Proximity technology in a signal increase format to evaluate the potency of compounds. Human truncated DNMT1(601-1600), single hemi-methylated CpG site oligonucleotide, and Tritiated SAM were utilized to monitor activity. Assay plate creation consisted of the following parameters: 10 mM Compounds (11-point, 3-fold serial dilution) were stamped at 100 nL per well (100× in 100% DMSO) into a Griener white LV 384 well plate (#784075). Assay buffer mix was made on the day of assay consisting of: base buffer: (500 mM Hepes, ph 8, 1M MgCl2 made in advance, stored at room temp as a stock), 10% NP40-Surfact AMPS, 10% Ultrapure BSA 50 mg/ml, and 2M DTT (DL-Dithiolthreitol). The 2× enzyme mix was then prepared consisting of: DNMT1 protein (truncate human DNMT1—601-1600, made in house at 16.876 uM stock concentration) added to the assay buffer mix. The 2× substrate mix was made last, and consists of: 1 mM 40-mer hemi-methylated DNA Oligonucleotide, 12.5 uM 3H-SAM (Adenosyl-L-Methionine-S-[methyl-3H] Specific Activity 55-85 Ci/mmol) and 32 mM solution of S-Adenosyl-L-Methionine (this was diluted to 1 mM in Nuclease Free-H2O before adding to substrate mix) added into the assay buffer mix (3H-SAM is added last). Five uL of the assay buffer mix was dispensed into column 18 ONLY using a Thermo Multidrop combi. Next, 5 uL of the 2× Enzyme mix was dispensed to columns 1-17, 19-24 using a Thermo Multidrop combi. Then 5 uL of the 2× Substrate mix was dispensed to the full plate using a Thermo Multidrop combi. Plates were stacked and incubated for 40 minutes with a cover plate over the top plate. The quench mix was made around the 25 minute mark of the incubation step, which consisted of: 32 mM solution of S-Adenosyl-L-Methionine & PerkinElmer PEI PS Imaging Beads (Cat. #RPNQ0098) (10 mg/ml) into Nuclease Free-H2O. The quench mix was vortexed prior to use to get the beads in solution. After the 40 minute incubation, 10 uL of the quench mix was dispensed to the full plate using a Thermo Multidrop combi. Plates were sealed with a clear seal and centrifuged at 1000 rpm/1 min and dark adapted for 30 minutes. Plates were read on a Viewlux (PerkinElmer, 613 nm emission filter, 300 sec dual-exposure, (10 min. total read time)).

The Abase database was used to analyze the data. Responses were normalized to the uninhibited (DMSO) and low controls within each plate. Dose-response curves were analyzed using a four-parameter logistic fit and results were expressed as pIC$_{50}$ values.

Final assay conditions: 50 mM HEPES (Teknova—H1035), pH 8.0, 2 mM MgCl2 (Sigma—M1028), 1 mM DTT (Sigma—D5545), 0.01% NP40 Surfactant Amps (Themo Scientific—28324), 0.01% BSA (Ambion—AM2618), 40 nM DNMT1 (truncate human DNMT1 (601-1600—GSK made in-house), 100 nM 3H-SAM (American Radiolabeled Chemicals Inc—ART 0288), 900 nM cold SAM (New England Biolabs—B9003S) and 200 nM 40-mer hemi-methylated DNA Oligonucleotide (Integrated DNA Technologies—43334514).

Solubility of Solid Compounds in Fasted Simulated Intestinal Fluid

The solubility of solid compounds in Fasted Simulated Intestinal Fluid (FaSSIF) was determined at pH 6.5 after 4 hour equilibration at room temperature (using procedures described in Sou, T.; Bergström, C. A. S. Automated assays for thermodynamic (equilibrium) solubility determination. Drug Discovery Today: Technologies 2018, 27, 11-19). 1 ml of FaSSIF buffer (3 mM Sodium taurocholate, 0.75 mM lecithin in sodium phosphate buffer at pH6.5) was added to manually weighed 1 mg of solid compound in a 4 ml vial. The resulting suspension was shaken at 900 rpm for 4 hours at room temperature and then transferred to a Multiscreen HTS, 96-well solubility filter plate to separate the residual solid and the filtrate. Quantification of the compound concentration in the filtrate was performed by HPLC-UV using single point calibration of a known concentration of the compound in DMSO. A set of 3 internal standards of known solubility (Atovaquone, Nimesulide and Warfarin of 2.20 and 140 µg/ml respectively) were tested alongside the compounds to assess the suitability of the process. The dynamic range of the assay was 1-1000 µg/ml.

Results

| Compound | Structure | DNMT1 IC$_{50}$ (nM) | Rat Oral Bioavailability (%) | FaSSIF Solubility (µg/mL) |
|---|---|---|---|---|
| Example 1 | 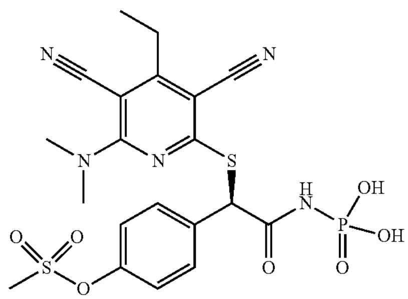 [SMILES: CCc1c(C#N)c(S[C@@H](C(=O)NP(=O)(O)O)c2ccc(OS(C)(=O)=O)cc2)nc(N(C)C)c1C#N] | 16139$^a$ | | >1000 |
| Example 2 | 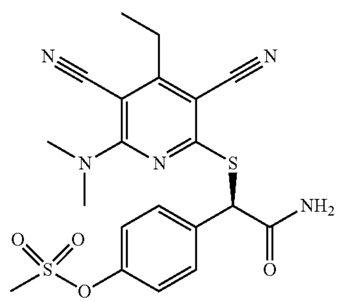 [SMILES: CCc1c(C#N)c(S[C@@H](C(N)=O)c2ccc(OS(C)(=O)=O)cc2)nc(N(C)C)c1C#N] | 54$^a$ | 40 | 1 |
| Example 3 | 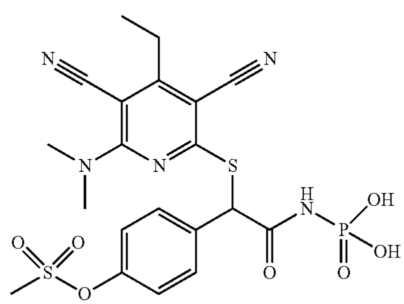 [SMILES: CCc1c(C#N)c(SC(C(=O)NP(=O)(O)O)c2ccc(OS(C)(=O)=O)cc2)nc(N(C)C)c1C#N] | 5209$^a$ | | >1000 |
| Example 4 | 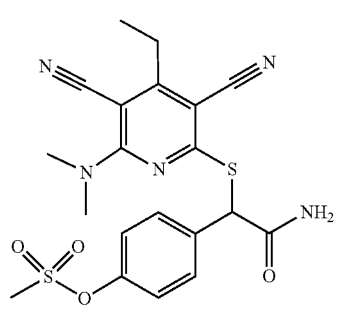 [SMILES: CCc1c(C#N)c(SC(C(N)=O)c2ccc(OS(C)(=O)=O)cc2)nc(N(C)C)c1C#N] | 107$^a$ | | <1 |

-continued

| Compound | Structure | DNMT1 IC$_{50}$ (nM) | Rat Oral Bioavailability (%) | FaSSIF Solubility (μg/mL) |
| --- | --- | --- | --- | --- |
| Reference compound 1 | 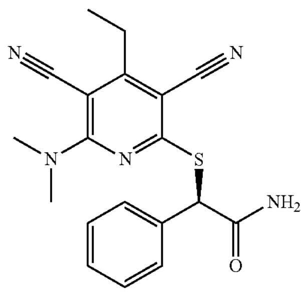 [SMILES: CCc1c(C#N)c(S[C@@H](C(N)=O)c2ccccc2)nc(N(C)C)c1C#N] | 89[a] | | <1 |
| Reference compound 2 | 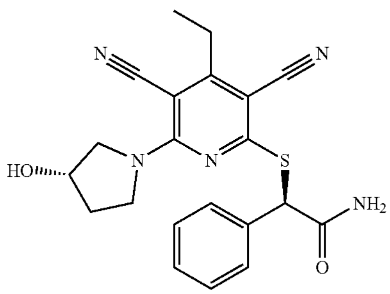 [SMILES: CCc1c(C#N)c(S[C@@H](C(N)=O)c2ccccc2)nc(N2CC[C@H](O)C2)c1C#N] | 156[a] | | 2.7 |
| Reference compound 3 | 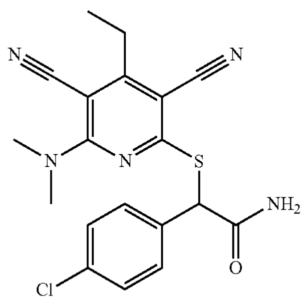 [SMILES: CCc1c(C#N)c(SC(C(N)=O)c2ccc(Cl)cc2)nc(N(C)C)c1C#N] | 631[b] | | |
| Reference compound 4 | 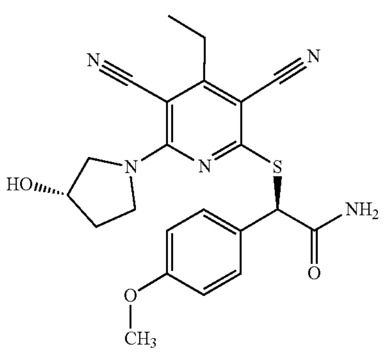 [SMILES: CCc1c(C#N)c(S[C@@H](C(N)=O)c2ccc(OC)cc2)nc(N2CC[C@H](O)C2)c1C#N] | 79[b] | 6.1 | 4 |

[a] DNMT1 full length
[b] DNMT1 truncate

Pharmacokinetic Studies: All studies were conducted in accordance with the GSK Policy on the Care, Welfare and Treatment of Laboratory Animals and were reviewed either by the Institutional Animal Care and Use Committee at GSK or by the ethical review process at the institution where the studies were performed. Pharmacokinetic studies for example 2 were conducted using non-fasted, Male Wistar Han rats, n=3/dose route and for reference compound 4, non-fasted male Sprague-Dawley rats, n=2/dose route in a non-crossover design. Compounds were prepared as solutions in 5% DMA/15% Solutol and administered as a 60 minute IV infusion and PO gavage. Blood samples were collected serially at multiple time points from pre-dose through 24 hours post dose and the analytes were quantified by LC/MS/MS. The percent bioavailability was calculated by comparison of the dose normalized Area Under the Curve (DNAUC) obtained from PO dosing with the DNAUC from the IV route [(PO DNAUC/IV DNAUC)*100].

In Vivo Mouse Study—Methods:

SKM-1 cells (3.8×10⁶) suspended in 50% Matrigel (BD Biosciences)/50% Dulbecco's phosphate-buffered saline (DPBS) were implanted in 8-11 week old female NOD.CB17-Prkdc<scid>1NCrCrl mice. Tumors were measured with digital calipers, and stratified block randomized according to tumor size (P value >0.9085) into treatment groups with average tumor volumes of 219 or 1076 mm³ for efficacy or PK/PD studies respectively. GSK4172239A was formulated weekly in Sterile water. Mice were measured twice weekly for body weight and tumor size. Dosing started on the day after randomization. Animals were dosed twice daily (BID) via oral gavage (PO) with Example 1 at 22, 67, or 200 mg/kg. A maximal tumor burden of 2,500 mm³ for two consecutive measurements was not exceeded during the studies. For the PK/PD study, tumor, blood, and bone marrow were collected two hours following the 20th dose (10 days). For PK, blood was mixed 50:50 with water while tumor was homogenized (Omni hand-held homogenizer) in sterile water at a 1:4 dilution. Both samples were precipitated with acetonitrile, and concentrations of Example 4 were determined by HPLC—MS/MS (Waters Acquity uPLC, Sciex API5000). SKM-1 tumor and mouse bone marrow samples were assessed using a global DNA methylation (5-methylcytosine) LC-MS/MS assay. DNA was isolated using the Quick-DNA Miniprep Kit (Zymo Research) according to the manufacturer's instructions. For each sample, DNA Degradase Plus (Zymo Research) was added according to the manufacturer's instructions to 1,250 ng of DNA to release individual nucleosides from genomic DNA. Degradase-treated DNA (10 μl) was combined with 190 μl of acetonitrile/water/ammonium hydroxide (90:10:0.1) solution containing 100 ng/ml 2'-deoxycytidine-13C,15N₂ (Toronto Research Chemicals) and 10 ng/ml 5-Methyl-2'-deoxycytidine-13C,15N₂ (Toronto Research Chemicals) labeled standards. An HPLC—MS/MS method was optimized to quantify 2'-deoxycytidine and 5-methyl-2'-deoxycytidine. The analytes and labeled standard were separated by HILIC (hydrophilic interaction liquid chromatography) using an Acquity BEH Amide, 1.7 μm, 2.1×50 mm² column on a Waters Acquity UPLC followed by MS/MS analysis on a Sciex API5000 employing positive-ion turbo spray ionization. Concentrations of 2'-deoxycytidine and 5-methyl-2'-deoxycytidine were determined using standard curves generated from pure 2'-deoxycytidine (Sigma-Aldrich) and 5-methyl-2'-deoxycytidine (Santa Cruz Biotechnology). Concentrations of 5-methylcytosine were normalized to total cytosine concentrations to determine percentage of 5-methylcytosine. Values from treated samples were normalized to vehicle control.

In Vivo Mouse Study—Results:

Example 1 displays in vivo activity. Example 1 was evaluated in immunocompromised mice bearing subcutaneous SKM-1 human AML (acute myeloid leukemia) xenografts. Animals were dosed twice daily (BID) via oral gavage (PO) with Example 1 at 22, 67, or 200 mg/kg. To examine pharmacokinetic (PK) and pharmacodynamic (PD) changes, tumor, blood, and bone marrow were collected two hours following the 20th dose (10 days; n=5 animals per group). Pharmacokinetic evaluation revealed drug exposure (measured as the racemic active moiety Example 4) was dose-proportional and roughly equivalent in blood and tumor. In addition, the mechanistic consequence of inhibiting DNMT1, a decrease in DNA methylation, was assessed globally using a LC-MS/MS-based 5-methylcytosine assay. Global DNA methylation was reduced at all doses of Example 1 in comparison to vehicle with a maximal change of 49% in the tumor and 47% in the bone marrow observed with the 200 mg/kg group. In a subsequent study, to examine anti-tumor efficacy, tumor volume was measured (n=10 animals per group) twice weekly for 4 weeks while on treatment. Example 1 induced a dose-dependent reduction in tumor volume with tumor growth inhibition ranging from an average of 35% in the 22 mg/kg group to marked regression in the 200 mg/kg group when compared to vehicle at day 22, the last day the vehicle group contained 9 animals.

The invention claimed is:

1. A compound of formula (I)

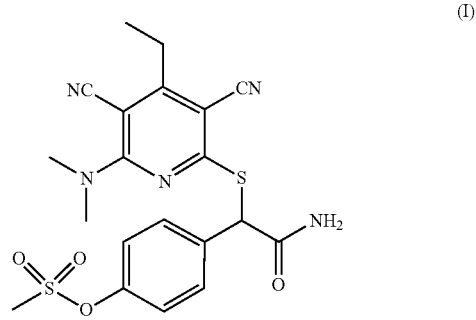 [SMILES: CCc1c(C#N)c(SC(C(N)=O)c2ccc(OS(C)(=O)=O)cc2)nc(N(C)C)c1C#N]

or a prodrug or a pharmaceutically acceptable salt thereof.

2. A compound of formula (II)

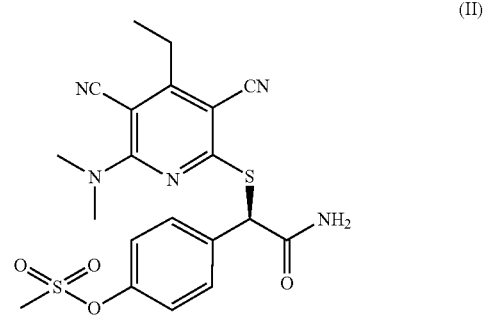 [SMILES: CCc1c(C#N)c(S[C@@H](C(N)=O)c2ccc(OS(C)(=O)=O)cc2)nc(N(C)C)c1C#N]

or a prodrug or a pharmaceutically acceptable salt thereof.

3. A compound of formula (IV)

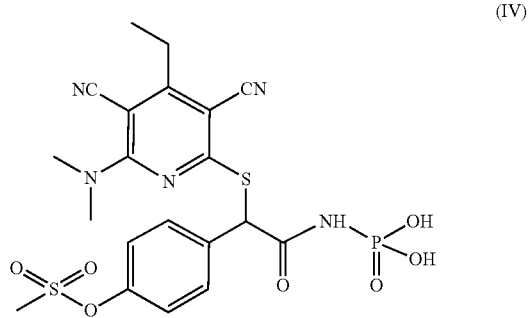 [SMILES: CCc1c(C#N)c(SC(C(=O)NP(=O)(O)O)c2ccc(OS(C)(=O)=O)cc2)nc(N(C)C)c1C#N]

or a pharmaceutically acceptable salt thereof.

4. A compound of formula (V)

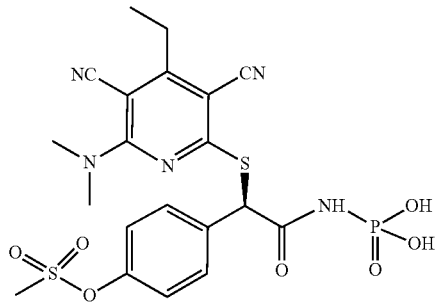

or a pharmaceutically acceptable salt thereof.

5. The compound according to claim 4, which is a glycine salt having a formula of

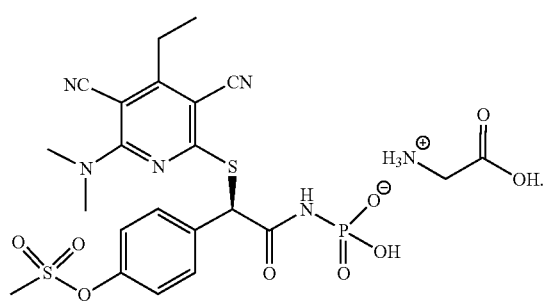 [SMILES: CCc1c(C#N)c(S[C@@H](C(=O)NP(=O)([O-])O)c2ccc(OS(C)(=O)=O)cc2)nc(N(C)C)c1C#N ; [NH3+]CC(=O)O]

6. The glycine salt according to claim 5, wherein the salt is crystalline.

7. The glycine salt according to claim 6, wherein the salt is anhydrous.

8. A pharmaceutical composition comprising the compound according to claim 4, or a pharmaceutically acceptable salt thereof, and one or more pharmaceutically acceptable excipients.

9. A combination comprising the compound of claim 4, or a pharmaceutically acceptable salt thereof, and one or more other active agents.

10. The glycine salt according to claim 6, wherein the salt is hydrated.

11. The glycine salt according to claim 10, wherein the salt is a monohydrate.

12. A pharmaceutical composition comprising the compound according to claim 5 and one or more pharmaceutically acceptable excipients.

13. A combination comprising the compound of claim 5 and one or more other active agents.

14. The compound according to claim 1, having formula (I)

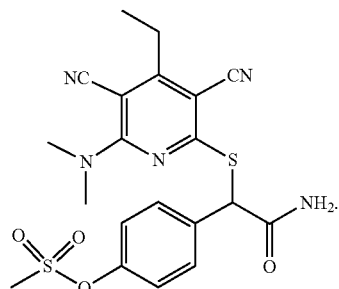

15. The compound according to claim 2, having formula (II)

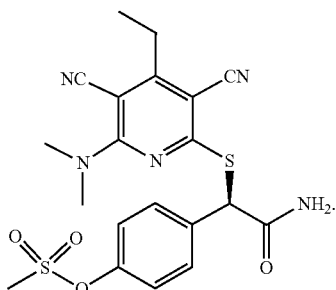

16. The compound according to claim 3, having formula (IV)

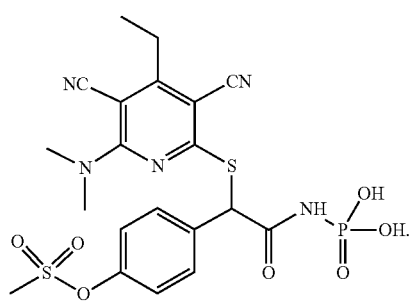

17. The compound according to claim 4, having formula (V)

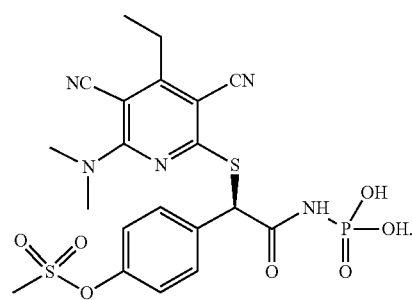

* * * * *